US012527788B2

(12) United States Patent
Disney et al.

(10) Patent No.: US 12,527,788 B2

(45) Date of Patent: Jan. 20, 2026

(54) DEFINING RNA-SMALL MOLECULE AFFINITY LANDSCAPES ENABLES DESIGN OF A SMALL MOLECULE INHIBITOR OF AN ONCOGENIC NON-CODING RNA

(71) Applicant: University of Florida Research Foundation, Incorporated, Gainesville, FL (US)

(72) Inventors: Matthew D. Disney, Jupiter, FL (US); Sai Pradeep Velagapudi, Jupiter, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 1892 days.

(21) Appl. No.: 16/486,223

(22) PCT Filed: Feb. 16, 2018

(86) PCT No.: PCT/US2018/000020

§ 371 (c)(1),
(2) Date: Aug. 15, 2019

(87) PCT Pub. No.: WO2018/151810

PCT Pub. Date: Aug. 23, 2018

(65) Prior Publication Data

US 2024/0293398 A1 Sep. 5, 2024

Related U.S. Application Data

(60) Provisional application No. 62/460,184, filed on Feb. 17, 2017.

(51) Int. Cl.

| | |
|---|---|
| ***A61K 31/496*** | (2006.01) |
| ***A61P 35/00*** | (2006.01) |
| ***C07D 235/18*** | (2006.01) |
| ***C12N 15/10*** | (2006.01) |

(52) U.S. Cl.

CPC ............ *A61K 31/496* (2013.01); *A61P 35/00* (2018.01); *C07D 235/18* (2013.01); *C12N 15/1065* (2013.01)

(58) Field of Classification Search

CPC ..... A61K 31/496; A61P 35/00; C07D 235/18; C12N 15/1065

See application file for complete search history.

(56) References Cited

U.S. PATENT DOCUMENTS

| | | | |
|---|---|---|---|
| 8,071,562 | B2 | 12/2011 | Bader et al. |
| 9,586,944 | B2 | 3/2017 | Disney et al. |
| 9,933,419 | B2 | 4/2018 | Disney et al. |
| 10,157,261 | B2 | 12/2018 | Disney et al. |
| 11,636,918 | B2 | 4/2023 | Disney et al. |
| 2008/0188377 | A1 | 8/2008 | Disney et al. |
| 2008/0227213 | A1 | 9/2008 | Disney |
| 2010/0190826 | A1 | 7/2010 | Kakefuda et al. |
| 2012/0277178 | A1 | 11/2012 | Jin et al. |
| 2014/0212945 | A1 | 7/2014 | Disney |
| 2016/0188791 | A1 | 6/2016 | Disney |
| 2016/0194696 | A1 | 7/2016 | Guan et al. |

(Continued)

FOREIGN PATENT DOCUMENTS

| | | | |
|---|---|---|---|
| CN | 110494443 | A | 11/2019 |
| WO | WO 2005/068433 | A1 | 7/2005 |

(Continued)

OTHER PUBLICATIONS

International Search Report and Written Opinion for Application No. PCT/US2018/000020, mailed Jun. 27, 2018.

Childs-Disney et al., A Small Molecule Microarray Program Platform to Select RNA Internal Loop-Ligand Interactions. ACS Chem Biol. Nov. 20, 2007;2(11):745-54. doi: 10.1021/cb700174r. Epub Nov. 2, 2007.

Costales et al., A Designed Small Molecule Inhibitor of a Non-Coding RNA Sensitizes HER2 Negative Cancers to Herceptin. J Am Chem Soc. Feb. 20, 2019;141(7):2960-2974. doi: 10.1021/jacs.8b10558. Epub Feb. 6, 2019.

(Continued)

*Primary Examiner* — Clinton A Brooks

*Assistant Examiner* — Jerica Katlynn Wilson

(74) *Attorney, Agent, or Firm* — Wolf, Greenfield & Sacks, P.C.

(57) ABSTRACT

RNA drug targets are pervasive in cells but methods to design small molecules that target them are sparse. Herein, we report a general approach to score the affinity and selectivity of RNA motif-small molecule interactions identified via selection. Named High Throughput Structure-Activity Relationships Through Sequencing (HiT-StARTS), HiT-StARTS is statistical in nature and compares input nucleic acid sequences to selected library members that bind a ligand via high throughput sequencing. The approach allowed facile definition of the fitness landscape of hundreds of thousands of RNA motif-small molecule binding partners. These results were mined against folded RNAs in the human transcriptome and identified an avid interaction between a small molecule and the Dicer nuclease-processing site in the oncogenic microRNA (miR)-18a hairpin precursor, which is a member of the miR-17-92 cluster. Application of the small molecule, Targapremir-18a, to prostate cancer cells inhibited production of miR-18a from the cluster, de-repressed serine/threonine protein kinase 4 protein (STK4), and triggered apoptosis. Profiling the cellular targets of Targapremir-18a via Chemical Cross Linking and isolation by Pull Down (Chem-CLIP), a covalent small molecule-RNA cellular profiling approach, and other studies showed specific binding of the compound to the miR-18a precursor, revealing broadly applicable factors that govern small molecule drugging of non-coding RNAs.

19 Claims, 12 Drawing Sheets

Specification includes a Sequence Listing.

(56) References Cited

U.S. PATENT DOCUMENTS

| | | | |
|---|---|---|---|
| 2017/0029370 | A1 | 2/2017 | Narayanan et al. |
| 2017/0362650 | A1 | 12/2017 | Zeitlinger et al. |
| 2018/0066262 | A1 | 3/2018 | Domenyuk et al. |
| 2018/0267028 | A1 | 9/2018 | Disney et al. |
| 2019/0156912 | A1 | 5/2019 | Disney et al. |
| 2019/0270723 | A1 | 9/2019 | Kumaravel et al. |
| 2020/0115372 | A1 | 4/2020 | Petter et al. |
| 2020/0324287 | A1 | 10/2020 | Vijayan et al. |
| 2020/0385709 | A1 | 12/2020 | Wagner |
| 2021/0008208 | A1 | 1/2021 | Poma et al. |
| 2021/0379188 | A1 | 12/2021 | Disney |
| 2022/0073910 | A1 | 3/2022 | Disney |
| 2022/0119868 | A1 | 4/2022 | Disney |
| 2022/0251545 | A1 | 8/2022 | Disney |
| 2022/0267839 | A1 | 8/2022 | Disney |
| 2023/0002329 | A1 | 1/2023 | Disney et al. |
| 2023/0041228 | A1 | 2/2023 | Disney |
| 2023/0149554 | A1 | 5/2023 | Disney |
| 2025/0051762 | A1 | 2/2025 | Disney et al. |

FOREIGN PATENT DOCUMENTS

| | | | | |
|---|---|---|---|---|
| WO | WO 2006/133022 A2 | 12/2006 | | |
| WO | WO 2007/127212 A2 | 11/2007 | | |
| WO | WO 2008/066873 A2 | 6/2008 | | |
| WO | WO 2008/103489 A2 | 8/2008 | | |
| WO | WO 2009/036000 A2 | 3/2009 | | |
| WO | WO 2011/150494 A1 | 12/2011 | | |
| WO | WO 2013/019469 A1 | 2/2013 | | |
| WO | WO 2015/009678 A2 | 1/2015 | | |
| WO | WO-2015021415 A1 * | 2/2015 | .......... | C07D 235/18 |
| WO | WO 2016/085659 A1 | 6/2016 | | |
| WO | WO 2016/191604 A1 | 12/2016 | | |
| WO | WO 2017/196264 A1 | 11/2017 | | |
| WO | WO 2018/006074 A2 | 1/2018 | | |
| WO | WO 2018/098297 A1 | 5/2018 | | |
| WO | WO 2018/151810 A1 | 8/2018 | | |
| WO | WO 2019/109046 A1 | 6/2019 | | |
| WO | WO 2019/209975 A1 | 10/2019 | | |
| WO | WO 2019/231821 A1 | 12/2019 | | |
| WO | WO 2020/076511 A1 | 4/2020 | | |
| WO | WO 2021/087084 A1 | 5/2021 | | |

OTHER PUBLICATIONS

Costales et al., Small Molecule Inhibition of microRNA-210 Reprograms an Oncogenic Hypoxic Circuit. J Am Chem Soc. Mar. 8, 2017;139(9):3446-3455. doi: 10.1021/jacs.6b11273. Epub Feb. 27, 2017. Author manuscript, 24 pages.

Costales et al., Small-molecule targeted recruitment of a nuclease to cleave an oncogenic RNA in a mouse model of metastatic cancer. Proc Natl Acad Sci U S A. Feb. 4, 2020;117(5):2406-2411. doi: 10.1073/pnas.1914286117. Epub Jan. 21, 2020. Correction to Supporting Information for Small-molecule targeted recruitment of a nuclease to cleave an oncogenic RNA in a mouse model of metastatic cancer. Proc Natl Acad Sci U S A. May 3, 2022;119(18):e2204149119. doi: 10.1073/pnas.2204149119. Epub Apr. 26, 2022. Supporting information included. 149 pages total.

Costales et al., Targeted Degradation of a Hypoxia-Associated Non-coding RNA Enhances the Selectivity of a Small Molecule Interacting with RNA. Cell Chem Biol. Aug. 15, 2019;26(8):1180-1186.e5. doi: 10.1016/j.chembiol.2019.04.008. Epub May 23, 2019.

Disney et al., Identifying and validating small molecules interacting with RNA (SMIRNAs). Methods Enzymol. 2019:623:45-66. doi: 10.1016/bs.mie.2019.04.027. Epub May 15, 2019.

Disney et al., Two-Dimensional Combinational Screening Identifies Specific Aminoglycoside-RNA Internal Loop Partners. J Am Chem Soc. Aug. 20, 2008;130(33):11185-94. doi: 10.1021/ja803234t. Epub Jul. 25, 2008.

Guan et al., Recent Advances in Developing Small Molecules Targeting RNA. ACS Chem Biol. Jan. 20, 2012;7(1):73-86. doi: 10.1021/cb200447r. Epub Jan. 12, 2012.

Lang et al., DOCK 6: combining techniques to model RNA-small molecule complexes. RNA. Jun. 2009;15(6):1219-30. doi: 10.1261/rna.1563609. Epub Apr. 15, 2009.

Li Y et al., Precise Small Molecule Degradation of a Noncoding RNA Identifies Cellular Binding Sites and Modulates an Oncogenic Phenotype. ACS Chem Biol. Nov. 16, 2018;13(11):3065-3071. doi: 10.1021/acschembio.8b00827. Epub Oct. 30, 2018. Author Manuscript 15 pages.

Liu et al., Targeted Degradation of the Oncogenic MicroRNA 17-92 Cluster by Structure-Targeting Ligands. J Am Chem Soc. Apr. 15, 2020;142(15):6970-6982. doi: 10.1021/jacs.9b13159. Epub Apr. 1, 2020. Author Manuscript 26 pages. Supporting information included. 78 pages total.

Mogilyansky et al., The miR-17/92 cluster: a comprehensive update on its genomics, genetics, functions and increasingly important and numerous roles in health and disease. Cell Death Differ. Dec. 2013;20(12):1603-14. doi: 10.1038/cdd.2013.125.

Norgren et al., On-Resin Click-Glycoconjugation of Peptoids. Synthesis. 2009;3:0488-94. Epub Jan. 9, 2009.

Setny et al., Search for novel aminoglycosides by combining fragment-based virtual screening and 3D-QSAR scoring. J Chem Inf Model. Feb. 2009;49(2):390-400. doi: 10.1021/ci800361a. Author manuscript, 27 pages.

Thomas et al., Targeting RNA with small molecules. Chem Rev. Apr. 2008;108(4):1171-224. doi: 10.1021/cr0681546. Epub Mar. 25, 2008.

Van Meter et al., A review of currently identified small molecule modulators of microRNA function. Eur J Med Chem. Feb. 15, 2020;188:112008. doi: 10.1016/j.ejmech.2019.112008. Epub Dec. 23, 2019.

Velagapudi et al., Defining RNA-Small Molecule Affinity Landscapes Enables Design of a Small Molecule Inhibitor of an Oncogenic Noncoding RNA. ACS Cent Sci. Mar. 22, 2017;3(3):205-216. doi: 10.1021/acscentsci.7b00009. Epub Mar. 6, 2017.

Velagapudi et al., Defining the RNA Internal Loops Preferred by Benzimidazole Derivatives via 2D Combinational Screening and Computational Analysis. J Am Chem Soc. Jul. 6, 2011;133(26):10111-8. doi: 10.1021/ja200212b. Epub Jun. 9, 2011. Author manuscript, 17 pages.

Velagapudi et al., Design of a small molecule against an oncogenic noncoding RNA. Proc Natl Acad Sci U S A. May 24, 2016;113(21):5898-903. doi: 10.1073/pnas.1523975113. Epub May 11, 2016.

Velagapudi et al., Structure-activity relationships through sequencing (StARTS) defines optimal and suboptimal RNA motif targets for small molecules. Angew Chem Int Ed Engl. May 17, 2010;49(22):3816-8. doi: 10.1002/anie.200907257.

Benhamou et al., DNA-encoded library versus RNA-encoded library selection enables design of an oncogenic noncoding RNA inhibitor. Proc Natl Acad Sci U S A. Feb. 8, 2022;119(6):e2114971119. doi: 10.1073/pnas.2114971119. Supporting Information included. 80 pages total.

Disney, Targeting RNA with Small Molecules to Capture Opportunities at the Intersection of Chemistry, Biology, and Medicine. J Am Chem Soc. May 1, 2019;141(17):6776-6790. doi: 10.1021/jacs.8b13419. Epub Apr. 19, 2019. Author manuscript, 29 pages.

Kunig et al., DNA-encoded libraries—an efficient small molecule discovery technology for the biomedical sciences. Biol Chem. Jun. 27, 2018;399(7):691-710. doi: 10.1515/hsz-2018-0119.

Rädle et al., Metabolic labeling of newly transcribed RNA for high resolution gene expression profiling of RNA synthesis, processing and decay in cell culture. J Vis Exp. Aug. 8, 2013;(78):50195. doi: 10.3791/50195. 11 pages.

Yang et al., Design of a bioactive small molecule that targets r(AUUCU) repeats in spinocerebellar ataxia 10. Nat Commun. Jun. 1, 2016;7:11647. doi: 10.1038/ncomms11647.

Yang et al., Inhibition of Non-ATG Translational Events in Cells via Covalent Small Molecules Targeting RNA. J Am Chem Soc. Apr. 29, 2015;137(16):5336-45. doi: 10.1021/ja507448y. Epub Apr. 15, 2015. Author manuscript, 22 pages.

Zhang et al., miR-17-92 cluster and authophagy in cancer. Chinese Bulletin of Life Sciences. Nov. 2017;29(11):1149-55.

(56) References Cited

OTHER PUBLICATIONS

[No Author Listed], CAS Registry No. 1045308-20-0. Entered Aug. 31, 2008. Chemical Abstracts Service, Columbus, OH.
Abraham et al., RNA cleavage and inhibition of protein synthesis by bleomycin. Chem Biol. Jan. 2003;10(1):45-52. doi: 10.1016/s1074-5521(02)00306-x.
Agarwal et al., Predicting effective microRNA target sites in mammalian mRNAs. Elife. Aug. 12, 2015;4:e05005. doi: 10.7554/eLife.05005.
Angelbello et al., Bleomycin Can Cleave an Oncogenic Noncoding RNA. Chembiochem. Jan. 4, 2018;19(1):43-47. doi: 10.1002/cbic.201700581. Epub Nov. 22, 2017. Author manuscript, 10 pages.
Berger et al., Activity-based protein profiling: applications to biomarker discovery, in vivo imaging and drug discovery. Am J Pharmacogenomics. 2004;4(6):371-81. doi: 10.2165/00129785-200404060-00004.
Berry et al., DNA damage and growth inhibition in cultured human cells by bleomycin congeners. Biochemistry. Jun. 18, 1985;24(13):3207-14. doi: 10.1021/bi00334a020.
Bevilacqua et al., Genome-Wide Analysis of RNA Secondary Structure. Annu Rev Genet. Nov. 23, 2016;50:235-266. doi: 10.1146/annurev-genet-120215-035034. Epub Sep. 14, 2016.
Boger et al., Definition of the Effect and Role of the Bleomycin A2 Valerate Substituents: Preorganization of a Rigid, Compact Conformation Implicated in Sequence-Selective DNA Cleavage. J. Am. Chem. Soc. 1998;120(36):9149-58.
Boger et al., Synthesis of key analogs of bleomycin A2 that permit a systematic evaluation of the linker region: identification of an exceptionally prominent role for the L-threonine substituent. Bioorg Med Chem. Sep. 1995;3(9):1281-95. doi: 10.1016/0968-0896(95)00113-u.
Boger et al., Total Synthesis of Bleomycin A2 and Related Agents. 1. Synthesis and DNA Binding Properties of the Extended C-Terminus: Tripeptide S, Tetrapeptide S, Pentapeptide S, and Related Agents. J. Am. Chem. Soc. Jun. 1994;116(13):5607-18.
Burger, Cleavage of Nucleic Acids by Bleomycin. Chem Rev. May 7, 1998;98(3):1153-1169. doi: 10.1021/cr960438a.
Carter et al., Site-specific cleavage of RNA by Fe(II).bleomycin. Proc Natl Acad Sci U S A. Dec. 1990;87(23):9373-7. doi: 10.1073/pnas.87.23.9373.
Childs-Disney et al., A Massively Parallel Selection of Small Molecule-RNA Motif Binding Partners Informs Design of an Antiviral from Sequence. Chem. Oct. 11, 2018;4(10):2384-2404. doi: 10.1016/j.chempr.2018.08.003. Epub Sep. 13, 2018.
Childs-Disney et al., Approaches to Validate and Manipulate RNA Targets with Small Molecules in Cells. Annu Rev Pharmacol Toxicol. 2016;56:123-40. doi: 10.1146/annurev-pharmtox-010715-103910. Epub Oct. 22, 2015.
Childs-Disney et al., Induction and reversal of myotonic dystrophy type 1 pre-mRNA splicing defects by small molecules. Nat Commun. 2013;4:2044. doi: 10.1038/ncomms3044. Author manuscript, 28 pages.
Childs-Disney et al., Rationally designed small molecules targeting the RNA that causes myotonic dystrophy type 1 are potently bioactive. ACS Chem Biol. May 18, 2012;7(5):856-62. doi: 10.1021/cb200408a. Epub Mar. 5, 2012. Author manuscript, 16 pages.
Childs-Disney et al., Using modularly assembled ligands to bind RNA internal loops separated by different distances. Chembiochem. Sep. 19, 2011;12(14):2143-6. doi: 10.1002/cbic.201100298. Epub Aug. 9, 2011. Author manuscript, 9 pages.
Costales et al., Small Molecule Targeted Recruitment of a Nuclease to RNA. J Am Chem Soc. Jun. 6, 2018;140(22):6741-6744. doi: 10.1021/jacs.8b01233. Epub May 24, 2018. Author manuscript, 8 pages.
Cravatt et al., Activity-based protein profiling: from enzyme chemistry to proteomic chemistry. Annu Rev Biochem. 2008;77:383-414. doi: 10.1146/annurev.biochem.75.101304.124125.
Disney et al., Drugging the RNA World. Cold Spring Harb Perspect Biol. Nov. 1, 2018;10(11):a034769. doi: 10.1101/cshperspect.a034769.
Disney et al., Inforna 2.0: A Platform for the Sequence-Based Design of Small Molecules Targeting Structured RNAs. ACS Chem Biol. Jun. 17, 2016;11(6):1720-8. doi: 10.1021/acschembio.6b00001. Epub Apr. 20, 2016. Author manuscript, 19 pages.
Disney et al., Rational Design of Small Molecules Targeting Oncogenic Noncoding RNAs from Sequence. Acc Chem Res. Dec. 20, 2016;49(12):2698-2704. doi: 10.1021/acs.accounts.6b00326. Epub Nov. 22, 2016. Author manuscript, 16 pages.
Encode Project Consortium. An integrated encyclopedia of DNA elements in the human genome. Nature. Sep. 6, 2012;489(7414):57-74. doi: 10.1038/nature11247. Author manuscript, 48 pages.
Frankel et al., Programmed cell death 4 (PDCD4) is an important functional target of the microRNA miR-21 in breast cancer cells. J Biol Chem. Jan. 11, 2008;283(2):1026-33. doi: 10.1074/jbc.M707224200. Epub Nov. 8, 2007.
Graczyk, Gini coefficient: a new way to express selectivity of kinase inhibitors against a family of kinases. J Med Chem. Nov. 15, 2007;50(23):5773-9. doi: 10.1021/jm070562u. Epub Oct. 19, 2007.
Griffiths-Jones et al., miRBase: tools for microRNA genomics. Nucleic Acids Res. Jan. 2008;36(Database issue):D154-8. doi: 10.1093/nar/gkm952. Epub Nov. 8, 2007.
Guan et al., Covalent small-molecule-RNA complex formation enables cellular profiling of small-molecule-RNA interactions. Angew Chem Int Ed Engl. Sep. 16, 2013;52(38):10010-3. doi: 10.1002/anie.201301639. Epub Aug. 1, 2013. Author manuscript, 9 pages.
Guan et al., Small-molecule-mediated cleavage of RNA in living cells. Angew Chem Int Ed Engl. Jan. 28, 2013;52(5):1462-5. doi: 10.1002/anie.201206888. Epub Dec. 20, 2012. Author manuscript, 11 pages.
Guttilla et al., Coordinate regulation of FOXO1 by miR-27a, miR-96, and miR-182 in breast cancer cells. J Biol Chem. Aug. 28, 2009;284(35):23204-16. doi: 10.1074/jbc.M109.031427. Epub Jul. 1, 2009.
Hecht, The Chemistry of Activated Bleomycin. Acc. Chem. Res. Dec. 1986;19:383-91.
Hermann, Small molecules targeting viral RNA. Wiley Interdiscip Rev RNA. Nov. 2016;7(6):726-743. doi: 10.1002/wrna.1373. Epub Jun. 16, 2016.
Howe et al., Selective small-molecule inhibition of an RNA structural element. Nature. Oct. 29, 2015;526(7575):672-7. doi: 10.1038/nature15542. Epub Sep. 30, 2015.
Huang et al., MiR-210—micromanager of the hypoxia pathway. Trends Mol Med. May 2010;16(5):230-7. doi: 10.1016/j.molmed.2010.03.004. Epub Apr. 29, 2010. Author manuscript, 16 pages.
Iliopoulos et al., STAT3 activation of miR-21 and miR-181b-1 via PTEN and CYLD are part of the epigenetic switch linking inflammation to cancer. Mol Cell. Aug. 27, 2010;39(4):493-506. doi: 10.1016/j.molcel.2010.07.023.
Im et al., Identification of aminosulfonylarylisoxazole as microRNA-31 regulators. PLoS One. Aug. 4, 2017;12(8):e0182331. doi: 10.1371/journal.pone.0182331.
Kane et al., Polynucleotide recognition and degradation by bleomycin. Prog Nucleic Acid Res Mol Biol. 1994;49:313-52. doi: 10.1016/s0079-6603(08)60054-9.
Krichevsky et al., miR-21: a small multi-faceted RNA. J Cell Mol Med. Jan. 2009;13(1):39-53. doi: 10.1111/j.1582-4934.2008.00556.x.
Kwok et al., Determination of in vivo RNA structure in low-abundance transcripts. Nat Commun. 2013;4:2971. doi: 10.1038/ncomms3971.
Lee et al., Controlling the specificity of modularly assembled small molecules for RNA via ligand module spacing: targeting the RNAs that cause myotonic muscular dystrophy. J Am Chem Soc. Dec. 2, 2009;131(47):17464-72. doi: 10.1021/ja906877y.
Li et al., Synthesis of linear polyether polyol derivatives as new materials for bioconjugation. Bioconjug Chem. Apr. 2009;20(4):780-9. doi: 10.1021/bc900036f.
Liu et al., Analysis of secondary structural elements in human microRNA hairpin precursors. BMC Bioinformatics. Mar. 1, 2016;17:112. doi: 10.1186/s12859-016-0960-6.
Lu et al., Decoding the RNA structurome. Curr Opin Struct Biol. Feb. 2016;36:142-8. doi: 10.1016/j.sbi.2016.01.007. Epub Feb. 26, 2016. Author manuscript, 11 pages.

(56) References Cited

OTHER PUBLICATIONS

Ma et al., Biochemical Evaluation of a 108-Member Deglycobleomycin Library: Viability of a Selection Strategy for Identifying Bleomycin Analogues with Altered Properties. J. Am. Chem. Soc. Sep. 2007;129(41):12439-52.
Mathews et al., Incorporating chemical modification constraints into a dynamic programming algorithm for prediction of RNA secondary structure. Proc Natl Acad Sci U S A. May 11, 2004;101(19):7287-92. doi: 10.1073/pnas.0401799101. Epub May 3, 2004.
Michlewski et al., Posttranscriptional regulation of miRNAs harboring conserved terminal loops. Mol Cell. Nov. 7, 2008;32(3):383-93. doi: 10.1016/j.molcel.2008.10.013.
Milligan et al., Synthesis of small RNAs using T7 RNA polymerase. Methods Enzymol. 1989;180:51-62. doi: 10.1016/0076-6879(89)80091-6.
Mukherjee et al., PEARL-seq: A Photoaffinity Platform for the Analysis of Small Molecule-RNA Interactions. ACS Chem Biol. Sep. 18, 2020;15(9):2374-2381. doi: 10.1021/acschembio.0c00357. Epub Aug. 17, 2020.
Nakamoto et al., Diazirine-containing tag-free RNA probes for efficient RISC-loading and photoaffinity labeling of microRNA targets. Bioorg Med Chem Lett. Sep. 15, 2018;28(17):2906-2909. doi: 10.1016/j.bmcl.2018.07.020. Epub Jul. 11, 2018.
Nakamoto et al., Labeling of target mRNAs using a photo-reactive microRNA probe. Chem Commun (Camb). May 10, 2016;52(40):6720-2. doi: 10.1039/c6cc01360k.
Naryshkin et al., SMN2 splicing modifiers improve motor function and longevity in mice with spinal muscular atrophy. Science. Aug. 8, 2014;345(6197):688-93. doi: 10.1126/science.1250127.
Nguyen et al., Rationally designed small molecules that target both the DNA and RNA causing myotonic dystrophy type 1. J Am Chem Soc. Nov. 11, 2015;137(44):14180-9. doi: 10.1021/jacs.5b09266. Epub Nov. 3, 2015.
Osborn et al., Platinum-RNA modifications following drug treatment in S. cerevisiae identified by click chemistry and enzymatic mapping. ACS Chem Biol. Oct. 17, 2014;9(10):2404-11. doi: 10.1021/cb500395z. Epub Aug. 15, 2014.
Otsuka et al., Man-designed bleomycin with altered sequence specificity in DNA cleavage. J. Am. Chem. Soc. Jan. 1990;112(2):838-45.
Owa et al., Man-designed bleomycins: Significance of the binding sites as enzyme models and of the stereochemistry of the linker moiety. Tetrahedron. 1992;48(7):1193-208.
Palacino et al., SMN2 splice modulators enhance U1-pre-mRNA association and rescue SMA mice. Nat Chem Biol. Jul. 2015;11(7):511-7. doi: 10.1038/nchembio.1837. Epub Jun. 1, 2015. Erratum in: Nat Chem Biol. Sep. 2015;11(9):741. doi: 10.1038/nchembio0915-741a. Erratum in: Nat Chem Biol. Apr. 2016;12(4):304. doi: 10.1038/nchembio0416-304c.
Parker et al., Ligand and Target Discovery by Fragment-Based Screening in Human Cells. Cell. Jan. 26, 2017;168(3):527-541.e29. doi: 10.1016/j.cell.2016.12.029. Epub Jan. 19, 2017.
Paul et al., Two-dimensional combinatorial screening and the RNA Privileged Space Predictor program efficiently identify aminoglycoside-RNA hairpin loop interactions. Nucleic Acids Res. Sep. 2009;37(17):5894-907. doi: 10.1093/nar/gkp594. Epub Sep. 2, 2009.
Ratmeyer et al., An ethidium analog that binds with high specificity to a base-bulged duplex from the TAR RNA region of the HIV-1 genome. Journal of Medicinal Chemistry. Mar. 1992;35(5):966-8.
Rupaimoole et al., MicroRNA therapeutics: towards a new era for the management of cancer and other diseases. Nat Rev Drug Discov. Mar. 2017;16(3):203-222. doi: 10.1038/nrd.2016.246. Epub Feb. 17, 2017.
Rupaimoole et al., miRNA Deregulation in Cancer Cells and the Tumor Microenvironment. Cancer Discov. Mar. 2016;6(3):235-46. doi: 10.1158/2159-8290.CD-15-0893. Epub Feb. 10, 2016. Author manuscript, 20 pages.
Rzuczek et al., Precise small-molecule recognition of a toxic CUG RNA repeat expansion. Nat Chem Biol. Feb. 2017;13(2):188-193. doi: 10.1038/nchembio.2251. Epub Dec. 12, 2016.
Seike et al., MiR-21 is an EGFR-regulated anti-apoptotic factor in lung cancer in never-smokers. Proc Natl Acad Sci U S A. Jul. 21, 2009;106(29):12085-90. doi: 10.1073/pnas.0905234106. Epub Jul. 13, 2009.
Sexton et al., Interpreting Reverse Transcriptase Termination and Mutation Events for Greater Insight into the Chemical Probing of RNA. Biochemistry. Sep. 5, 2017;56(35):4713-4721. doi: 10.1021/acs.biochem.7b00323. Epub Aug. 18, 2017. Author manuscript, 17 pages.
Shi et al., Overexpression of microRNA-96-5p inhibits autophagy and apoptosis and enhances the proliferation, migration and invasiveness of human breast cancer cells. Oncol Lett. Jun. 2017;13(6):4402-4412. doi: 10.3892/ol.2017.6025. Epub Apr. 11, 2017.
Sicard et al., Targeting miR-21 for the therapy of pancreatic cancer. Mol Ther. May 2013;21(5):986-94. doi: 10.1038/mt.2013.35. Epub Mar. 12, 2013.
Stelzer et al., Discovery of selective bioactive small molecules by targeting an RNA dynamic ensemble. Nat Chem Biol. Jun. 26, 2011;7(8):553-9. doi: 10.1038/nchembio.596. Author manuscript, 15 pages.
Stubbe et al., Mechanisms of bleomycin-induced DNA degradation. Chem. Rev. Oct. 1987;87(5):1107-36.
Suresh et al., A general fragment-based approach to identify and optimize bioactive ligands targeting RNA. Proc Natl Acad Sci U S A. Dec. 29, 2020;117(52):33197-33203. doi: 10.1073/pnas.2012217117. Epub Dec. 14, 2020.
Tenson et al., Antibiotics and the ribosome. Mol Microbiol. Mar. 2006;59(6):1664-77. doi: 10.1111/j.1365-2958.2006.05063.x.
Thakur et al., Small-molecule activators of RNase L with broad-spectrum antiviral activity. Proc Natl Acad Sci U S A. Jun. 5, 2007;104(23):9585-90. doi: 10.1073/pnas.0700590104. Epub May 29, 2007.
Thomas et al., Solid-Phase Synthesis of Bleomycin A5 and Three Monosaccharide Analogues: Exploring the Role of the Carbohydrate Moiety in RNA Cleavage. J. Am. Chem. Soc. Oct. 2002;124(44):12926-7.
Ule et al., CLIP identifies Nova-regulated RNA networks in the brain. Science. Nov. 14, 2003;302(5648):1212-5. doi: 10.1126/science.1090095.
Velagapudi et al., A cross-linking approach to map small molecule-RNA binding sites in cells. Bioorg Med Chem Lett. Jun. 15, 2019;29(12):1532-1536. doi: 10.1016/j.bmcl.2019.04.001. Epub Apr. 2, 2019. Author manuscript, 9 pages.
Velagapudi et al., Sequence-based design of bioactive small molecules that target precursor microRNAs. Nat Chem Biol. Apr. 2014;10(4):291-7. doi: 10.1038/nchembio.1452. Epub Feb. 9, 2014. Author manuscript, 23 pages.
Wang et al., Mechanistic studies of a small-molecule modulator of SMN2 splicing. Proc Natl Acad Sci U S A. May 15, 2018;115(20):E4604-E4612. doi: 10.1073/pnas.1800260115. Epub Apr. 30, 2018.
Xu et al., Synthesis, biological evaluation and DNA binding properties of novel bleomycin analogues. Bioorg Med Chem Lett. Aug. 4, 2003;13(15):2595-9. doi: 10.1016/s0960-894x(03)00435-9.
Yan et al., Design, synthesis and activity of light deactivatable microRNA inhibitor. Bioorg Chem. Oct. 2018;80:492-497. doi: 10.1016/j.bioorg.2018.07.003. Epub Jul. 2, 2018. Author manuscript, 14 pages.
Yan et al., Regulating miRNA-21 Biogenesis by Bifunctional Small Molecules. J Am Chem Soc. Apr. 12, 2017;139(14):4987-4990. doi: 10.1021/jacs.7b00610. Epub Mar. 29, 2017. Author manuscript, 11 pages.
Yang et al., Mouse models for tumor metastasis. Methods Mol Biol. 2012;928:221-8. doi: 10.1007/978-1-62703-008-3_17. Author manuscript, 6 pages.

* cited by examiner

A

Targapremir-18a-CA-Biotin
(4-CA-Biotin)

Control-CA-Biotin
(Ctrl-CA-Biotin)

B

SEQUENCE LISTING

<160> NUMBER OF SEQ ID NOS: 43

<210> SEQ ID NO 1
<211> LENGTH: 23
<212> TYPE: DNA
<213> ORGANISM: Artificial sequence
<220> FEATURE:
<223> OTHER INFORMATION: Synthetic sequence

<400> SEQUENCE: 1
caaagtgctt acagtgcagg tag 23

<210> SEQ ID NO 2
<211> LENGTH: 23
<212> TYPE: DNA
<213> ORGANISM: Artificial sequence
<220> FEATURE:
<223> OTHER INFORMATION: Synthetic sequence

<400> SEQUENCE: 2
taaggtgcat ctagtgcaga tag 23

<210> SEQ ID NO 3
<211> LENGTH: 23
<212> TYPE: DNA
<213> ORGANISM: Artificial sequence
<220> FEATURE:
<223> OTHER INFORMATION: Synthetic sequence

<400> SEQUENCE: 3
tgtgcaaatc tatgcaaaac tga 23

<210> SEQ ID NO 4
<211> LENGTH: 23
<212> TYPE: DNA
<213> ORGANISM: Artificial sequence
<220> FEATURE:
<223> OTHER INFORMATION: Synthetic sequence

<400> SEQUENCE: 4
tgtgcaaatc catgcaaaac tga 23

-continued

<210> SEQ ID NO 5
<211> LENGTH: 23
<212> TYPE: DNA
<213> ORGANISM: Artificial sequence
<220> FEATURE:
<223> OTHER INFORMATION: Synthetic sequence

<400> SEQUENCE: 5
taaagtgctt atagtgcagg tag 23

<210> SEQ ID NO 6
<211> LENGTH: 22
<212> TYPE: DNA
<213> ORGANISM: Artificial sequence
<220> FEATURE:
<223> OTHER INFORMATION: Synthetic sequence

<400> SEQUENCE: 6
tattgcactt gtcccggcct gt 22

<210> SEQ ID NO 7
<211> LENGTH: 22
<212> TYPE: DNA
<213> ORGANISM: Artificial sequence
<220> FEATURE:
<223> OTHER INFORMATION: Synthetic sequence

<400> SEQUENCE: 7
tggagagaaa ggcagttcct ga 22

<210> SEQ ID NO 8
<211> LENGTH: 21
<212> TYPE: DNA
<213> ORGANISM: Artificial sequence
<220> FEATURE:
<223> OTHER INFORMATION: Synthetic sequence

<400> SEQUENCE: 8
taggccttta gatcacttaa a 21

<210> SEQ ID NO 9
<211> LENGTH: 21
<212> TYPE: DNA
<213> ORGANISM: Artificial sequence
<220> FEATURE:
<223> OTHER INFORMATION: Synthetic sequence

<400> SEQUENCE: 9
ctttttgcgg tctgggcttg c 21

<210> SEQ ID NO 10
<211> LENGTH: 21
<212> TYPE: DNA
<213> ORGANISM: Artificial sequence
<220> FEATURE:
<223> OTHER INFORMATION: Synthetic sequence

<400> SEQUENCE: 10
taccacaggg tagaaccacg g 21

<210> SEQ ID NO 11
<211> LENGTH: 22
<212> TYPE: DNA
<213> ORGANISM: Artificial sequence
<220> FEATURE:
<223> OTHER INFORMATION: Synthetic sequence

<400> SEQUENCE: 11
tctcccaacc cttgtaccag tg 22

<210> SEQ ID NO 12
<211> LENGTH: 23
<212> TYPE: DNA
<213> ORGANISM: Artificial sequence
<220> FEATURE:
<223> OTHER INFORMATION: Synthetic sequence

<400> SEQUENCE: 12
cccagtgttc agactacctg ttc 23

<210> SEQ ID NO 13
<211> LENGTH: 23
<212> TYPE: RNA
<213> ORGANISM: Artificial sequence
<220> FEATURE:
<223> OTHER INFORMATION: Synthetic sequence

<400> SEQUENCE: 13
uugaacuguu aagaaccacu gga 23

<210> SEQ ID NO 14
<211> LENGTH: 23
<212> TYPE: DNA
<213> ORGANISM: Artificial sequence
<220> FEATURE:
<223> OTHER INFORMATION: Synthetic sequence

<400> SEQUENCE: 14
agctacattg tctgctgggt ttc 23

<210> SEQ ID NO 15
<211> LENGTH: 22
<212> TYPE: DNA
<213> ORGANISM: Artificial sequence
<220> FEATURE:
<223> OTHER INFORMATION: Synthetic sequence

<400> SEQUENCE: 15
ggctggagcg agtgcagtgg tg 22

<210> SEQ ID NO 16
<211> LENGTH: 22
<212> TYPE: DNA
<213> ORGANISM: Artificial sequence
<220> FEATURE:
<223> OTHER INFORMATION: Synthetic sequence

<400> SEQUENCE: 16
catgctagga tagaaagaat gg 22

<210> SEQ ID NO 17
<211> LENGTH: 23
<212> TYPE: DNA
<213> ORGANISM: Artificial sequence
<220> FEATURE:
<223> OTHER INFORMATION: Synthetic sequence

<400> SEQUENCE: 17
tagtgagtta gagatgcaga gcc 23

<210> SEQ ID NO 18

<211> LENGTH: 24
<212> TYPE: DNA
<213> ORGANISM: Artificial sequence
<220> FEATURE:
<223> OTHER INFORMATION: Synthetic sequence

<400> SEQUENCE: 18
gaaaatgatg agtagtgact gatg 24

<210> SEQ ID NO 19
<211> LENGTH: 21
<212> TYPE: DNA
<213> ORGANISM: Artificial sequence
<220> FEATURE:
<223> OTHER INFORMATION: Synthetic sequence

<400> SEQUENCE: 19
tggtagacta tggaacgtag g 21

<210> SEQ ID NO 20
<211> LENGTH: 17
<212> TYPE: DNA
<213> ORGANISM: Artificial sequence
<220> FEATURE:
<223> OTHER INFORMATION: Synthetic sequence

<400> SEQUENCE: 20
tgagggagga gactgca 17

<210> SEQ ID NO 21
<211> LENGTH: 22
<212> TYPE: DNA
<213> ORGANISM: Artificial sequence
<220> FEATURE:
<223> OTHER INFORMATION: Synthetic sequence

<400> SEQUENCE: 21
agactgacgg ctggaggccc at 22

<210> SEQ ID NO 22
<211> LENGTH: 21
<212> TYPE: DNA
<213> ORGANISM: Artificial sequence
<220> FEATURE:
<223> OTHER INFORMATION: Synthetic sequence

<400> SEQUENCE: 22
gaccgagagg gcctcggctg t 21

<210> SEQ ID NO 23
<211> LENGTH: 17
<212> TYPE: DNA
<213> ORGANISM: Artificial sequence
<220> FEATURE:
<223> OTHER INFORMATION: Synthetic sequence

<400> SEQUENCE: 23
atggagaagg cttctga 17

<210> SEQ ID NO 24
<211> LENGTH: 21
<212> TYPE: DNA
<213> ORGANISM: Artificial sequence
<220> FEATURE:
<223> OTHER INFORMATION: Synthetic sequence

<400> SEQUENCE: 24
agctgtacct gaaaccaagc a 21

<210> SEQ ID NO 25
<211> LENGTH: 23
<212> TYPE: DNA
<213> ORGANISM: Artificial sequence
<220> FEATURE:
<223> OTHER INFORMATION: Synthetic sequence

<400> SEQUENCE: 25
tggccggatg ggacaggagg cat 23

<210> SEQ ID NO 26
<211> LENGTH: 22
<212> TYPE: DNA
<213> ORGANISM: Artificial sequence
<220> FEATURE:
<223> OTHER INFORMATION: Synthetic sequence

<400> SEQUENCE: 26
ttcggtatac tttgtgaatt gg 22

<210> SEQ ID NO 27
<211> LENGTH: 22
<212> TYPE: DNA
<213> ORGANISM: Artificial sequence
<220> FEATURE:
<223> OTHER INFORMATION: Synthetic sequence

<400> SEQUENCE: 27
tgaaacatac acgggaaacc tc 22

<210> SEQ ID NO 28
<211> LENGTH: 20
<212> TYPE: DNA
<213> ORGANISM: Artificial sequence
<220> FEATURE:
<223> OTHER INFORMATION: Synthetic sequence

<400> SEQUENCE: 28
ctgcaaaggg aagccctttc 20

<210> SEQ ID NO 29
<211> LENGTH: 21
<212> TYPE: DNA
<213> ORGANISM: Artificial sequence
<220> FEATURE:
<223> OTHER INFORMATION: Synthetic sequence

<400> SEQUENCE: 29
gcgacccact cttggtttcc a 21

<210> SEQ ID NO 30
<211> LENGTH: 20
<212> TYPE: DNA
<213> ORGANISM: Artificial sequence
<220> FEATURE:
<223> OTHER INFORMATION: Synthetic sequence

<400> SEQUENCE: 30
aaagtagctg taccatttgc 20

<210> SEQ ID NO 31
<211> LENGTH: 24
<212> TYPE: DNA

-continued

<213> ORGANISM: Artificial sequence
<220> FEATURE:
<223> OTHER INFORMATION: Synthetic sequence

<400> SEQUENCE: 31
tgcctgggtc tctggcctgc gcgt 24

<210> SEQ ID NO 32
<211> LENGTH: 21
<212> TYPE: DNA
<213> ORGANISM: Artificial sequence
<220> FEATURE:
<223> OTHER INFORMATION: Synthetic sequence

<400> SEQUENCE: 32
ttaatatcgg acaaccattg t 21

<210> SEQ ID NO 33
<211> LENGTH: 23
<212> TYPE: DNA
<213> ORGANISM: Artificial sequence
<220> FEATURE:
<223> OTHER INFORMATION: Synthetic sequence

<400> SEQUENCE: 33
tctttggtta tctagctgta tga 23

<210> SEQ ID NO 34
<211> LENGTH: 23
<212> TYPE: DNA
<213> ORGANISM: Artificial sequence
<220> FEATURE:
<223> OTHER INFORMATION: Synthetic sequence

<400> SEQUENCE: 34
acacgcaaat tcgtgaagcg ttc 23

<210> SEQ ID NO 35
<211> LENGTH: 20
<212> TYPE: DNA
<213> ORGANISM: Artificial sequence
<220> FEATURE:
<223> OTHER INFORMATION: Synthetic sequence

<400> SEQUENCE: 35
gtaacccgtt gaaccccatt 20

<210> SEQ ID NO 36
<211> LENGTH: 20
<212> TYPE: DNA
<213> ORGANISM: Artificial sequence
<220> FEATURE:
<223> OTHER INFORMATION: Synthetic sequence

<400> SEQUENCE: 36
ccatccaatc ggtagtagcg 20

<210> SEQ ID NO 37
<211> LENGTH: 42
<212> TYPE: DNA
<213> ORGANISM: Artificial sequence
<220> FEATURE:
<223> OTHER INFORMATION: Synthetic sequence

<400> SEQUENCE: 37
ggccggatcc taatacgact cactataggg agagggttta at 42

<210> SEQ ID NO 38
<211> LENGTH: 15
<212> TYPE: DNA
<213> ORGANISM: Artificial sequence
<220> FEATURE:
<223> OTHER INFORMATION: Synthetic sequence

<400> SEQUENCE: 38
ccttgcggat ccaat 15

<210> SEQ ID NO 39
<211> LENGTH: 38
<212> TYPE: DNA
<213> ORGANISM: Artificial sequence
<220> FEATURE:
<223> OTHER INFORMATION: Synthetic sequence

<400> SEQUENCE: 39
cctctctatg ggcagtcggt gatccttgcg gatccaat 38

<210> SEQ ID NO 40
<211> LENGTH: 58
<212> TYPE: DNA
<213> ORGANISM: Artificial sequence
<220> FEATURE:
<223> OTHER INFORMATION: Synthetic sequence
<220> FEATURE:
<221> NAME/KEY: misc_feature
<222> LOCATION: (31)..(40)
<223> OTHER INFORMATION: n is a, g, c, or t

<400> SEQUENCE: 40
ccatctcatc cctgcgtgtc tccgactcag nnnnnnnnnn gatgggagag ggtttaat 58

<210> SEQ ID NO 41
<211> LENGTH: 74
<212> TYPE: DNA
<213> ORGANISM: Artificial sequence
<220> FEATURE:
<223> OTHER INFORMATION: Synthetic sequence

<400> SEQUENCE: 41
gggtgttcta aggtgcatct agtgcagata gtgaagtaga ttagcatcta ctgccctaag 60
tgctccttct ggca 74

<210> SEQ ID NO 42
<211> LENGTH: 49
<212> TYPE: DNA
<213> ORGANISM: Artificial sequence
<220> FEATURE:
<223> OTHER INFORMATION: Synthetic sequence

<400> SEQUENCE: 42
ggccgaattc taatacgact cactatatct aaggtgcatc tagtgcaga 49

<210> SEQ ID NO 43
<211> LENGTH: 22
<212> TYPE: DNA
<213> ORGANISM: Artificial sequence
<220> FEATURE:
<223> OTHER INFORMATION: Synthetic sequence

<400> SEQUENCE: 43
tgctacaagt gccttcactg ca 22

DEFINING RNA-SMALL MOLECULE AFFINITY LANDSCAPES ENABLES DESIGN OF A SMALL MOLECULE INHIBITOR OF AN ONCOGENIC NON-CODING RNA

CROSS-REFERENCE TO RELATED APPLICATIONS

This application is a national stage filing under 35 U.S.C. § 371 of International Patent Application Serial No. PCT/US2021/032488, filed May 14, 2021 which claims priority under 35 U.S.C. § 119(e) to U.S. Provisional Patent Application No. 62/460,184, filed Feb. 17, 2017, the disclosure of each of which are incorporated herein by reference in their entireties.

STATEMENT OF GOVERNMENT SUPPORT

This invention was made with government support under R01-GM097455 awarded by the National Institutes of Health. The government has certain rights in the invention.

REFERENCE TO A SEQUENCE LISTING SUBMITTED AS A TEXT FILE VIA EFS-WEB

This application contains a Sequence Listing which has been submitted in ASCII format via EFS-Web and is hereby incorporated by reference in its entirety. Said ASCII copy, created on Dec. 6, 2022, is named U1202.70109US01-SEQ-WLC and is 8,813 bytes in size.

BACKGROUND

RNA has many essential functions in cells and thus is an important target for chemical probes or lead therapeutics. Developing RNA-directed chemical probes is challenging, however, due to a dearth of data describing the types of small molecules that bind RNA folds (motifs) selectively.[1,2] Although a small dataset, selective RNA motif-small molecule interactions have been used to inform the design of bioactive small molecules, including monomeric and modularly assembled ligands.[3-13] The latter compounds bind RNAs that have multiple targetable motifs that are separated by a specific distance.[6,8-13] In order to target the myriad of disease-causing RNAs in a cell using rational and predictable methods, much more data that describe selective interactions between small molecules and RNA motifs will be required as well as new high throughput tools and technologies to obtain them.

A library-vs.-library screen named Two-Dimensional Combinatorial Screening (2DCS) has proven to be a powerful method to identify selective RNA motif-small molecule binding partners in a high throughput fashion.[14] Although screening is rapid, downstream processing of the selected interactions, such as scoring affinity and selectivity, is laborious, requiring time-consuming binding assays. Previously, a theoretical approach was developed to compute scoring functions for 2DCS selections based on the statistical confidence of sub-features imparting binding affinity.[15] Since the models are not empirical, interactions that do not obey the model could have their affinities and selectivities mis-assigned.

SUMMARY

The invention provides, in various embodiments, a method of inhibiting production of microRNA miR-18a, in a prostate cancer cell, from the oncogenic microRNA (miR)-18a hairpin precursor of the miR-17-92 cluster, comprising contacting the cell with an effective amount or concentration of any one of compound 1

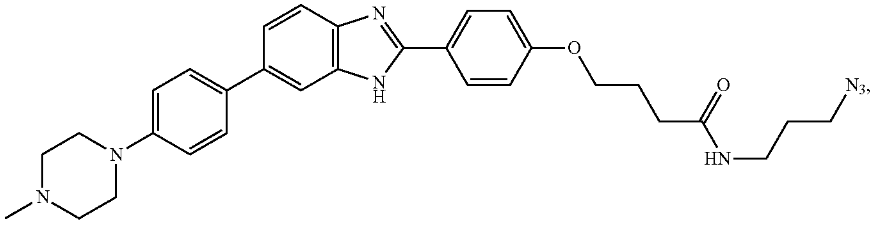 [SMILES: CN1CCN(c2ccc(-c3ccc4nc(-c5ccc(OCCCC(=O)NCCCN=[N+]=[N-])cc5)[nH]c4c3)cc2)CC1]

1 compound 2

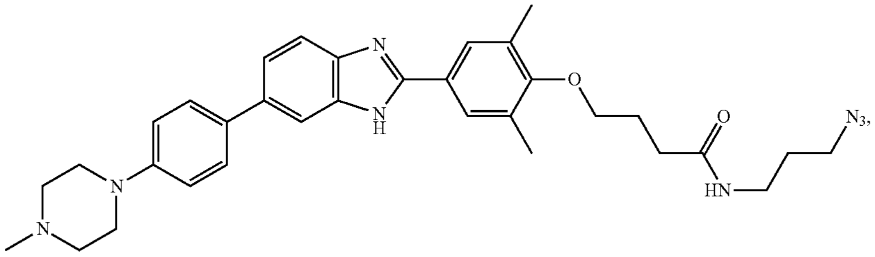 [SMILES: Cc1cc(-c2nc3ccc(-c4ccc(N5CCN(C)CC5)cc4)cc3[nH]2)cc(C)c1OCCCC(=O)NCCCN=[N+]=[N-]]

2

-continued compound 3,

3

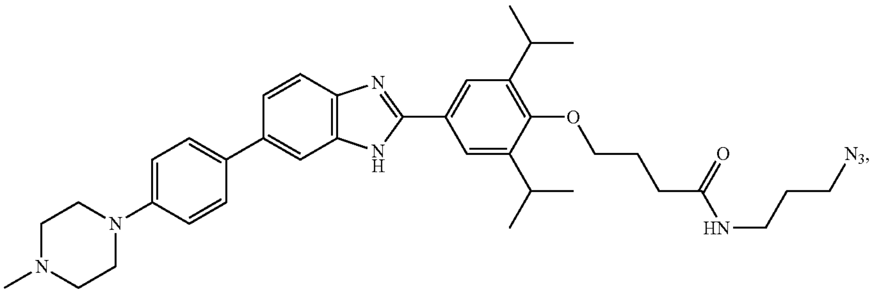 [SMILES: CC(C)c1cc(-c2nc3ccc(-c4ccc(N5CCN(C)CC5)cc4)cc3[nH]2)cc(C(C)C)c1OCCCC(=O)NCCCN=[N+]=[N-]]

or compound 4 (Targapremir-18a)

4

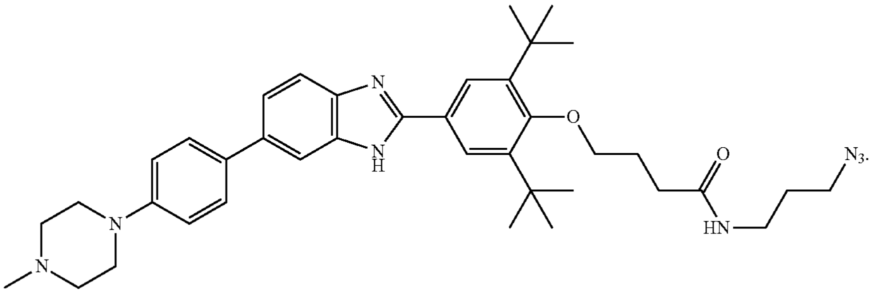 [SMILES: CN1CCN(c2ccc(-c3ccc4nc(-c5cc(C(C)(C)C)c(OCCCC(=O)NCCCN=[N+]=[N-])c(C(C)(C)C)c5)[nH]c4c3)cc2)CC1]

Targapremir-18a

For example, the compound of any of formula 1, 2, 3, or 4 (Targapremir-18a), administered to the prostate cancer cell further de-represses serine/threonine protein kinase 4 protein (STK4), and triggers apoptosis of the prostate cancer cell.

The invention further provides, in various embodiments, a method of treatment of prostate cancer, comprising administering to a mammal afflicted therewith an effective dose of any one of compound 1

1

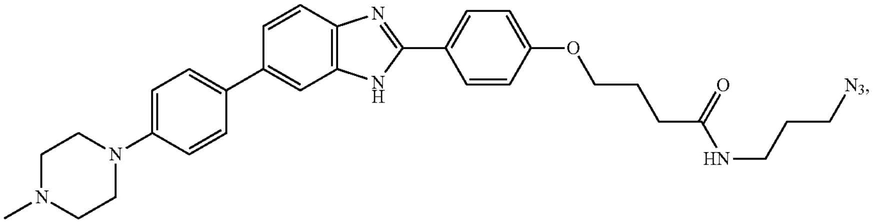

compound 2

2

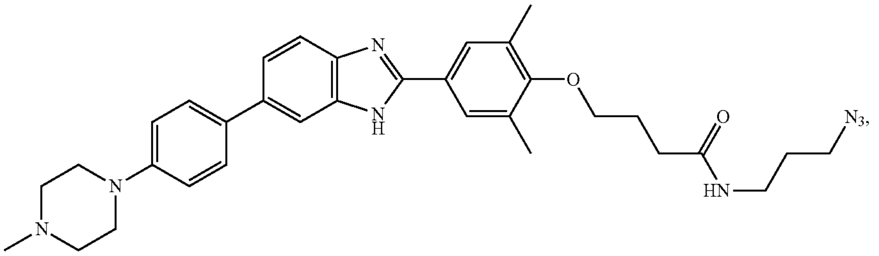

-continued compound 3,

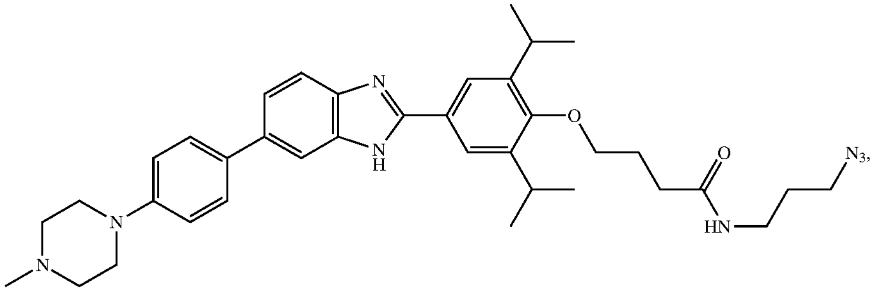

3 or compound 4 (Targapremir-18a)

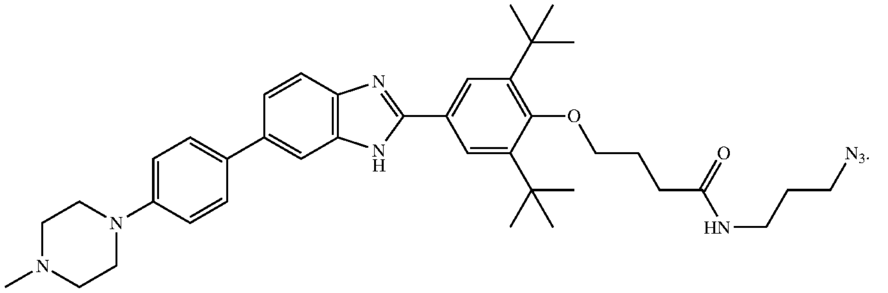

4

Targapremir-18a

The invention further provides, in various embodiments, a 2DCS/High Throughput Structure-Activity Relationships Through Sequencing (HiT-StARTS) method of identifying a ligand for binding a RNA internal loop from among a series of compounds, the ligand binding to one or more RNA internal loop motif molecules in a library thereof, comprising, 1) site-specifically immobilizing onto an alkyne-functionalized agarose microarray surface via a Cu-catalyzed Huisgen dipolar cycloaddition reaction, a corresponding set of small molecule candidate ligands, each with an azide tag for reaction with the alkyne; then,
2) contacting the microarray of site-specifically immobilized candidate ligands with a library of radiolabeled RNA internal loop segments each with a variable loop region, the library comprising a plurality of candidate RNA loop motifs therein; then,
3) identifying the ligands binding a selected set of the candidate RNA loop motifs; then,
4) harvesting the bound RNAs; then,
5) subjecting the bound RNAs to RT-PCR, including ligation of adapters for RNA sequencing; then,
6) obtaining the complete set of RNA sequences of bound RNAs; and
7) obtaining the complete set of RNA sequences of the starting RNA library; and then
8) complete the statistical analysis by comparing the results of steps 8) and 7), to provide $Z_{obs}$ values for each RNA from the library, using equations (1) and (2)

Equation (1)

$$\Phi = \frac{(n_1 p_1 + n_2 p_2)}{n1 + n2} \text{ and} \qquad (1)$$

-continued

Equation (2)

$$Z_{obs} = \frac{(p_1 - p_2)}{\sqrt{\Phi(1-\Phi)\left(\frac{1}{n_1} + \frac{1}{n_2}\right)}} \qquad (2)$$

where $n_1$ is the size of population 1 (number of reads for a selected RNA); $n_2$ is the size of population 2 (number of reads for the same RNA from sequencing of the starting library); $p_1$ is the observed proportion of population 1 (number of reads for a selected RNA divided by the total number of reads); $p_2$ is the observed proportion for population 2 (number of reads for the same RNA divided by the total number of reads in the starting library); then 9) calculate a Fitness Score by dividing the $Z_{obs}$ for a given RNA by the largest $Z_{obs}$ value emanating from step 8), wherein a higher Fitness Score identifies a RNA internal loop motif more suitable for binding a ligand.

To summarize sequential operations for the HiT-StARTS which is a statistical analysis (HiT-StARTS) that accounts for biases that occur during transcription, RT-PCR, and RNA-seq:

Step #1: A 2DCS selection is completed as described in steps 1-5 above, then, carrying out the following steps:

Step #2: Complete RNA-seq of bound RNAs from 2DCS selection

Step #3: Complete RNA-seq of starting RNA library

Step #4: Complete statistical analysis by comparing the results of 2 & 3 (pooled population comparison), which affords Zobs for each RNA from the library. The equations in the application are how a pooled population comparison is completed/Zobs is calculated.

Step #5: Zobs can be converted into a p-value (common statistical parameter) or in our case a Fitness Score. A Fitness Score is calculated by dividing the Zobs for a given RNA by the largest Zobs value emanating from #4. This is not something that has to be done, however.

The statistical analysis (HiT-StARTS) is important as it accounts for biases that occur during transcription, RT-PCR, and RNA-seq, obtained from the results of the known 2DCS selection procedure.

DETAILED DESCRIPTION

Here, we report an empirical method that rapidly defines binding landscapes, assigns RNA motif-small molecule scoring functions, and generates structure-activity relationships using data derived from next-generation sequencing (RNA-seq) from a 2DCS experiment and experimentally determined affinities. The approach, named High Throughput Structure-Activity Relationships Through Sequencing (HiT-StARTS), statistically analyzes a selection by computing the enrichment that a selected RNA motif has by comparison to the starting library in an RNA-seq experiment. HiT-StARTS is likely to have broad applications. For example, SELEX is often used to screen nucleic acid libraries to identify nucleic acids that bind a ligand.[14,16-18] Further, DNA can be used to encode small molecules that bind to a therapeutically important target.[19-21]

By using the results of 2DCS along with Inforna,[22] an informatics pipeline that mines RNA motif-small molecule interactions against RNA folds in the transcriptome, a small molecule was identified that could target nuclease-processing sites in the oncogenic non-coding microRNA (miR)-17-92 cluster. Application of this compound to cells inhibited processing of miR-18a precursor, de-repressed a silenced protein, and slowed growth and triggered apoptosis in prostate cancer cells. These studies have allowed for analysis of the types of RNAs that can be affected by small molecules, showing that targeting functional sites in an RNA and the expression of the target are important considerations.

Two-Dimensional Combinatorial Screening (2DCS) of an RNA-Focused Small Molecule Library.

We designed a series of small molecules (1-8; see FIG. 1 for structures, and the Examples for synthetic schemes and compound characterization) that might be privileged for selectively binding RNA. Each compound was appended with an azide tag such that they could be site-specifically immobilized onto alkyne-functionalized agarose microarray surfaces via Cu-catalyzed Huisgen dipolar cycloaddition reaction (FIG. 1)[14] The compounds have a benzimidazole core, which is privileged for RNA binding,[25-27] and also steric bulk such that the compounds do not bind DNA.[28,29] Part of our interest in further advancing compounds such as 1-8 is that a small, related benzimidazole compound selectively inhibited biogenesis of the oncogenic miR-96 precursor in breast cancer cells at low micromolar concentrations.[9] Thus, this chemotype appears privileged to target RNA in cells, the identification of which has been a significant challenge in RNA chemical biology.

Figure 1:
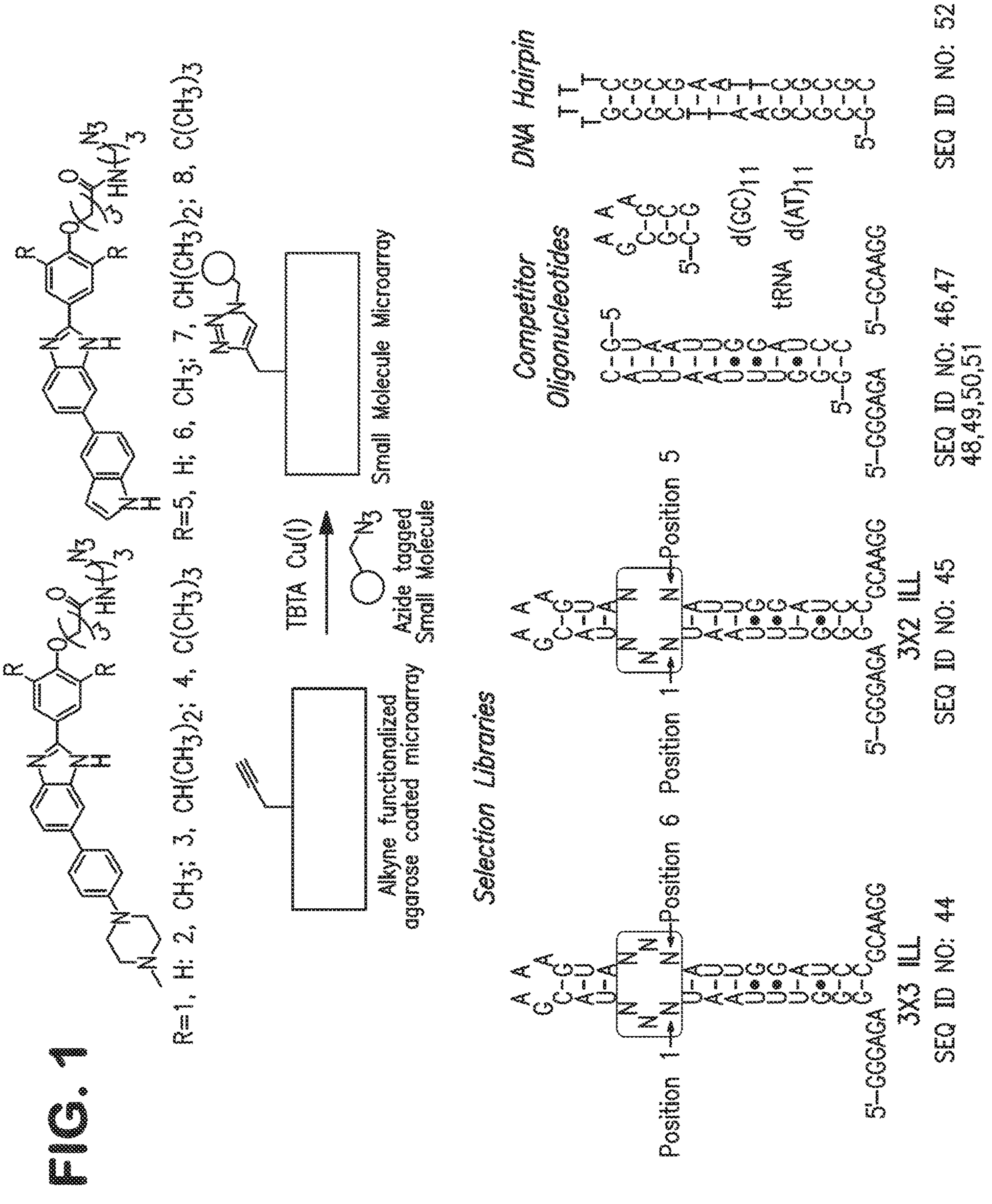
FIG. 1: Structures of the small molecules and oligonucleotides used in this study. Top, structures of the compounds tested for RNA binding and the Cu(I)-catalyzed "click chemistry" reaction (HDCR) to conjugate compounds onto the array surface. Bottom, secondary structures of the oligonucleotides.

The arrays were incubated with a $^{32}$P-labeled 3×3 nucleotide internal loop library (3×3 ILL), which contains 4,096 members, in the presence of excess unlabeled competitor nucleic acids (FIG. 1). The competitor RNA oligonucleotides mimic regions constant to all library members and restrict binding interactions to the randomized region. DNA oligonucleotides were also used in excess to ensure selective binding to RNA. The 3×3 ILL was chosen because the motifs it displays have a high probability of representation in a transcriptome. Thus, 32,768 unique interactions were probed simultaneously (8 small molecules×4,096 unique RNAs); if one considers the compounds, their densities, and the RNA library, then 163,840 interactions were probed (8 small molecules×5 compound densities×4,096 unique RNAs).

Initial analysis of the microarray data showed only compounds that contained a methylphenylpiperazine moiety (1-4) bound the RNA library under these stringent conditions.

Figure 2:
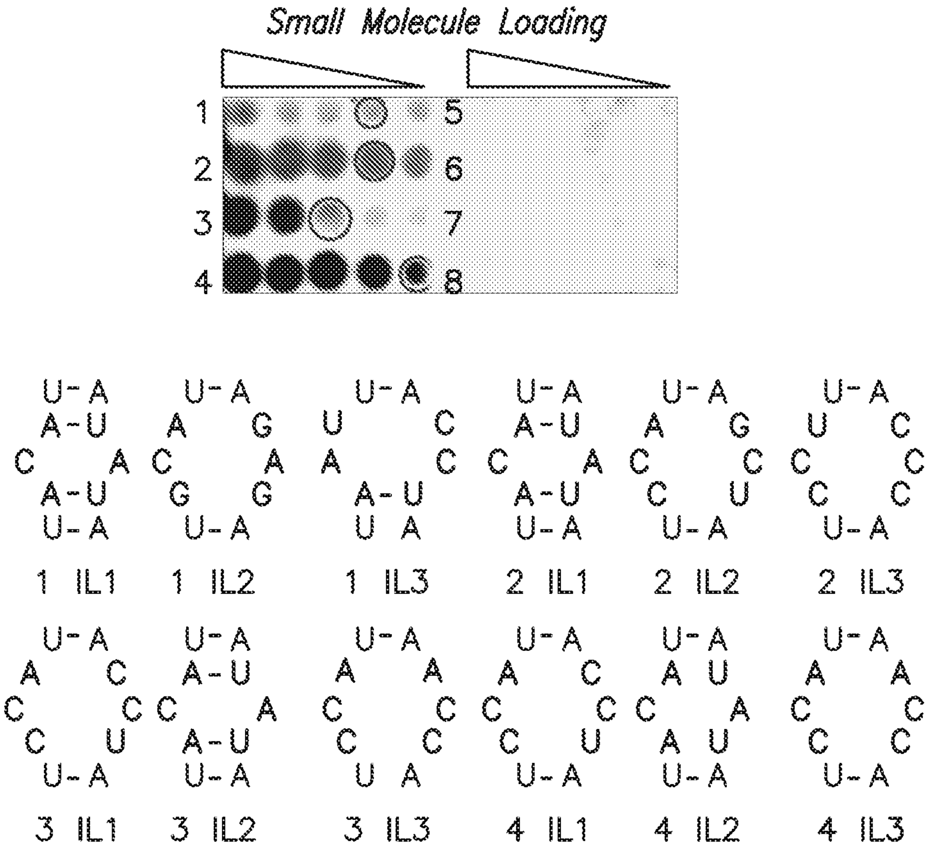
FIG. 2: An image of the 2DCS microarray from compounds 1-8 (Top) and the top three selected RNA motifs that bind to 1-4 (Bottom). No binding was observed to compounds 5-8. The number before "IL" (indicates internal loop) is the small molecule to which the RNA motifs were selected to bind. Circles indicate positions from which bound RNAs were isolated and subjected to RNA-seq. The amount of compound delivered to these positions corresponds to 560, 560, 840 and 370 picomoles for 1, 2, 3, and 4, respectively.

A few hundred picomoles of compound delivered to the surface were sufficient to detect binding and to select bound RNA motifs (FIG. 2). Furthermore, as the steric bulk of the functional groups on the phenyl ring bearing the R groups (H, methyl, isopropyl, and t-butyl) increased, the signal on the microarray increased (FIG. 2).

Bound RNA motifs for each compound were harvested from the array surface, amplified, and identified by using high throughput sequencing (RNA-seq). Highly abundant RNAs in the sequencing data were then subjected to binding measurements. Typically, those RNAs that were highly enriched bound to the small molecules with affinities ($K_d$s) that ranged from 1 to 10 μM (FIG. 2 and Table 1) while binding to the starting libraries was not saturable. These affinities are promising for binding RNA, as it has been difficult to acquire low micromolar affinity with compounds of this low molecular weight. In fact, RNAs that have undergone Darwinian evolution to bind small molecules, namely riboswitches, often bind their cognate ligand at micromolar to millimolar concentrations;[30-33] bioactive compounds that mimic riboswitch ligands bind with similar affinities.[30,34]

2DCS Identified RNA-Selective Small Molecule Ligands.

It has been difficult to identify compounds that are heterocyclic in nature that selectively recognize RNA over DNA.[5] Thus, to further gain insight into the selectivity of our RNA motif-small molecule interactions, we compared the measured affinities for selected RNA motifs to the affinities of the ligands for an AT-rich DNA hairpin, a common target of small molecules similar to those shown in FIG. 1. Compounds that bound 3×3 ILL (1-4), however, are different from DNA binders in many key elements that suggest selective binding to RNA is possible.[6] For example, 1-4 have a benzimidazole moiety, which binds RNA,[29] not a bis-benzimidazole moiety common to DNA binders. This alteration reduces DNA affinity because key stacking and hydrogen bonding interactions are not possible. Additional steric bulk was added to the compounds to ablate binding to base paired DNA as has been shown with even bis-benzimidazoles.[28] Indeed, binding studies showed that 1-4 did not bind the DNA hairpin (Table 1). Thus, the interactions selected via 2DCS are RNA-selective.

Analysis of Selection Data to Define Rapidly Accurate Scoring Functions.

One advantage of using next-generation sequencing to deconvolute selections is that millions of sequencing reads can be obtained. When the number of unique members of a starting library is much less than the number of reads acquired, there is high coverage and hence high confidence in the data output. Thus, we sought to leverage the large dataset generated for our 2DCS selections to develop models to rapidly assign binding landscapes. Such approaches would streamline such investigations, rapidly identify desired targets for small molecules, and determine if a small molecule has potential to discriminate effectively between desired and undesired targets. For example, a small molecule that binds tightly to an RNA that causes a disease, such as the expanded r(CUG) repeat that causes muscular dystrophy, but does not bind to the human A-site (an off-target) would be highly desirable. Such studies could preemptively eliminate non-specific compounds from further development.

We thus sought to utilize the results obtained from high throughput sequencing to develop an effective model to quickly identify the most avid binders from the population of selected RNA motifs. Previously, we developed a framework that utilized a binding model in which highly enriched sub-motifs within a given RNA structure (such as a GC step) were analyzed to compute a scoring function.[15] Because some interactions may not obey a theoretical model, we aimed to develop a model-free method to derive scoring functions. If successful, this approach could be generally applicable to any nucleic acid selection.

Using Frequency of Selected RNA Motifs to Score Binding.

We first analyzed the frequency of each selected RNA motif in the sequencing data. RNAs were ranked from the most frequently occurring (Frequency Rank=1) to the least frequently occurring (Frequency Rank=4,096).[37] We hypothesized that RNAs with a Frequency Rank of 1 would bind with higher affinity to its cognate small molecule than RNA motifs with greater Frequency Ranks, while RNAs at the end of the spectrum would not bind. To determine if this approach could indeed score affinities, we measured the binding of RNA motifs over a range of Frequency Rank values for compounds 1-4 (those that bind RNA in our 2DCS selection). In total we measured the affinities of 52 RNA-motif small molecule interactions.

Figure 3:
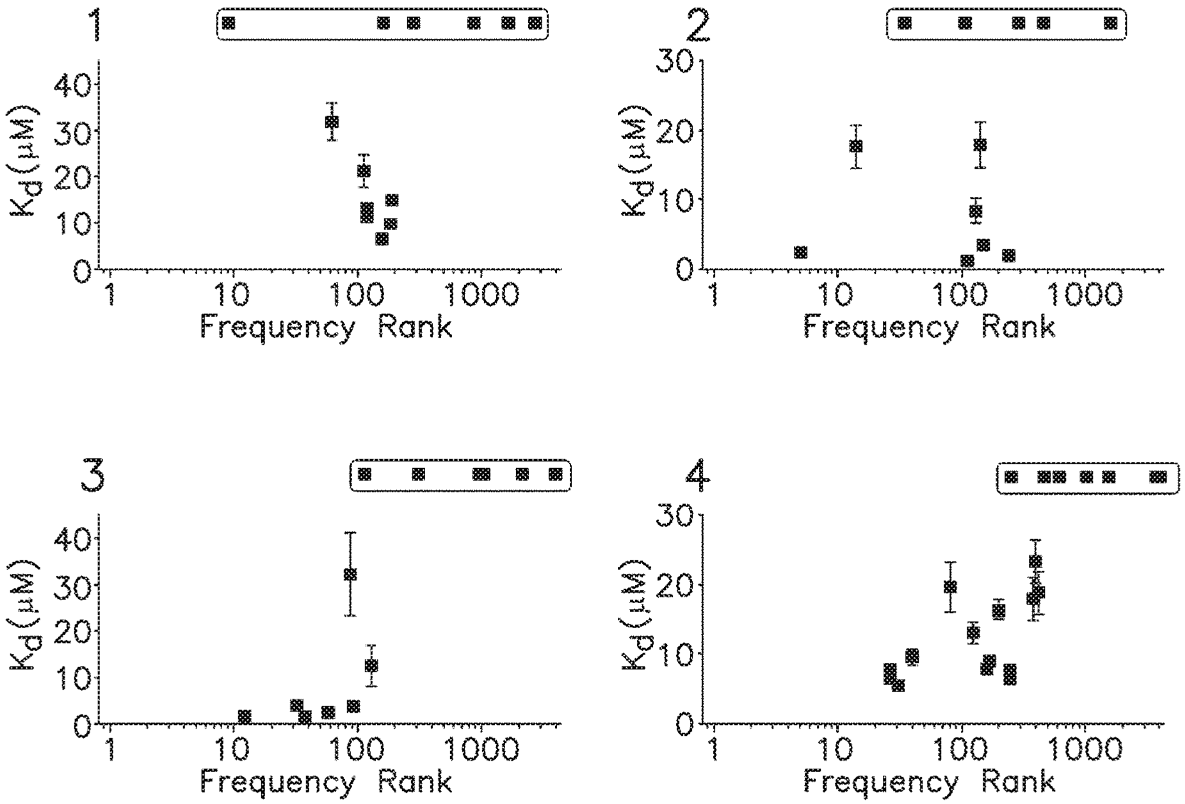
FIG. 3: Plots of Frequency Rank as a function of experimentally determined $K_d$ for compounds 1-4. RNAs were ranked from the most frequently occurring (Frequency Rank=1) to the least frequently occurring (Frequency Rank=4,096). Boxed data points are interactions that do not exhibit saturable binding.

As shown in FIG. 3, there was poor correlation between Frequency Rank and the affinity of the selected RNA motif-small molecule complexes. Previously, however, this approach was used to score the relative affinities of RNA-protein interactions.[37]

Using Statistical Analysis ($Z_{obs}$) of Selected RNA Motifs to Derive Scoring Functions and Structure-Activity Relationships.

Figure 4:
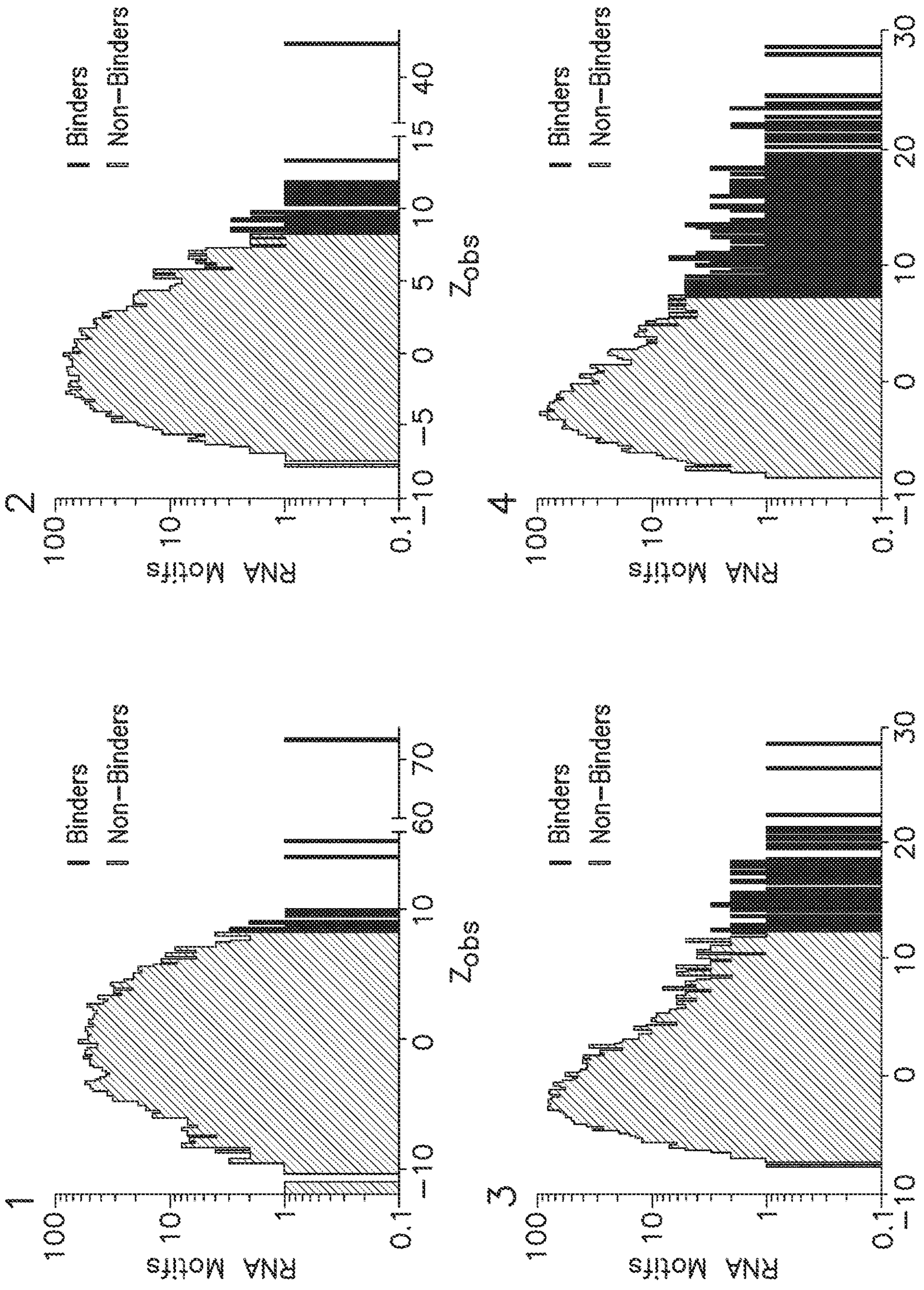
FIG. 4: A plot of the frequency of the selected RNA motifs as a function of $Z_{obs}$. Collectively, these data and the data presented in FIG. 5 show that avid binders are correlated with $Z_{obs}$. The signal on the microarray from 2DCS selections is directly proportional to the number of motifs with large, positive $Z_{obs}$ values.
Figure 5:
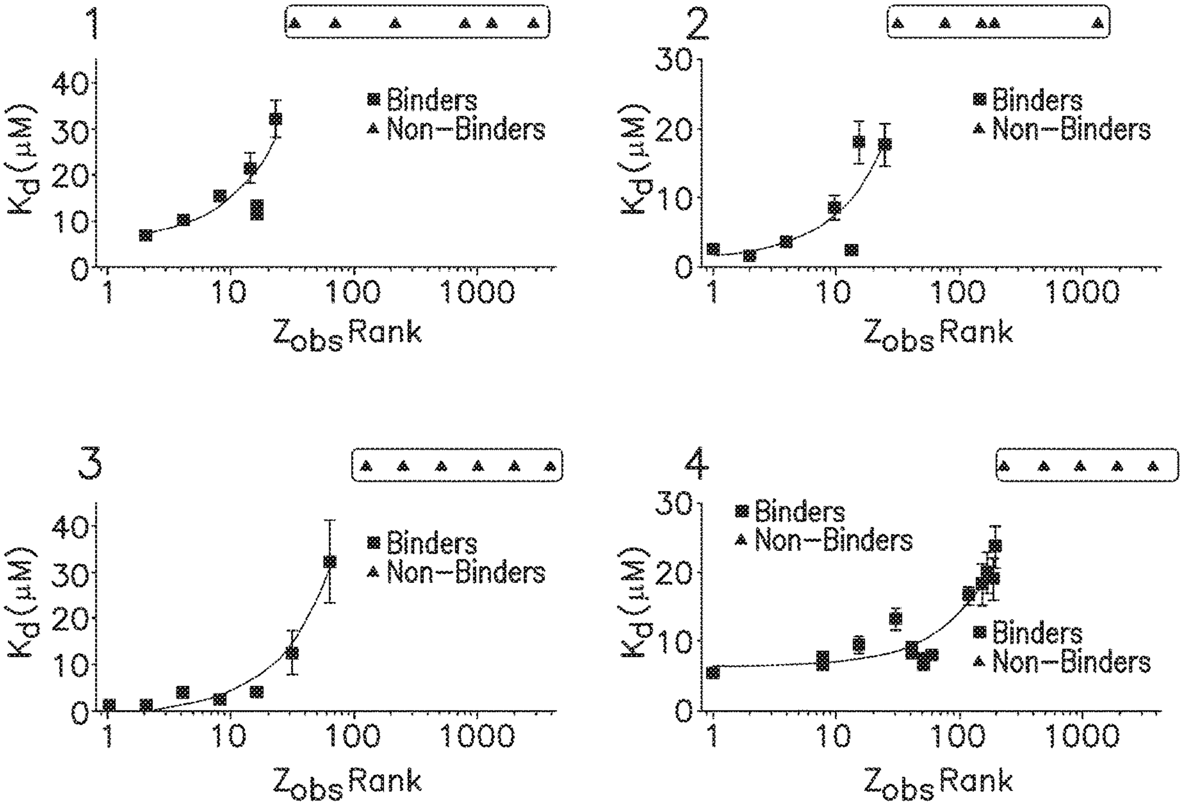
FIG. 5: Statistical analysis of sequencing data correlates well with affinity. A pooled population comparison (selected RNAs vs. the starting library) was used to afford $Z_{obs}$, a metric of statistical confidence. Each RNA was also assigned a $Z_{obs}$ Rank, ranging from 1 (greatest statistical confidence for avid binding; largest positive $Z_{obs}$ value) to 4,096 (greatest statistical confidence for not binding; largest negative $Z_{obs}$ value). Boxed data points are interactions that do not exhibit saturable binding.

Since it did not appear that a simple ranking of frequency provided accurate scoring of affinities, we applied a statistical approach of the present invention that we named High Throughput Structure-Activity Relationships Through Sequencing (HiT-StARTS) (FIGS. 4 & 5). The starting RNA motif library, 3×3 ILL, without selection, was subjected to high throughput sequencing to define biases that occur during transcription and sequencing. Such biases are unavoidable and caused by differences in the thermodynamic stability for individual RNA motifs, amongst others. That is, a pooled population comparison (equations 1 and 2) was used to compare the number of reads and its proportion of total reads for a given RNA in the selection sequencing data to the RNA's number of reads and its proportion of total reads from the starting library's sequencing data.

Equation (1)

$$\Phi = \frac{(n_1 p_1 + n_2 p_2)}{n1 + n2} \text{ and } \tag{1}$$

Equation (2)

$$Z_{obs} = \frac{(p_1 - p_2)}{\sqrt{\Phi(1-\Phi)\left(\frac{1}{n_1} + \frac{1}{n_2}\right)}} \tag{2}$$

where $n_1$ is the size of population 1 (number of reads for a selected RNA); $n_2$ is the size of population 2 (number of reads for the same RNA from sequencing of the starting library); $p_1$ is the observed proportion of population 1 (number of reads for a selected RNA divided by the total number of reads); $p_2$ is the observed proportion for population 2 (number of reads for the same RNA divided by the total number of reads in the starting library).

This comparison affords $Z_{obs}$, a metric of statistical confidence. $Z_{obs}$ can be converted to a two-tailed p-value, indicating the confidence that the null hypothesis (that there is no significant difference between the selected and starting RNA libraries) can be rejected. Note that $Z_{obs}$ can be positive or negative. A positive value indicates enrichment while a negative value indicates discrimination of the small molecule against a particular RNA. Akin to Frequency Rank, each RNA was also assigned a $Z_{obs}$ Rank, ranging from 1 (greatest statistical confidence for avid binding) to 4,096 (greatest statistical confidence for not binding).

Several features can be rapidly assessed from these data. First, there is a clear correlation between avidity of the RNA motif-small molecule interaction and $Z_{obs}$ Rank and $Z_{obs}$ (Table 1 and FIGS. 4 & 5). Motifs with $Z_{obs} \geq 8$ ($p<0.0001$) bind avidly to compounds 1 and 2; binding affinity is conferred by a $Z_{obs} \geq 12$ ($p<0.0001$) and $\geq 7$ ($p<0.0001$) for compounds 3 and 4, respectively. By using these assignments, we can estimate the number of RNA motifs that bound avidly to each of the small molecules: 23, 26, 64, and 215 RNA motifs for 1, 2, 3, and 4, respectively (Table 1 and FIG. 4). Thus, the higher signal on the array (FIG. 2) is a function of the number of RNA motifs that bind each ligand rather than a function of binding affinity.

Additionally, $Z_{obs}$ Rank (and by analogy $Z_{obs}$) can also be used to estimate the affinities of binding interactions (FIG. 5). Single exponential curves with an asymptote defined a correlation between $Z_{obs}$ and experimentally determined $K_d$ for each compound and its cognate RNA motifs. In all cases, there is excellent correlation with R values ranging from 0.86 to 0.96. These scoring functions can provide a means to rapidly profile small molecules for binding to an "on-" and "off-" targets, as mentioned above. $Z_{obs}$ values were normalized to the most statistically significant RNA binder (100% Fitness) to afford Fitness Scores.

We also determined the minimal fold coverage of the starting and selected RNA libraries in RNA-seq data required to afford accurate scoring functions (Table 2). A strong correlation ($R \sim 0.8$) is observed when both libraries have at least 24-fold coverage. Correlations ($R>0.5$) were observed with as little as 6-fold coverage of the starting library and 12-fold coverage of the selected library. Taken together, HiT-StARTS can rapidly identify interactions that are high affinity and selective (by comparing $Z_{obs}$ Rank for a given RNA for all four compounds), which are not predicted well by Frequency Rank. Additionally, the HiT-StARTS approach is able to discriminate between affinities, including those that differ by as little as 2-fold; however, the empirical relationship between $Z_{obs}$ and affinity can affect the sensitivity of these predictions. As seen in FIG. 5, the prediction is more sensitive to differences in affinity as the slope of the curve fit line increases.

HiT-StARTS Applied to Other RNA Motif Libraries.

To test the general applicability of these approaches to other RNA motif libraries, we used 2DCS to select RNA motifs derived from a 3×2 internal loop library (3×2 ILL) that bind to small molecules 1-8. This secondary structural motif displays asymmetric internal loops and bulges, the latter of which is under-represented amongst known RNA motif-small molecule interactions yet are highly prevalent in functional (Drosha and Dicer processing) sites in miRNA precursors[38] As was observed in selections with the 3×3 ILL, only compounds 1-4 bind members of the RNA library. HiT-StARTS analysis of the 2DCS experiments and subsequent binding analyses of the selected interactions showed that the features identified for 3×3 ILL were also found when using 3×2 ILL. That is, selective binders have $Z_{obs}>8$ ($p<0.0001$) and relative $Z_{obs}$ defined a scoring function for the selected RNA motif-small molecule interactions.

Identification of Biologically Important RNAs that can be Targeted.

The results of HiT-StARTS were used in conjunction with Inforna to identify RNA targets in the transcriptome that could be drugged with small molecule-RNA motif partners identified. Inforna mines information defining RNA motif-small molecule binding interactions to identify RNAs with targetable motifs.[9,22] This approach to chemical probe discovery could be considered target agnostic because the output of 2DCS is used to infer the preferred target of the small molecule. In particular, we focused on microRNAs (miRNAs) associated with disease that have targetable motifs in Dicer or Drosha processing sites, as defined by HiT-StARTS. A myriad of previous studies have shown that small molecules can inhibit miRNA precursor processing by binding to nuclease processing sites, with affinities ranging from nM to mid- to -high μM.[9,39-42]

Figure 6:
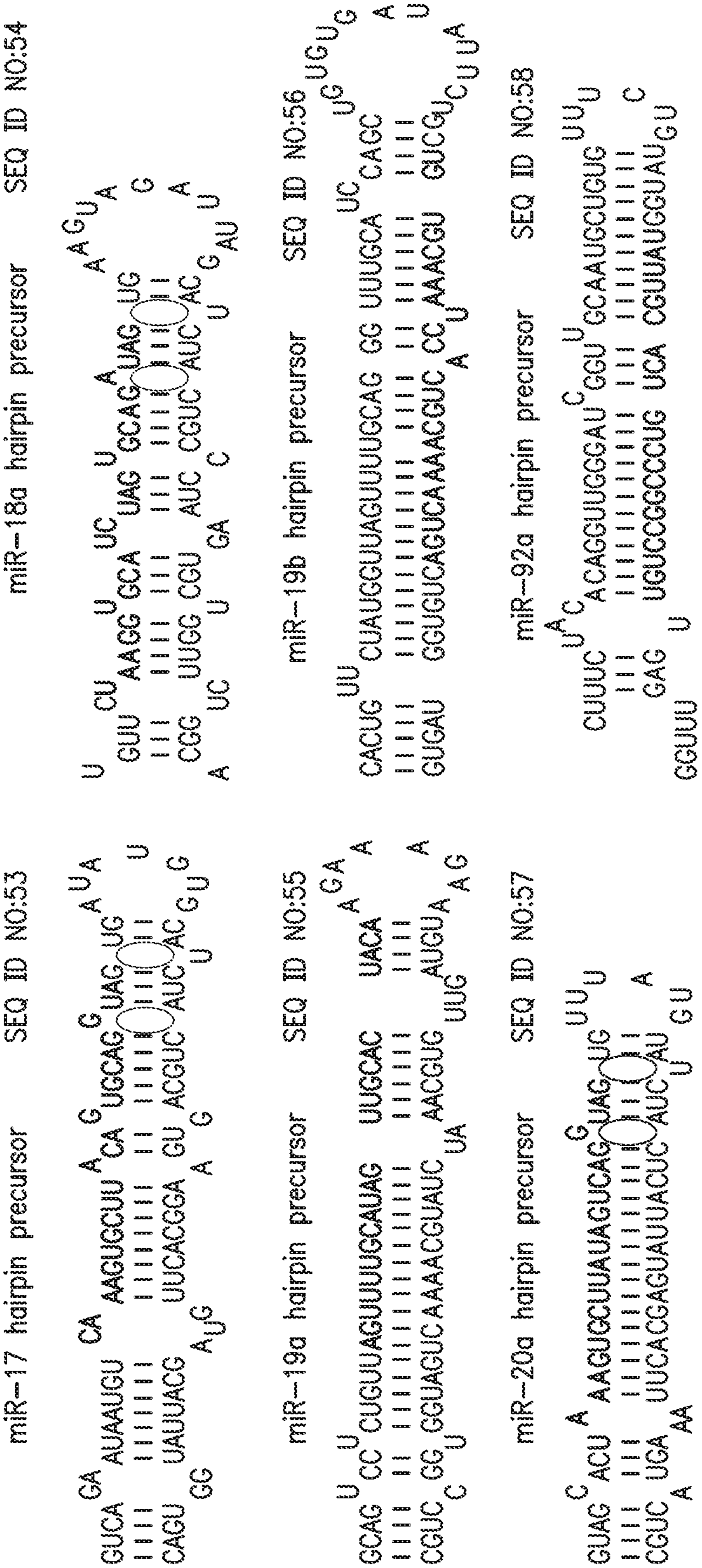
FIG. 6: Secondary structures of miR-17, -18a, -19a, -19b and -92a hairpin precursors. Mature miRNAs are indicated with red letters and binding sites for 4 are indicated with blue circles.
Figure 7:
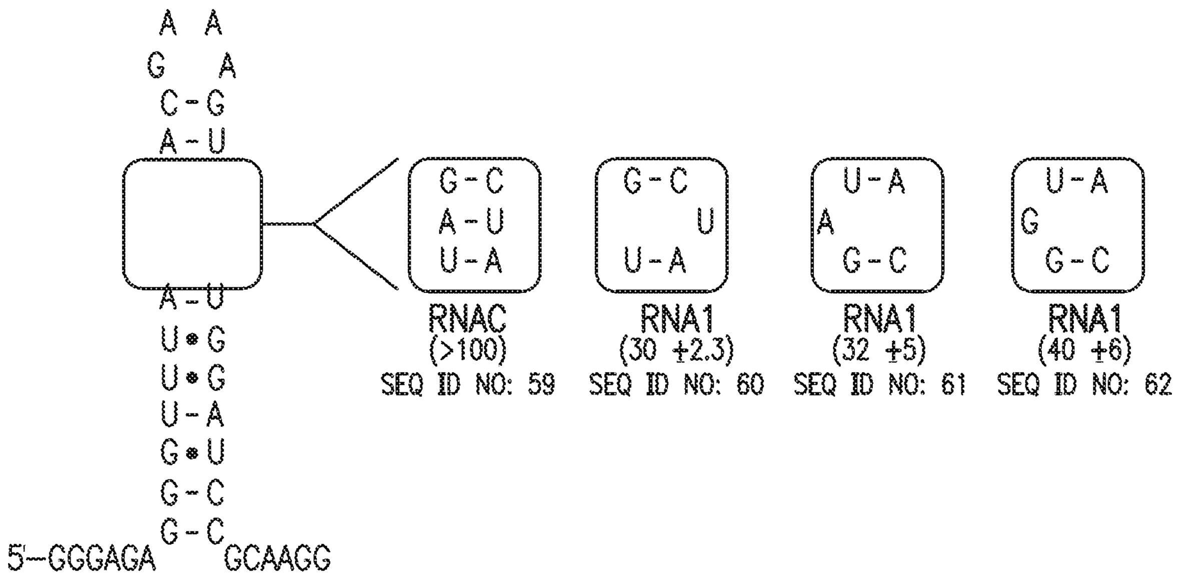
FIG. 7: Secondary structures of the nucleic acids to which the binding of small molecule 4 was assessed. RNAC is a control RNA that does not contain target sites. RNA1 contains the U bulge present in the Dicer processing site common to miR-17, -18a and -20a. RNA2 contains the A bulge that is present in miR-18a. RNA3 contains the G bulge present in miR-17 and miR-20a. Binding affinities ($K_d$'s) are indicated in parentheses and are reported in micromolar.

These studies identified that compound 4 bound with 100% Fitness to the 5' G_U/3'CUA (one nucleotide U bulge) that is present in the Dicer processing sites of three microRNAs (miRNAs) in the oncogenic miR-17-92 cluster (contains six mature miRNAs),[43] miR-17, -18a, and -20a. That is, of all RNA motifs present in the 3×2 ILL, 5'G_U/3'CUA is the highest affinity. Indeed, four most fit RNAs from the 2DCS selection of 4 contain U bulges (Figure S-62). Further, other highly fit bulges for compound 4 include 5'GAU/3'C_A (91% Fitness), an A bulge present in Dicer processing site of pre-miR-18a and 5'GGU/3'C_A (78% Fitness), a G bulge present in the Dicer processing sites of pre-miR-17 and pre-miR-20a (FIG. 6). The binding affinity of 4 for RNAs containing these three bulges was measured (FIG. 7).

These studies showed that 4 bound to the 5'G_U/3'CUA bulge common to the Dicer processing sites in miR-17, -18a and -20a (RNA1, FIG. 7) with a $K_d$ of 30±2 μM. Mutation of the U bulge to an AU pair (RNAC) eliminates binding ($K_d$>100 μM). Likewise, 4 binds the A bulge present in the miR-18a precursor (RNA2) with a $K_d$ of 32±5 μM and the G bulge present in the miR-17 and miR-20a precursors (RNA3) with a $K_d$ of 40±6 μM, in agreement with predictions by HiT-StARTS. No saturable binding was observed to the motifs in the Dicer sites of miR-19a, miR-19b, or miR-92a. (Notably, the dye itself does not contribute to binding affinity, as determined by competitive binding assays with 4-FL and 4 (Table S2) in agreement with previous observations with other small molecule-fluorescein conjugates.[9,29])

Small Molecules Identified by Inforna Inhibit Processing of miRNAs in the Oncogenic miR-17-92 Cluster.

Figure 8:
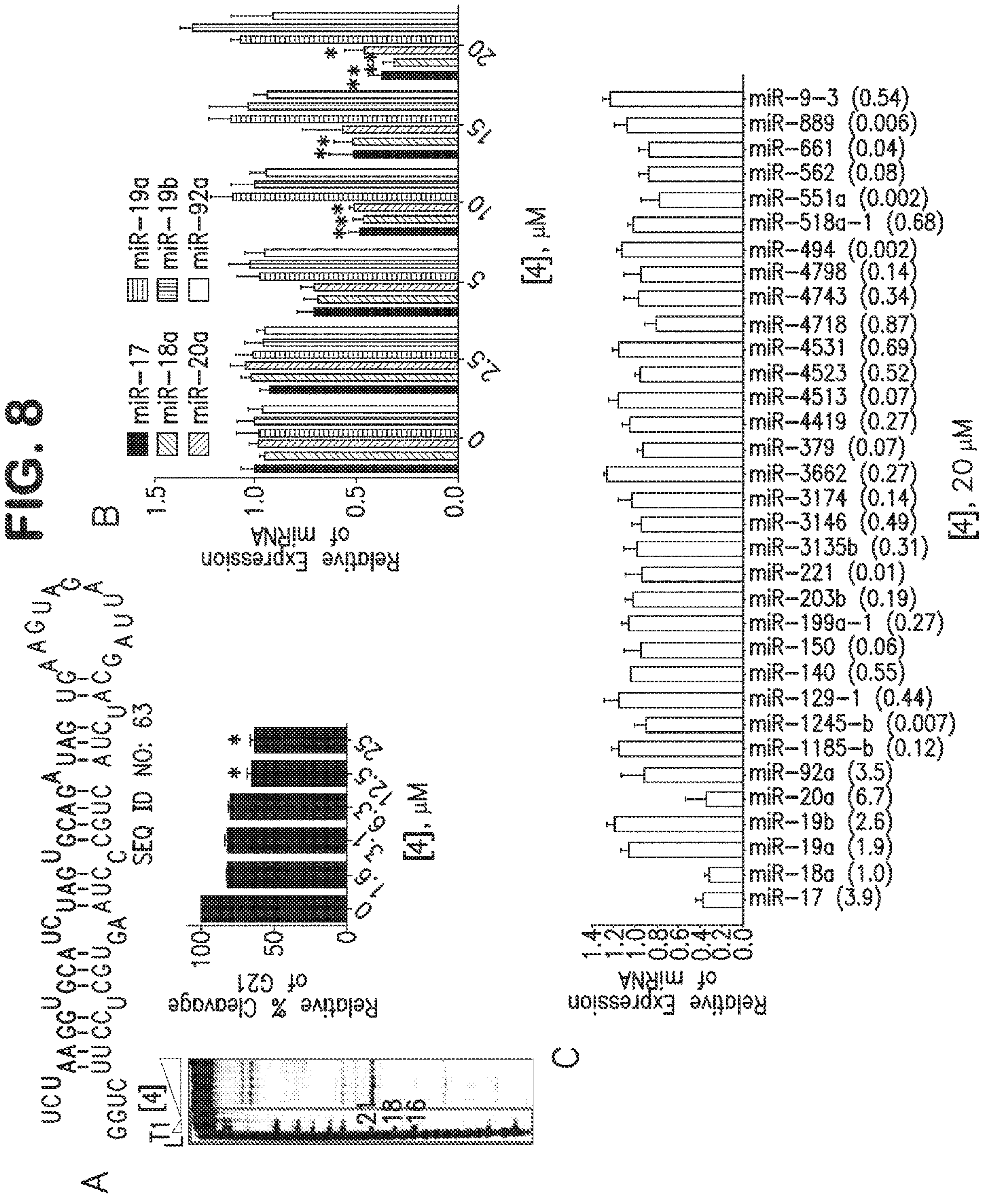
FIG. 8: Effect of 4 on the biogenesis of the miR-17-92 cluster in DU145 prostate cancer cells. A, 4 inhibits in vitro Dicer processing of pre-miR-18a. Lane L indicates a hydrolysis ladder. Lane T1 indicates cleavage by nuclease T1 under denaturing conditions (cleaves G's). B, Effect of 4 on mature miR-17, -18a, -19a, -19b, -20a and -92a in DU145 cells. C, Profiling of mature miRNAs levels in DU145 cells that contain potential binding sites for 4. The value indicated in parentheses is the normalized expression level, as compared to miR-18a in untreated cells. *, $p<0.05$ and **, $p<0.01$ as determined by a two-tailed Student t-test.

Initial studies were completed in vitro to determine if compound 4 (Targapremir-18a) inhibits Dicer processing of each miRNA separately in the miR-17-92 cluster using radioactively labeled RNA (FIG. 8A). Indeed, the compound inhibited Dicer processing of pre-miR-17, -18a, and -20 at low micromolar concentrations but had no effect on the processing of pre-miR-19a and pre-miR-19b (FIG. 8A and Figures S-58-S-62), as expected from HiT-StARTS analysis. Thus, inhibition of Dicer processing by 4 is selective for miR-17, -18a, and -20a and non-selective inhibition of Dicer processing is not observed.

Interestingly, both miR-18a and miR-20 are over-expressed in prostate cancer.[44-45] Thus, the effect of 4 on processing of the miR-17-92 cluster was studied in DU145 prostate cancer cells. In particular, the mature levels of each miRNA in the cluster were studied by RT-qPCR. In agreement with our in vitro Dicer processing studies (FIG. 8A and Figures S-58-S-62), 4 decreases the amount of mature miR-17, -18a, and -20a at low micromolar concentrations with an $IC_{50}$ of ~10 □M, but has no effect on miR-19a, -19b, and -92a (FIG. 8B).

We further probed the selectivity of 4 by studying its effect on levels of other mature miRNAs (FIG. 8C) and on pre-miR-17, -18a and -20a. We identified miRNAs with potential binding sites for 4, as determined by HiT-StARTS, using a database of RNA folds in the human miRNA transcriptome,[38] including the 5'G_U/3'CUA bulge common to the Dicer processing sites in miR-17, -18a and -20a (n=33). The potential binding sites for 4 can occur anywhere in the miRNA; that is, they were not confined to Drosha or Dicer processing sites. Other miRNAs that contain the 5'G_U/3'CUA motif have a much lower expression level than miR-17, miR-18a, and miR-20. Studying these RNAs could allow assessment of influence of expression level on compound potency and selectivity, an important consideration in RNA targeting that has largely gone unaddressed.

Interestingly, 4 has no statistically significant effect on the levels of any of the 33 mature miRNAs studied (FIG. 8C). These results suggest: (i) the small molecule must bind to a functional (processing) site to inhibit miRNA biogenesis; and (ii) the miRNA's abundance in cells influences how productive an interaction with a small molecule will be. Collectively, it appears that it is easier to target and inhibit the biogenesis of highly expressed miRNAs than the ones that are of lower expression. Such effects have been well-documented in the protein-targeting community but until now have not been studied in RNA targeting endeavors.

Addition of 4 Increase STK4 Expression.

A previous study has shown that miR-18a represses serine/threonine protein kinase 4 (STK4) protein, a tumor suppressor, in prostate cancer cells and promotes tumorigenesis.[45] Thus, we studied the ability of compound 4 to de-repress STK4 and trigger apoptosis. Treatment of DU145 cells with 20 μM of 4 increases levels of STK4 by 2.5-fold (FIG. 9A).

Figure 9:
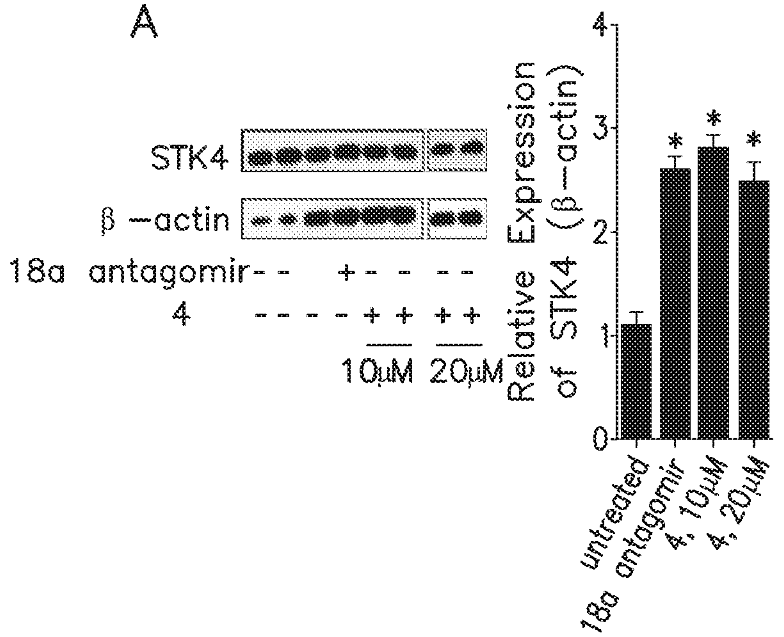
FIG. 9: Inhibition of miR-18a biogenesis by 4 de-represses a downstream protein and triggers apoptosis. A, Effect of 4 on STK4 protein expression, a direct target of miR-18a. B, Ability of 4 (10 μM and 20 μM) and a miR-18a antagomir (50 nM) to trigger apoptosis. *, $p<0.05$ and **, $p<0.01$, as determined by a two-tailed Student t-test.
Figure 9:
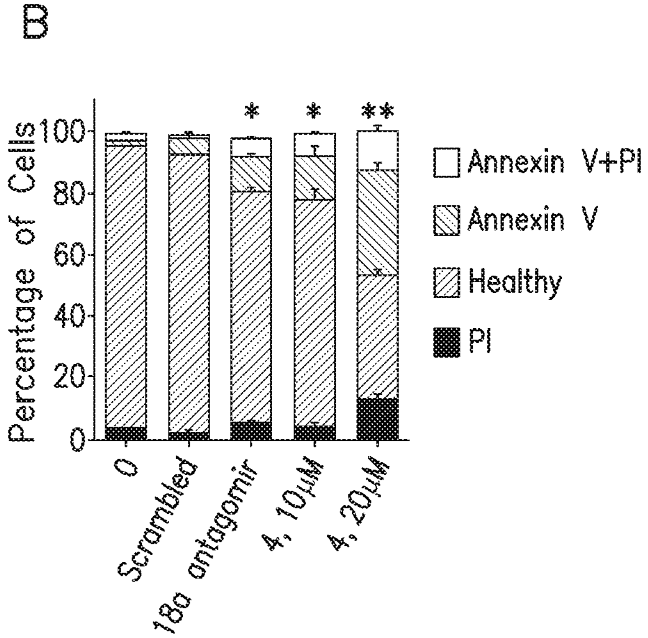

Further, inhibition of miR-18a biogenesis and de-repression of STK4 triggers apoptosis as assessed by Annexin V/PI staining (FIG. 9B). Although the most common route to modulate protein expression is to inhibit them directly, here we show it is possible to increase protein expression by targeting non-coding RNAs that repress their production.

Profiling the Target Selectivity of 4 by Using Chemical Cross-Linking and Isolation by Pull Down (Chem-CLIP).

Figure 10:
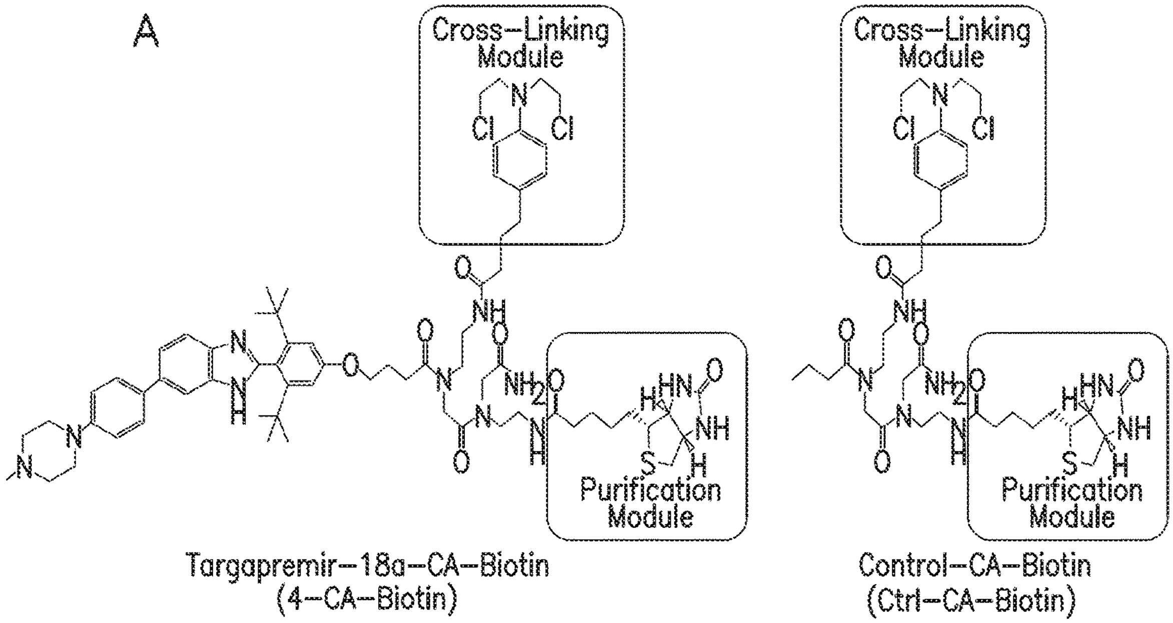
FIG. 10: Chem-CLIP to study small molecule engagement of pre-miR-18a by 4. A, Structure of 4-CA-Biotin and Ctrl-CA-Biotin, a control compound that lacks the RNA-binding module. B, In vitro assessment of 4-CA-Biotin and Ctrl-CA-Biotin for reacting with pre-miR-18a. C, Top, Chem-CLIP profiling in DU145 cells with 4-CA-Biotin. Bottom, Chem-CLIP profiling in DU145 cells with Ctrl-CA-Biotin. *, $p<0.05$ and **, $p<0.01$, as determined by a two-tailed Student t-test.
Figure 10:
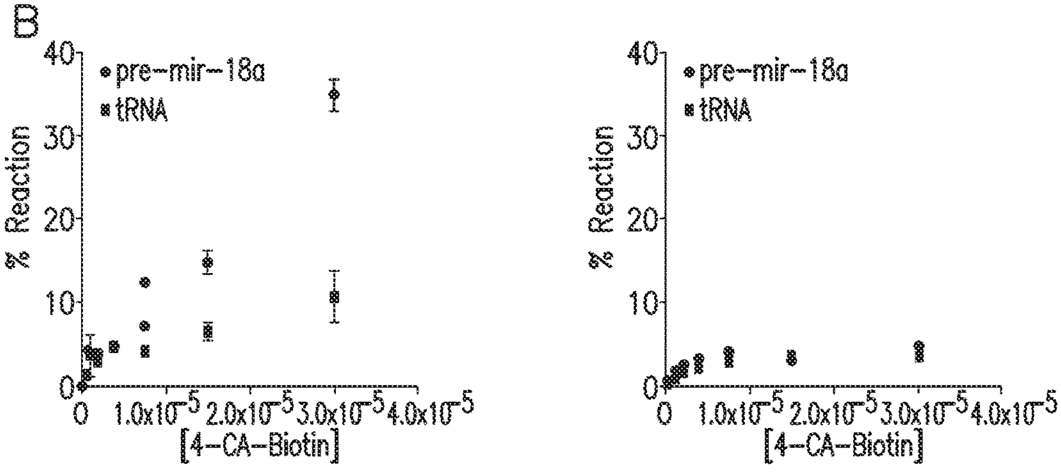
Figure 10:
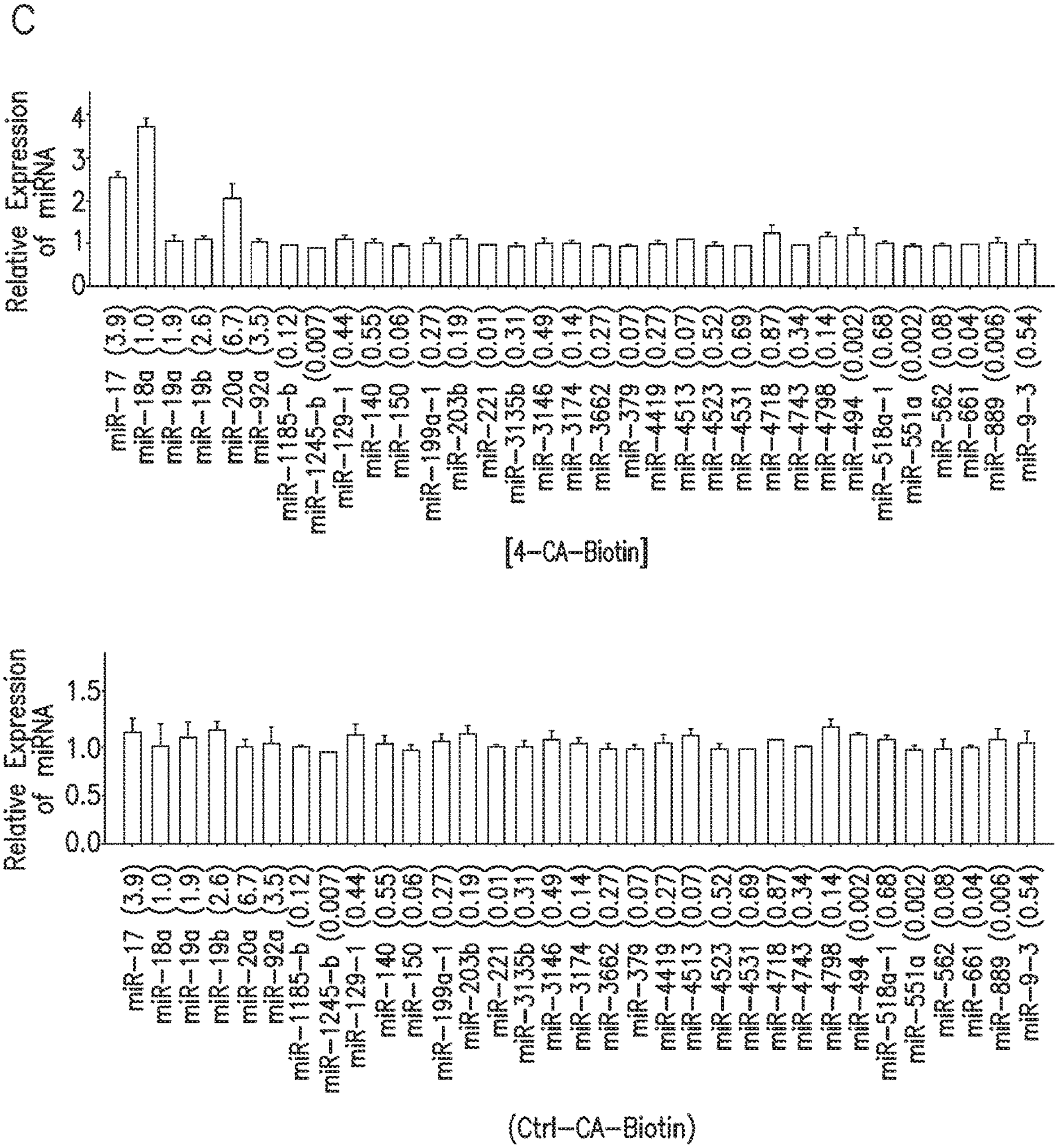

We previously developed a method to study the cellular targets of a small molecule called Chemical Cross-Linking and Isolation by Pull Down (Chem-CLIP).[46,47] In Chem-CLIP, a small molecule is appended with a cross-linking module that reacts with nucleic acids and a purification module to allow for the facile isolation of the small molecule's cellular targets. Thus, 4 was appended with chlorambucil (cross-linking module; CA) and biotin (purification module) to afford 4-CA-Biotin. We first studied the reaction of 4-CA-Biotin with pre-miR-18a in vitro and compared it to the reaction of the compound with tRNA. As expected, 4-CA-Biotin reacts to a greater extent with pre-miR-18a (FIG. 10B). The selectivity of 4-CA-Biotin was then studied in cellular lysates via RT-qPCR by calculating the enrichment of the target of interest in the pulled-down fraction. Enrichment was studied for the 33 miRNAs with potential binding sites for 4 as described above. Incubating 10 μM of 4 with DU145 cell lysate and quantification of the isolated targets showed a ~4-fold enrichment of pre-miR-18a and ~2-fold enrichment of pre-miR-17 and pre-miR-20a (FIG. 10C). There was no enrichment of any of the other miRNAs studied (FIG. 10C).

IMPLICATIONS AND CONCLUSIONS

The HiT-StARTS approach may be general for many types of library screens that use nucleic acid sequencing for de-convolution, provided that biases in the starting library can also be obtained by sequencing with sufficient fold coverage. At present, 2DCS, with the relatively small number of nucleic acid sequences in the starting library (we have employed libraries with up to 16,384 members) and DNA-encoded small molecule libraries are ideal applications of HiT-StARTS. The approach might be applicable for SELEX or phage display, as long as the starting libraries are small enough such that they can be sequenced with several fold coverage. It is likely, however, that as sequencing technologies advance and the number of sequence reads that can be completed in a single study increases, HiT-StARTS will be more broadly applicable. Furthermore, the selected RNA motif-small molecule binding partners could be developed into lead compounds that target RNA. This has been demonstrated for a first-in-class small molecule that affects the oncogenic miR-17-92 cluster.

TABLE 1

Global analysis of selected RNA motif-small molecule interactions. $K_d$'s are reported in μM.

| Compound | Range of $Z_{obs}$ for Binders | Number of Binders | Average $K_d$ of Selected RNA Binders | $K_d$ to DNA Hairpin |
|---|---|---|---|---|
| 1 | 8-72 | 23 | 16 ± 9 | >>100 |
| 2 | 8-44 | 26 | 7 ± 5 | >>100 |
| 3 | 12-29 | 64 | 8 ± 4 | >>100 |
| 4 | 7-29 | 215 | 11 ± 2 | >>100 |

TABLE 2

Goodness of fit (R-values) for scoring functions relative to the coverage of the sequencing data.

| Coverage of | Coverage of Starting Library | | | |
|---|---|---|---|---|
| Selected Library | 6-fold | 12-fold | 24-fold | 30-fold |
| 6-fold | 0.46 | 0.58 | 0.58 | 0.67 |
| 12-fold | 0.58 | 0.71 | 0.74 | 0.79 |
| 24-fold | 0.58 | 0.67 | 0.82 | 0.93 |
| 30-fold | 0.66 | 0.76 | 0.92 | 0.93 |

TABLE 3

Sequences of primers used for qRT-PCR.

| | |
|---|---|
| hsa-miR-17 SEQ ID NO: 1 | CAAAGTGCTTACAGTGCAGGTAG |
| hsa-miR-18a SEQ ID NO: 2 | TAAGGTGCATCTAGTGCAGATAG |
| hsa-miR-19a SEQ ID NO: 3 | TGTGCAAATCTATGCAAAACTGA |
| hsa-miR-19b SEQ ID NO: 4 | TGTGCAAATCCATGCAAAACTGA |
| hsa-miR-20a SEQ ID NO: 5 | TAAAGTGCTTATAGTGCAGGTAG |
| hsa-miR-92a SEQ ID NO: 6 | TATTGCACTTGTCCCGGCCTGT |
| hsa-miR-185b SEQ ID NO: 7 | TGGAGAGAAAGGCAGTTCCTGA |
| hsa-miR-1245b SEQ ID NO: 8 | TAGGCCTTTAGATCACTTAAA |
| hsa-miR-129-1 SEQ ID NO: 9 | CTTTTTGCGGTCTGGGCTTGC |
| hsa-miR-140: SEQ ID NO: 10 | TACCACAGGGTAGAACCACGG |
| hsa-miR-150 SEQ ID NO: 11 | TCTCCCAACCCTTGTACCAGTG |
| hsa-miR-199a-1 SEQ ID NO: 12 | CCCAGTGTTCAGACTACCTGTTC |
| hsa-miR-203b SEQ ID NO: 13 | UUGAACUGUUAAGAACCACUGGA |
| hsa-miR-221 SEQ ID NO: 14 | AGCTACATTGTCTGCTGGGTTTC |
| hsa-miR-3135b SEQ ID NO: 15 | GGCTGGAGCGAGTGCAGTGGTG |

TABLE 3-continued

Sequences of primers used for qRT-PCR.

| | |
|---|---|
| hsa-miR-3146 SEQ ID NO: 16 | CATGCTAGGATAGAAAGAATGG |
| hsa-miR-3174 SEQ ID NO: 17 | TAGTGAGTTAGAGATGCAGAGCC |
| hsa-miR-3662 SEQ ID NO: 18 | GAAAATGATGAGTAGTGACTGATG |
| hsa-miR-379 SEQ ID NO: 19 | TGGTAGACTATGGAACGTAGG |
| hsa-miR-4419 SEQ ID NO: 20 | TGAGGGAGGAGACTGCA |
| hsa-miR-4513 SEQ ID NO: 21 | AGACTGACGGCTGGAGGCCCAT |
| hsa-miR-4523 SEQ ID NO: 22 | GACCGAGAGGGCCTCGGCTGT |
| hsa-miR-4531 SEQ ID NO: 23 | ATGGAGAAGGCTTCTGA |
| hsa-miR-4718 SEQ ID NO: 24 | AGCTGTACCTGAAACCAAGCA |
| hsa-miR-4743 SEQ ID NO: 25 | TGGCCGGATGGGACAGGAGGCAT |
| hsa-miR-4798 SEQ ID NO: 26 | TTCGGTATACTTTGTGAATTGG |
| hsa-miR-494 SEQ ID NO: 27 | TGAAACATACACGGGAAACCTC |
| hsa-miR-518a-1 SEQ ID NO: 28 | CTGCAAAGGGAAGCCCTTTC |
| hsa-miR-551a SEQ ID NO: 29 | GCGACCCACTCTTGGTTTCCA |
| hsa-miR-562 SEQ ID NO: 30 | AAAGTAGCTGTACCATTTGC |
| hsa-miR-661 SEQ ID NO: 31 | TGCCTGGGTCTCTGGCCTGCGCGT |
| hsa-miR-889 SEQ ID NO: 32 | TTAATATCGGACAACCATTGT |
| hsa-miR-9-3 SEQ ID NO: 33 | TCTTTGGTTATCTAGCTGTATGA |
| RNU6 SEQ ID NO: 34 | ACACGCAAATTCGTGAAGCGTTC |

TABLE 3-continued

| Sequences of primers used for qRT-PCR. | |
|---|---|
| Universal Reverse | Qiagen universal reverse |
| 18S-F SEQ ID NO: 35 | GTAACCCGTTGAACCCCATT |
| 18S-R SEQ ID NO: 36 | CCATCCAATCGGTAGTAGCG |

TABLE 4

Comparison of binding affinities of 4 and 4-Fl towards selected RNAs

| RNA | 4-FL (μM) | 4 (μM) |
|---|---|---|
| 4IL1 | 5.2 ± 0.7 | 5.5 ± 1.3 |
| 4IL8 | 7.0 ± 1.1 | 7.5 ± 0.6 |

DOCUMENTS CITED (1) Thomas, J. R.; Hergenrother, P. J. Targeting RNA with small molecules. *Chem. Rev.* 2008, 108 (4), 1171.

(2) Guan, L.; Disney, M. D. Recent advances in developing small molecules targeting RNA. *ACS Chem. Biol.* 2012, 7 (1), 73.

(3) Gallego, J.; Varani, G. Targeting RNA with small-molecule drugs: therapeutic promise and chemical challenges. *Acc. Chem. Res.* 2001, 34 (10), 836.

(4) Moehle, K.; Athanassiou, Z.; Patora, K.; Davidson, A.; Varani, G.; Robinson, J. A. Design of beta-Hairpin Peptidomimetics That Inhibit Binding of alpha-Helical HIV-1 Rev Protein to the Rev Response Element RNA. *Angew. Chem. Int. Ed. Engl.* 2007, 24, 24.

(5) Athanassiou, Z.; Patora, K.; Dias, R. L.; Moehle, K.; Robinson, J. A.; Varani, G. Structure-guided peptidomimetic design leads to nanomolar beta-hairpin inhibitors of the Tat-TAR interaction of bovine immunodeficiency virus. *Biochemistry* 2007, 46 (3), 741.

(6) Davidson, A.; Leeper, T. C.; Athanassiou, Z.; Patora-Komisarska, K.; Karn, J.; Robinson, J. A.; Varani, G. Simultaneous recognition of HIV-1 TAR RNA bulge and loop sequences by cyclic peptide mimics of Tat protein. *Proc. Natl. Acad. Sci. USA* 2009, 106 (29), 11931.

(7) Werstuck, G.; Green, M. R. Controlling gene expression in living cells through small molecule-RNA interactions. *Science* 1998, 282 (5387), 296.

(8) Pushechnikov, A.; Lee, M. M.; Childs-Disney, J. L.; Sobczak, K.; French, J. M.; Thornton, C. A.; Disney, M. D. Rational design of ligands targeting triplet repeating transcripts that cause RNA dominant disease: application to myotonic muscular dystrophy type 1 and spinocerebellar ataxia type 3. *J. Am. Chem. Soc.* 2009, 131 (28), 9767.

(9) Velagapudi, S. P.; Gallo, S. M.; Disney, M. D. Sequence-based design of bioactive small molecules that target precursor microRNAs. *Nat. Chem. Biol.* 2014, 10 (4), 291.

(10) Velagapudi, S. P.; Disney, M. D. Two-dimensional combinatorial screening enables the bottom-up design of a microRNA-10b inhibitor. *Chem. Commun.* (*Camb.*) 2014, 50 (23), 3027.

(11) Lee, M. M.; Pushechnikov, A.; Disney, M. D. Rational and modular design of potent ligands targeting the RNA that causes myotonic dystrophy 2. *ACS Chem. Biol.* 2009, 4, 345.

(12) Arambula, J. F.; Ramisetty, S. R.; Baranger, A. M.; Zimmerman, S. C. A simple ligand that selectively targets CUG trinucleotide repeats and inhibits MBNL protein binding. *Proc. Natl. Acad. Sci. USA* 2009, 106 (38), 16068.

(13) Jahromi, A. H.; Nguyen, L.; Fu, Y.; Miller, K. A.; Baranger, A. M.; Zimmerman, S. C. A novel CUG(exp). MBNL1 inhibitor with therapeutic potential for myotonic dystrophy type 1. *ACS Chem. Biol.* 2013, 8 (5), 1037.

(14) Childs-Disney, J. L.; Wu, M.; Pushechnikov, A.; Aminova, O.; Disney, M. D. A small molecule microarray platform to select RNA internal loop-ligand interactions. *ACS Chem. Biol.* 2007, 2 (11), 745.

(15) Velagapudi, S. P.; Seedhouse, S. J.; Disney, M. D. Structure-activity relationships through sequencing (StARTS) defines optimal and suboptimal RNA motif targets for small molecules. *Angew. Chem. Int. Ed. Engl.* 2010, 49 (22), 3816.

(16) Tuerk, C.; Gold, L. Systematic evolution of ligands by exponential enrichment: RNA ligands to bacteriophage T4 DNA polymerase. *Science* 1990, 249 (4968), 505.

(17) Robertson, D. L.; Joyce, G. F. Selection in vitro of an RNA enzyme that specifically cleaves single-stranded DNA. *Nature* 1990, 344 (6265), 467.

(18) Disney, M. D.; Labuda, L. P.; Paul, D. J.; Poplawski, S. G.; Pushechnikov, A.; Tran, T.; Velagapudi, S. P.; Wu, M.; Childs-Disney, J. L. Two-dimensional combinatorial screening identifies specific aminoglycoside-RNA internal loop partners. *J. Am. Chem. Soc.* 2008, 130 (33), 11185.

(19) Siegel, S. R.; Mackenzie, J.; Chaplin, G.; Jablonski, N. G.; Griffiths, L. Circulating microRNAs involved in multiple sclerosis. *Mol. Biol. Rep.* 2012, 39 (5), 6219.

(20) Pan, W.; Zhu, S.; Dai, D.; Liu, Z.; Li, D.; Li, B.; Gagliani, N.; Zheng, Y.; Tang, Y.; Weirauch, M. T. et al. MiR-125a targets effector programs to stabilize Treg-mediated immune homeostasis. *Nat. Commun.* 2015, 6, 7096.

(21) Li, S. P.; Liu, B.; Song, B.; Wang, C. X.; Zhou, Y. C. miR-28 promotes cardiac ischemia by targeting mitochondrial aldehyde dehydrogenase 2 (ALDH2) in *Mus musculus* cardiac myocytes. *Eur. Rev. Med. Pharmacol. Sci.* 2015, 19 (5), 752.

(22) Disney, M. D.; Winkelsas, A. M.; Velagapudi, S. P.; Southern, M.; Fallahi, M.; Childs-Disney, J. L. Inforna 2.0: a platform for the sequence-based design of small molecules targeting structured RNAs. *ACS Chem. Biol.* 2016, 11 (6), 1720.

(23) Chan, T. R.; Hilgraf, R.; Sharpless, K. B.; Fokin, V. V. Polytriazoles as copper(I)-stabilizing ligands in catalysis. *Org. Lett.* 2004, 6 (17), 2853.

(24) Kolb, H. C.; Finn, M. G.; Sharpless, K. B. Click chemistry: diverse chemical function from a few good reactions. *Angew. Chem. Int. Ed. Engl.* 2001, 40 (11), 2004.

(25) Seth, P. P.; Miyaji, A.; Jefferson, E. A.; Sannes-Lowery, K. A.; Osgood, S. A.; Propp, S. S.; Ranken, R.; Massire, C.; Sampath, R.; Ecker, D. J. et al. SAR by MS: discovery of a new class of RNA-binding small molecules for the hepatitis C virus: internal ribosome entry site IIA subdomain. *J. Med. Chem.* 2005, 48 (23), 7099.

(26) Zhou, S.; Rynearson, K. D.; Ding, K.; Brunn, N. D.; Hermann, T. Screening for inhibitors of the hepatitis C virus internal ribosome entry site RNA. *Bioorg. Med. Chem.* 2013, 21, 6139.

(27) Parsons, J.; Castaldi, M. P.; Dutta, S.; Dibrov, S. M.; Wyles, D. L.; Hermann, T. Conformational inhibition of the hepatitis C virus internal ribosome entry site RNA. *Nat. Chem. Biol.* 2009, 5 (11), 823.
(28) Sando, S.; Narita, A.; Aoyama, Y. Light-up Hoechst-DNA aptamer pair: generation of an aptamer-selective fluorophore from a conventional DNA-staining dye. *Chembiochem* 2007, 8 (15), 1795.
(29) Velagapudi, S. P.; Seedhouse, S. J.; French, J.; Disney, M. D. Defining the RNA internal loops preferred by benzimidazole derivatives via 2D combinatorial screening and computational analysis. *J. Am. Chem. Soc.* 2011, 133 (26), 10111.
(30) Blount, K. F.; Wang, J. X.; Lim, J.; Sudarsan, N.; Breaker, R. R. Antibacterial lysine analogs that target lysine riboswitches. *Nat. Chem. Biol.* 2007, 3(1), 44.
(31) Winkler, W. C.; Cohen-Chalamish, S.; Breaker, R. R. An mRNA structure that controls gene expression by binding FMN. *Proc. Natl. Acad. Sci. USA* 2002, 99 (25), 15908.
(32) Winkler, W. C.; Breaker, R. R. Genetic control by metabolite-binding riboswitches. *Chembiochem* 2003, 4 (10), 1024.
(33) Nahvi, A.; Sudarsan, N.; Ebert, M. S.; Zou, X.; Brown, K. L.; Breaker, R. R. Genetic control by a metabolite binding mRNA. *Chem. Biol.* 2002, 9 (9), 1043.
(34) Daldrop, P.; Reyes, F. E.; Robinson, D. A.; Hammond, C. M.; Lilley, D. M.; Batey, R. T.; Brenk, R. Novel ligands for a purine riboswitch discovered by RNA-ligand docking. *Chem. Biol.* 2011, 18 (3), 324.
(35) Gao, W.; He, H. W.; Wang, Z. M.; Zhao, H.; Lian, X. Q.; Wang, Y. S.; Zhu, J.; Yan, J. J.; Zhang, D. G.; Yang, Z. J. et al. Plasma levels of lipometabolism-related miR-122 and miR-370 are increased in patients with hyperlipidemia and associated with coronary artery disease. *Lipids Health Dis.* 2012, 11, 55.
(36) Fede, A.; Billeter, M.; Leupin, W.; Wuthrich, K.; Spink, N.; Brown, D. G.; Skelly, J. V.; Neidle, S. Determination of the NMR solution structure of the Hoechst 33258-d (GTGGAATTCCAC)2 complex and comparison with the X-ray crystal structure Sequence-dependent effects in drug-DNA interaction: the crystal structure of Hoechst 33258 bound to the d(CGCAAATTTGCG)2 duplex. *Structure* 1993, 1 (3), 177.
(37) Lambert, N.; Robertson, A.; Jangi, M.; McGeary, S.; Sharp, P. A.; Burge, C. B. RNA Bind-n-Seq: quantitative assessment of the sequence and structural binding specificity of RNA binding proteins. *Mol. Cell.* 2014, 54 (5), 887.
(38) Liu, B.; Childs-Disney, J. L.; Znosko, B. M.; Wang, D.; Fallahi, M.; Gallo, S. M.; Disney, M. D. Analysis of secondary structural elements in human microRNA hairpin precursors. *BMC bioinformatics* 2016, 17, 112.
(39) Haga, C. L.; Velagapudi, S. P.; Strivelli, J. R.; Yang, W. Y.; Disney, M. D.; Phinney, D. G. Small Molecule Inhibition of miR-544 Biogenesis Disrupts Adaptive Responses to Hypoxia by Modulating ATM-mTOR Signaling. *ACS Chem. Biol.* 2015, 10 (10), 2267.
(40) Tran, T. P.; Vo, D. D.; Di Giorgio, A.; Duca, M. Ribosome-targeting antibiotics as inhibitors of oncogenic microRNAs biogenesis: Old scaffolds for new perspectives in RNA targeting. *Bioorg. Med. Chem.* 2015, 23 (17), 5334.
(41) Vo, D. D.; Staedel, C.; Zehnacker, L.; Benhida, R.; Darfeuille, F.; Duca, M. Targeting the production of oncogenic microRNAs with multimodal synthetic small molecules. *ACS Chem. Biol.* 2014, 9 (3), 711.
(42) Bose, D.; Jayaraj, G.; Suryawanshi, H.; Agarwala, P.; Pore, S. K.; Banerjee, R.; Maiti, S. The tuberculosis drug streptomycin as a potential cancer therapeutic: inhibition of miR-21 function by directly targeting its precursor. *Angew. Chem. Int. Ed. Engl.* 2012, 51 (4), 1019.
(43) He, L.; Thomson, J. M.; Hemann, M. T.; Hernando-Monge, E.; Mu, D.; Goodson, S.; Powers, S.; Cordon-Cardo, C.; Lowe, S. W.; Hannon, G. J. et al. A microRNA polycistron as a potential human oncogene. *Nature* 2005, 435 (7043), 828.
(44) Qiang, X. F.; Zhang, Z. W.; Liu, Q.; Sun, N.; Pan, L. L.; Shen, J.; Li, T.; Yun, C.; Li, H.; Shi, L. H. miR-20a promotes prostate cancer invasion and migration through targeting ABL2. *J. Cell. Biochem.* 2014, 115 (7), 1269.
(45) Hsu, T. I.; Hsu, C. H.; Lee, K. H.; Lin, J. T.; Chen, C. S.; Chang, K. C.; Su, C. Y.; Hsiao, M.; Lu, P. J. MicroRNA-18a is elevated in prostate cancer and promotes tumorigenesis through suppressing STK4 in vitro and in vivo. *Oncogenesis* 2014, 3, e99.
(46) Guan, L.; Disney, M. D. Covalent small molecule-RNA complex formation enables cellular profiling of small molecule-RNA interactions. *Angew. Chem. Int. Ed. Engl.* 2013, 52 (38), 10010.
(47) Su, Z.; Zhang, Y.; Gendron, T. F.; Bauer, P. O.; Chew, J.; Yang, W. Y.; Fostvedt, E.; Jansen-West, K.; Belzil, V. V.; Desaro, P. et al. Discovery of a biomarker and lead small molecules to target r(GGGGCC)-associated defects in c9FTD/ALS. *Neuron* 2014, 83 (5), 1043.
(48) Velagapudi, S. P.; Pushechnikov, A.; Labuda, L. P.; French, J. M.; Disney, M. D. Probing a 2-aminobenzimidazole library for binding to RNA internal loops via two-dimensional combinatorial screening. *ACS Chem. Biol.* 2012, 7(11), 1902.
(49) Peyret, N.; Seneviratne, P. A.; Allawi, H. T.; SantaLucia, J., Jr. Nearest-neighbor thermodynamics and NMR of DNA sequences with internal A.A, C.C, G.G, and T.T mismatches. *Biochemistry* 1999, 38 (12), 3468.
(50) Puglisi, J. D.; Tinoco, I., Jr. Absorbance melting curves of RNA. *Methods Enzymol.* 1989, 180, 304.
(51) O'Donnell, K. A.; Wentzel, E. A.; Zeller, K. I.; Dang, C. V.; Mendell, J. T. c-Myc-regulated microRNAs modulate E2F1 expression. *Nature* 2005, 435 (7043), 839.

Examples

Section 1: Synthesis and Characterization of Ligands (1-8) Used in 2DCS Screening Abbreviations: DCM, dichloromethane; DMF, dimethylformamide; EDC, 1-ethyl-3-(3-dimethylaminopropyl)carbodiimide; HCl, hydrochloric acid; HOBT, hydroxybenzotriazole; HPLC, high performance liquid chromatography; HRMS, high resolution mass spectrometry; KOH, potassium hydroxide; MeOH, methanol; MS-ESI; mass spectrometry-electrospray ionization; NMR; nuclear magnetic resonance; $Pd(PPh_3)_4$ (tetrakis(triphenylphosphine)palladium(0); Pd/C, palladium on activated carbon; THF, tetrahydrofuran; TLC, thin layer chromatography Scheme 1
Synthesis of 4′-(4-methylpiperazin-1-yl)-4-nitro-[1,1′-biphenyl]-3-amine (9)

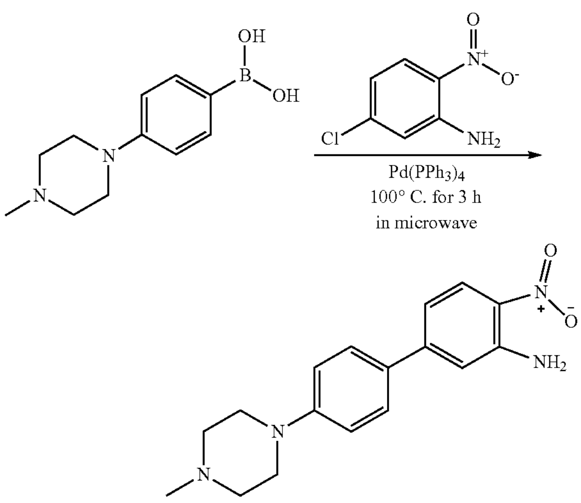

9

A solution of 5-chloro-2-nitroaniline (580 μmoles), (4-(4-methylpiperazin-1-yl)phenyl)boronic acid (696 μmoles), and potassium carbonate (2 mmoles) was mixed by stirring in dimethylformamide (DMF, 2 mL) under an Argon atmosphere in a 5 mL Biotage microwave vial. After 5 min of mixing, $Pd(PPh_3)_4$ (tetrakis(triphenylphosphine)palladium (0), 29 μmoles) was added to the reaction mixture. The vial was capped, placed in the Biotage Initiator+SP wave microwave-reactor, and was heated at 100° C. for 3 h. The solvent was then removed by rotatory evaporation under reduced pressure. The desired product was purified by column chromatography using a gradient of 0-10% methanol in dichloromethane (DCM) (Yield: 145 mg, 80%). MS-ESI (+) HRMS: Calculated: ($C_{17}H_{20}N_4O_2$) 313.1665 ($M+H^+$); observed: 313.1658 ($M+H^+$). $^1H$ NMR: ($CDCl_3$, 400 MHz) δ 2.30 (3H, s), 2.52 (4H, t, J=5 Hz), 3.23 (4H, t, J=5), 6.85 (1H, d, J=8 Hz), 6.86 (1H, s), 6.91 (2H, d, J=8 Hz), 7.44 (2H, d, J=8 Hz), 8.07 (1H, d, J=9 Hz). $^{13}C$ NMR: ($CDCl_3$, 100 MHz) δ 46.17, 48.29, 54.93, 114.99, 115.56, 115.80, 126.82, 127.99, 128.98, 130.81, 145.04, 148.17, 151.66.

Scheme 2 Synthesis of 5-(1H-indol-5-yl)-2-nitroaniline (10)

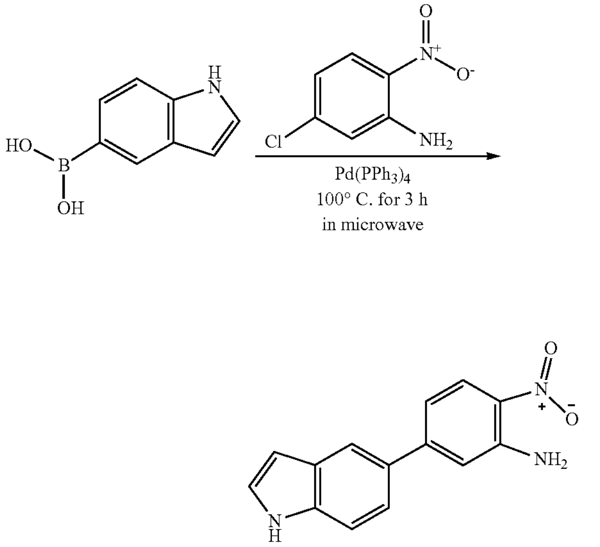

10

A solution of 5-chloro-2-nitroaniline (580 μmoles), (1H-indol-5-yl)boronic acid (696 μmoles), and potassium carbonate (2 mmoles) was mixed by stirring in DMF (2 mL) under an Argon atmosphere using a 5 mL Biotage microwave vial. After 5 min of mixing, $Pd(PPh_3)_4$ (29 μmoles) was added to the reaction mixture. The vial was capped, placed in the Biotage Initiator+SP wave microwave-reactor, and was heated at 100° C. for 3 h. The solvent was then removed by rotatory evaporation under reduced pressure. The desired product was purified by column chromatography using a gradient of 0-100% ethyl acetate in n-hexane (Yield: 70 mg, 50%).

MS-ESI (+) HRMS: ($C_{14}H_{11}N_3O_2$) Calculated: 254.0930 ($M+H^+$); observed: 254.0928 ($M+H^+$). $^1H$ NMR: ($CD_3OD$, 400 MHz) δ 6.54 (1H, d, J=3 Hz), 7.00 (1H, d, J=9 Hz), 7.24 (1H, d, J=4 Hz), 7.30 (1H, d, J=4 Hz), 7.45 (2H, m), 7.89 (1H, s), 8.11 (1H, d, J=9 Hz). $^{13}C$ NMR: ($CDCl_3$, 100 MHz) δ 103.09, 112.63, 116.57, 116.92, 120.18, 121.67, 126.80, 127.17, 129.98, 130.99, 131.34, 138.07, 147.87, 151.48.

Synthesis of 1

1

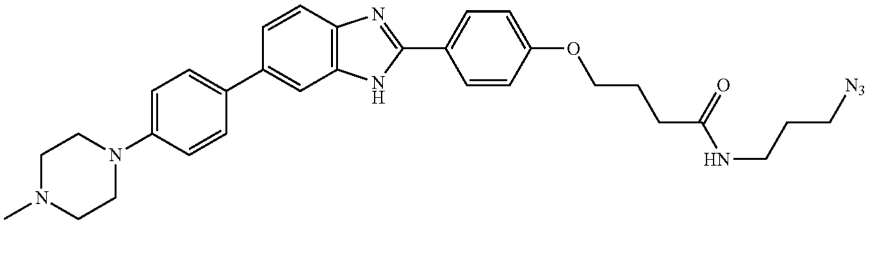 [SMILES: CN1CCN(c2ccc(-c3ccc4nc(-c5ccc(OCCCC(=O)NCCCN=[N+]=[N-])cc5)[nH]c4c3)cc2)CC1]

Approximately 40 μmoles of 9 was dissolved in 3 mL of ethanol and was supplemented with 10% (w/w) Pd/C (palladium on activated carbon). Hydrogenation was performed using a shaker hydrogenation apparatus (Parr Instrument Company, IL) with constant supply of hydrogen gas at 20 psi. The reaction was shaken at room temperature overnight to afford the diamine compound (4'-(4-methylpiperazin-1-yl)-[1,1'-biphenyl]-3,4-diamine (11). The reaction was then immediately supplemented with a solution of 50% ethanol in water containing 1.2 equivalents of sodium metabisulfite and 1.2 equivalents of ethyl 4-(4-formylphenoxy)butanoate (12). The reaction was heated to reflux overnight to afford the benzimidazole ester derivative (13). Solvent was then removed by rotatory evaporation at reduced pressure, and the product was isolated by column chromatography using a gradient of 0-10% MeOH in DCM.

Approximately 20 μmoles of 13 was dissolved in 2.4 mL solution of 3:1 THF:water. The solution was then supplemented with 1.2 equivalents of KOH. The reaction mixture was refluxed overnight to afford carboxylic acid. After complete conversion to the carboxylic acid product as confirmed by TLC and mass spectrometry, the reaction mixture was quenched by adding an aliquot of 5% HCl solution until the pH was between 5 and 6. Aqueous and organic solvent was removed by rotary evaporation at reduced pressure. To the dried carboxylic acid product, 3 mL solution of 2 equivalents of 3-azido-propylamine, 2 equivalents of EDC, and 2 equivalents of HOBT in anhydrous DMF was added. The reaction mixture was stirred overnight at room temperature to afford the final product of benzimidazole derivative, 1, containing an azido group. Solvent was then removed by rotatory evaporation at reduced pressure and the product was isolated by column chromatography using a gradient of 0-10% MeOH in DCM (Yield: approx. 5 mg; ~20% overall). (see Scheme 3 below)

Characterization of 13: MS-ESI (+) HRMS: ($C_{30}H_{34}N_4O_3$) Calculated: 499.2704 ($M+H^+$); observed: 499.2709 ($M+H^+$). $^1H$ NMR ($CD_3$-OD, 400 MHz) δ 1.27 (3H, t, J=7 Hz), 2.18 (2H, m), 2.59 (2H, t, J=7 Hz), 3.01 (3H, s), 3.15 (2H, t, J=13 Hz), 3.67 (2H, d, J=12 Hz), 3.98 (2H, d, J=11 Hz), 4.19 (4H, m), 7.19 (2H, d, J=9 Hz), 7.36 (2H, d, J=9 Hz), 7.67 (5H, m), 7.88 (2H, m), 7.96 (1H, t, J=1 Hz). $^{13}C$ NMR ($CD_3$-OD, 400 MHz) δ 14.53, 25.66, 31.54, 43.59, 47.69, 54.63, 61.65, 68.64, 111.89, 114.50, 115.18, 121.08, 121.33, 125.21, 127.06, 129.33, 132.06, 132.50, 133.54, 133.88, 141.38, 150.99, 161.40, 174.90.

Characterization of 1: MS-ESI (+) HRMS: ($C_{31}H_{36}N_8O_2$) Calculated: 553.3039 ($M+H^+$); observed: 553.3036 ($M+H^+$). $^1H$ NMR: ($CD_3$-OD, 400 MHz) δ 1.77 (2H, m), 2.17 (2H, m), 2.46 (2H, t, J=8 Hz), 3.01 (3H, s), 3.15 (2H, t, J=12 Hz), 3.29 (2H, m), 3.34 (2H, m), 3.67 (2H, d, J=12 Hz), 3.97 (2H, d, J=13 Hz), 4.20 (2H, t, J=6 Hz), 7.18 (2H, d, J=7 Hz), 7.37 (1H, d, J=10 Hz), 7.60-7.76 (5H, m), 7.88 (2H, m), 7.95 (1H, s). $^{13}C$ NMR: ($CD_3$-OD, 100 MHz) δ 26.36, 29.70, 33.33, 37.79, 43.60, 47.68, 50.08, 54.62, 68.85, 111.87, 114.29, 115.17, 118.18, 121.09, 121.62, 125.14, 127.07, 129.32, 131.99, 132.48, 133.49, 133.49, 141.38, 150.94, 150.99, 161.42, 175.46.

Synthesis of 2

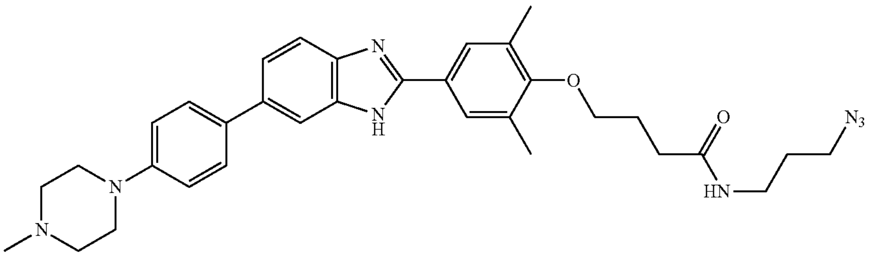 [SMILES: Cc1cc(-c2nc3ccc(-c4ccc(N5CCN(C)CC5)cc4)cc3[nH]2)cc(C)c1OCCCC(=O)NCCCN=[N+]=[N-]]

2

Approximately 40 μmole of 9 was dissolved in 3 mL of ethanol and was supplemented with 10% (w/w) Pd/C. Hydrogenation was performed using a shaker hydrogenation apparatus (Parr Instrument Company, IL) with constant supply of hydrogen gas at 20 psi. The reaction was shaken at room temperature overnight to afford the diamine compound (4'-(4-methylpiperazin-1-yl)-[1,1'-biphenyl]-3,4-diamine (11). The reaction was then immediately supplemented with a solution of 50% ethanol in water containing 1.2 equivalents of sodium metabisulfite and 1.2 equivalents of ethyl 4-(4-formyl-2,6-dimethylphenoxy)butanoate (14). The reaction was heated to reflux overnight to afford the benzimidazole ester derivative (15). Solvent was then removed by rotatory evaporation at reduced pressure and the product was isolated by column chromatography using a gradient of 0-10% MeOH in DCM. Approximately 20 μmoles of 15 was dissolved in 2.4 mL solution of 3:1 THF:water. The solution was then supplemented with 1.2 equivalents of KOH. The reaction mixture was refluxed overnight to afford carboxylic acid. After complete conversion to carboxylic acid product as confirmed by TLC and mass spectrometry, the reaction mixture was quenched by adding an aliquot of 5% HCl solution until the pH was between 5 and 6. Aqueous and organic solvent was removed by rotary evaporation at reduced pressure. To the dried carboxylic acid product, a 3 mL solution of 2 equivalents of 3-azido-propylamine, 2 equivalents of EDC, and 2 equivalents of HOBT in anhydrous DMF was added. The reaction mixture was stirred overnight at room temperature to afford the final product of benzimidazole derivative, 2, containing an azido group. Solvent was then removed by rotatory evaporation at reduced pressure, and the product was isolated by column chromatography using a gradient of 0-10% MeOH in DCM (Yield: approx. 5 mg, ~20% overall). (see Scheme 4 below)

Characterization of 15: MS-ESI (+) HRMS: ($C_{32}H_{38}N_4O_3$) Calculated: 527.3016 ($M+H^+$); observed: 527.3022 ($M+H^+$). $^1H$ NMR ($CD_3OD$, 400 MHz) δ 1.29 (3H, t, J=7 Hz), 2.18 (2H, m), 2.45 (6H, s), 2.65 (2H, t, J=7 Hz), 3.02 (3H, s), 3.14 (3H, t, J=11 Hz), 3.67 (2H, d, J=11 Hz), 3.98 (4H, t, J=6 Hz), 4.18 (2H, q, J=7 Hz), 7.19 (2H, d, J=9 Hz), 7.69 (2H, d, J=9 Hz), 7.88 (5, m). $^{13}C$ NMR ($CD_3OD$, 100 MHz) δ 14.55, 16.67, 26.73, 31.51, 43.59, 47.72, 54.65, 61.63, 72.47, 111.76, 114.99, 118.20, 119.30, 126.76, 129.32, 129.65, 132.06, 133.65, 133.87, 134.78, 141.14, 150.95, 151.12, 162.10, 174.69.

Characterization of 2: MS-ESI (+) HRMS: Calculated: ($C_{33}H_{40}N_8O_2$) 581.3352 (M+H$^+$); observed: 581.335 (M+H$^+$). $^1$H NMR: ($CD_3OD$, 400 MHz) δ 1.79 (2H, m), 2.17 (2H, m), 2.44 (6H, s), 2.51 (2H, t, J=7 Hz), 3.01 (3H, s), 3.15 (2H, t, J=13 Hz), 3.31 (2H, m), 3.38 (2H, m), 3.67 (2H, d, J=12 Hz), 3.95 (3H, t, J=6 Hz), 4.00 (2H, s), 7.17 (2H, d, J=9 Hz), 7.68 (2H, d, J=9 Hz), 7.79-7.95 (5H, m). $^{13}$C NMR: ($CD_3OD$, 100 MHz) δ 16.74, 27.50, 29.77, 33.29, 37.78, 43.59, 47.69, 50.11, 54.63, 55.15, 72.83, 111.70, 114.96, 118.17, 119.12, 126.78, 129.28, 129.65, 131.91, 133.52, 133.75, 134.85, 141.12, 150.95, 150.99, 162.19, 175.48.

Synthesis of 3

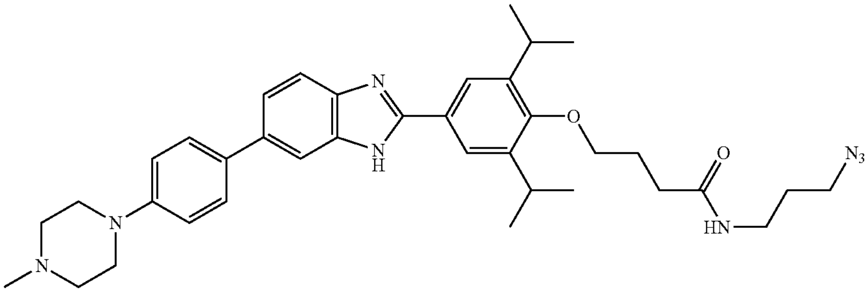 [SMILES: CC(C)c1cc(-c2nc3ccc(-c4ccc(N5CCN(C)CC5)cc4)cc3[nH]2)cc(C(C)C)c1OCCCC(=O)NCCCN=[N+]=[N-]]

3

Approximately 40 μmole of 9 was dissolved in 3 mL of ethanol and was supplemented with 10% (w/w) Pd/C. Hydrogenation was performed using a shaker hydrogenation apparatus (Parr Instrument Company, IL) with constant supply of hydrogen gas at 20 psi. The reaction was shaken at room temperature overnight to afford the diamine compound (4'-(4-methylpiperazin-1-yl)-[1,1'-biphenyl]-3,4-diamine (11). The reaction was then immediately supplemented with a solution of 50% ethanol in water containing 1.2 equivalents of sodium metabisulfite and 1.2 equivalents of 4-(4-formyl-2,6-diisopropylphenoxy)butanoate (16). The reaction was heated to reflux overnight to afford the benzimidazole ester derivative (17). Solvent was then removed by rotatory evaporation at reduced pressure and the product was isolated by column chromatography using a gradient of 0-10% MeOH in DCM. Approximately 20 μmoles of 17 was dissolved in 2.4 mL solution of 3:1 THF:water. The solution was then supplemented with 1.2 equivalents of KOH. The reaction mixture was refluxed overnight to afford carboxylic acid. After complete conversion to carboxylic acid product as confirmed by TLC and mass spectrometry, the reaction mixture was quenched by adding an aliquot of 5% HCl solution until the pH was between 5 and 6. Aqueous and organic solvent was removed by rotary evaporation at reduced pressure. To the dried carboxylic acid product, a 3 mL solution of 2 equivalents of 3-azido-propylamine, 2 equivalents of EDC, and 2 equivalents of HOBT in anhydrous DMF was added. The reaction mixture was stirred overnight at room temperature to afford the final product of benzimidazole derivative, 3, containing an azido group. Solvent was then removed by rotatory evaporation at reduced pressure and the product was isolated by column chromatography using a gradient of 0-10% MeOH in DCM (Yield: approx. 5 mg, ~20% overall). (see Scheme 5 below)

Characterization of 17: MS-ESI (+) HRMS: Calculated: ($C_{36}H_{46}N_4O_3$) 583.3642 (M+H$^+$); observed: 583.3648 (M+H$^+$). $^1$H NMR: ($CD_3OD$, 400 MHz) δ 1.23 (16H, m), 2.17 (2H, m), 2.41 (3H, s), 2.68 (6H, m), 3.28 (3H, t, J=5 Hz), 3.38 (2H, m), 3.87 (2H, t, J=6 Hz), 4.19 (2H, q, J=7 Hz), 7.07 (2H, d, J=9 Hz), 7.50 (1H, d, J=5 Hz), 7.58 (2H, d, J=9 Hz), 7.63 (1H, d, J=8 Hz), 7.77 (1H, s), 7.95 (2H, s). $^{13}$C NMR: ($CD_3OD$, 100 MHz) δ 14.6, 24.34, 26.72, 28.00, 31.52, 45.98, 49.86, 55.91, 61.65, 74.70, 117.71, 124.04, 127.19, 128.80, 134.76, 137.54, 144.14, 151.48, 154.16, 156.48, 175.00.

Characterization of 3: MS-ESI (+) HRMS: Calculated: ($C_{37}H_{47}N_8O_2$) 637.3978 (M+H$^+$); observed: 637.3978 (M+H$^+$). $^1$H NMR (MeOH-$D_4$, 400 MHz) δ 1.37 (12H, d, J=7 Hz), 1.80 (2H, m), 2.20 (2H, m), 2.53 (2H, t, J=7 Hz), 3.01 (3H, s), 3.16 (2H, t, J=12 Hz), 3.30 (2H, m), 3.39 (2H, m), 3.45 (2H, m), 3.67 (2H, d, J=12 Hz), 3.88-4.05 (5H, m), 7.18 (2H, d, J=9 Hz), 7.69 (2H, d, J=7 Hz), 7.85 (2H, d, J=1 Hz), 7.94 (1H, t, J=1 Hz), 8.03 (2H, s). $^{13}$C NMR (MeOH-$D_4$, 100 MHz) δ 24.13, 27.44, 28.19, 29.80, 33.19, 37.83, 43.60, 47.70, 50.13, 54.62, 55.15, 75.51, 111.77, 114.98, 118.20, 120.09, 125.54, 126.79, 129.31, 132.01, 133.63, 133.85, 141.15, 145.88, 150.95, 151.28, 159.70, 175.40.

Synthesis of 4

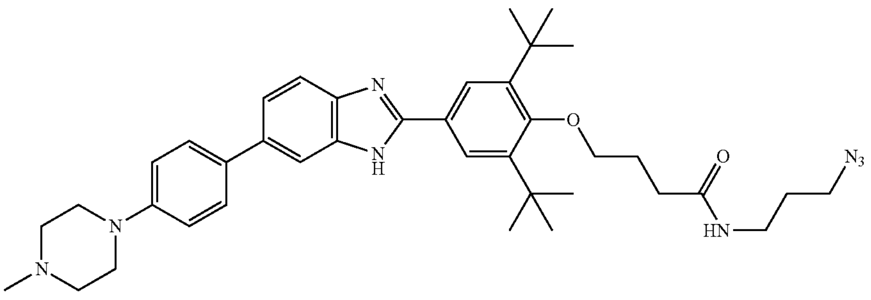

4

Targapromir-18a

Approximately 40 μmole of 9 was dissolved in 3 mL of ethanol and was supplemented with 10% (w/w) Pd/C. Hydrogenation was performed using a shaker hydrogenation apparatus (Parr Instrument Company, IL) with constant supply of hydrogen gas at 20 psi. The reaction was shaken at room temperature overnight to afford the diamine compound (4'-(4-methylpiperazin-1-yl)-[1,1'-biphenyl]-3,4-diamine (11). The reaction was then immediately supplemented with a solution of 50% ethanol in water containing 1.2 equivalents of sodium metabisulfite and 1.2 equivalents of 4-(4-formyl-2,6-di-tert-butylphenoxy)butanoate (18). The reaction was heated to reflux overnight to afford the benzimidazole ester derivative (19). Solvent was then removed by rotatory evaporation at reduced pressure and the product was isolated by column chromatography using a gradient of 0-10% MeOH in DCM.

Approximately 20 μmoles of 19 was dissolved in 2.4 mL solution of 3:1 THF:water. The solution was then supplemented with 1.2 equivalents of KOH. The reaction mixture was refluxed overnight to afford the carboxylic acid. After complete conversion to the carboxylic acid product as confirmed by TLC and mass spectrometry, the reaction mixture was quenched by adding aliquot of 5% HCl solution until the pH was between 5 and 6. Aqueous and organic solvent was removed by rotary evaporation at reduced pressure. To the dried carboxylic acid product, a 3 mL solution of 2 equivalents of 3-azido-propylamine, 2 equivalents of EDC, and 2 equivalents of HOBT in anhydrous DMF was added. The reaction mixture was stirred overnight at room temperature to afford the final product of benzimidazole derivative, 4, containing an azido group. Solvent was then removed by rotatory evaporation at reduced pressure and the product was isolated by column chromatography using a gradient of 0-10% MeOH in DCM (Yield: approx. 5 mg, ~20% overall). (see Scheme 6 below)

Characterization of 19: MS-ESI (+) HRMS: Calculated: ($C_{38}H_{50}N_4O_3$) 611.3961 ($M+H^+$); observed: 611.3958 ($M+H^+$). $^1H$ NMR: ($CD_3OD$, 400 MHz) δ 1.26 (4H, t, J=7 Hz), 1.51 (18H, s), 2.19 (2H, m), 2.43 (3H, s), 2.49 (2H, t, J=7 Hz), 2.72 (4H, t, J=4 Hz), 3.27 (4H, t, J=5 Hz), 3.80 (2H, t, J=8 Hz), 4.13 (2H, q, J=7 Hz), 7.04 (2H, d, J=9 Hz), 7.47 (1H, d, J=7 Hz), 7.55 (2H, d, J=8 Hz), 7.61 (1H, d, J=8 Hz), 7.73 (1H, s), 8.06 (1H, s). $^{13}C$ NMR: ($CD_3OD$, 100 MHz) δ 14.57, 25.95, 31.29, 32.59, 37.12, 45.83, 49.74, 49.87, 55.83, 61.70, 76.68, 117.75, 123.00, 125.42, 126.75, 128.81, 134.86, 137.46, 145.89, 151.37, 154.39, 161.18, 174.68.

Characterization of 4: MS-ESI (+) HRMS: ($C_{39}H_{52}N_8O_2$) Calculated: 665.4291 ($M+H^+$); observed: 665.4285 ($M+H^+$). $^1H$ NMR: ($CD_3OD$, 400 MHz) δ 1.55 (18H, s), 1.77 (2H, m), 2.26 (2H, m), 2.38 (2H, t, J=7 Hz), 3.01 (3H, s), 3.16 (2H, t, J=12 Hz), 3.27 (2H, t, J=7 Hz), 3.37 (2H, t, J=4 Hz), 3.67 (2H, d, J=11 Hz), 3.85 (2H, t, J=7 Hz), 3.98 (2H, m), 7.18 (2H, d, J=9 Hz), 7.78 (2H, d, J=5 Hz), 7.85 (2H, d, J=1), 7.94 (1H, t, J=1 Hz), 8.14 (2H, s). $^{13}C$ NMR: ($CD_3OD$, 100 MHz) δ 26.70, 29.75, 32.37, 32.96, 37.40, 37.83, 43.60, 54.61, 77.54, 111.77, 114.97, 118.20. 118.50, 126.70, 128.00, 129.30, 132.09, 133.65. 133.92, 141.06, 147.63, 150.94, 151.44, 164.35, 175.06.

Synthesis of 5

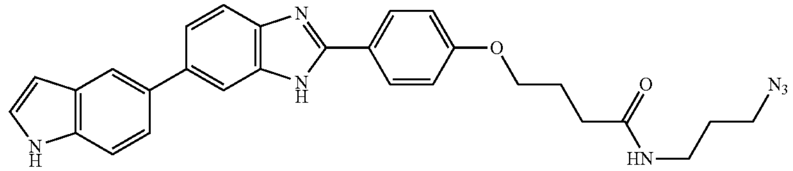

5

Approximately 40 μmole of 10 was dissolved in 3 mL of ethanol and was supplemented with 10% (w/w) Pd/C. Hydrogenation was performed using a shaker hydrogenation apparatus (Parr Instrument Company, IL) with constant supply of hydrogen gas at 20 psi. The reaction was shaken at room temperature overnight to afford the diamine compound (4-(1H-indol-5-yl)benzene-1,2-diamine (20). The reaction was then immediately supplemented with a solution of 50% ethanol in water containing 1.2 equivalents of sodium metabisulfite and 1.2 equivalents of ethyl 4-(4-formylphenoxy)butanoate (12). The reaction was heated to reflux overnight to afford the benzimidazole ester derivative (21). Solvent was then removed by rotatory evaporation at reduced pressure and the product was isolated by column chromatography using a gradient of 0-100% ethyl acetate in n-hexanes.

Approximately 20 μmoles of 21 was dissolved in 2.4 mL solution of 3:1 THF:water. The solution was then supplemented with 1.2 equivalents of KOH. The reaction mixture was refluxed overnight to afford the carboxylic acid. After complete conversion to the carboxylic acid product as confirmed by TLC and mass spectrometry, the reaction mixture was quenched by adding an aliquot of 5% HCl solution until the pH was between 5 and 6. Aqueous and organic solvent was removed by rotary evaporation at reduced pressure. To the dried carboxylic acid product, a 3 mL solution of 2 equivalents of 3-azido-propylamine, 2 equivalents of EDC, and 2 equivalents of HOBT in anhydrous DMF was added. The reaction mixture was stirred overnight at room temperature to afford the final product of benzimidazole derivative, 1, containing an azido group. Solvent was then removed by rotatory evaporation at reduced pressure and the product was isolated by column chromatography using a gradient of 0-100% ethyl acetate in DCM (Yield: approx. 5 mg, ~20% overall). (see Scheme 7 below)

Characterization of 21: MS-ESI (+) HRMS: Calculated: ($C_{27}H_{25}N_3O_3$) 440.1974 ($M+H^+$); observed: 440.1963 ($M+H^+$). $^1H$ NMR: ($CD_3OD$, 400 MHz) δ 1.27 (3H, t, J=7 Hz), 2.14 (2H, m), 2.56 (2H, t, J=7 Hz), 4.16 (4H, m), 6.50 (1H, d, J=4 Hz), 7.25-7.90 (11H, m). $^{13}C$ NMR: ($CD_3OD$, 100 MHz) δ 14.55, 25.65, 31.54, 61.66, 68.55, 112.14, 112.79, 114.16, 114.83, 120.03, 120.85, 121.88, 125.24, 130.02, 131.71, 131.99, 132.30, 133.86, 137.52, 143.41, 150.39, 161.25, 174.89.

Characterization of 5: MS-ESI (+) HRMS: Calculated: ($C_{27}H_{27}N_7O_2$) 494.2304 ($M+H^+$); observed: 494.229 ($M+H^+$). $^1H$ NMR: ($CD_3OD$, 400 MHz) δ 1.77 (2H, m), 2.17 (2H, m), 2.46 (2H, t, J=7 Hz), 3.29 (2H, t, J=7 Hz), 3.36 (2H, m), 4.19 (2H, t, J=6 Hz), 7.32 (2H, m), 7.44-7.54 (2H, m), 7.60-7.74 (3H, m), 7.80-7.98 (4H, m). $^{13}C$ NMR: ($CD_3OD$, 100 MHz) δ 26.38, 29.71, 33.33, 37.79, 50.09, 68.80, 112.36, 112.82, 114.18, 114.95, 120.17, 120.92, 121.19, 122.02, 125.75, 127.63, 130.10, 132.31, 132.38, 134.26, 137.58, 143.60, 150.79, 161.38, 175.44.

Synthesis of 6

6

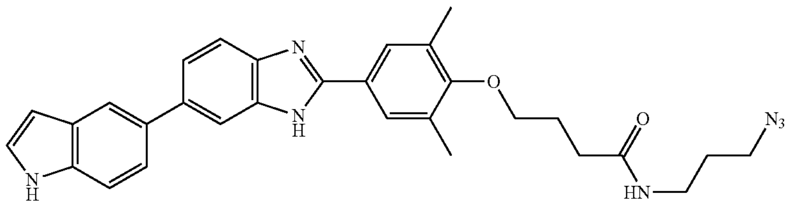

Approximately 40 μmole of 10 was dissolved in 3 mL of ethanol and was supplemented with 10% (w/w) Pd/C. Hydrogenation was performed using a shaker hydrogenation apparatus (Parr Instrument Company, IL) with constant supply of hydrogen gas at 20 psi. The reaction was shaken at room temperature overnight to afford the diamine compound (4'-(4-methylpiperazin-1-yl)-[1,1'-biphenyl]-3,4-diamine (20). The reaction was then immediately supplemented with a solution of 50% ethanol in water containing 1.2 equivalents of sodium metabisulfite and 1.2 equivalents of ethyl 4-(4-formyl-2,6-dimethylphenoxy)butanoate (14). The reaction was heated to reflux overnight to afford the benzimidazole ester derivative (22). Solvent was then removed by rotatory evaporation at reduced pressure and the product was isolated by column chromatography using a gradient of 0-100% ethyl acetate in n-hexane.

Approximately 20 μmoles of 22 was dissolved in 2.4 mL solution of 3:1 THF:water. The solution was then supplemented with 1.2 equivalents of KOH. The reaction mixture was refluxed overnight to afford the carboxylic acid. After complete conversion to the carboxylic acid product as confirmed by TLC and mass spectrometry, the reaction mixture was quenched by adding aliquot of 5% HCl solution until the pH was between 5 and 6. Aqueous and organic solvent was removed by rotary evaporation at reduced pressure. To the dried carboxylic acid product, a 3 mL solution of 2 equivalents of 3-azido-propylamine, 2 equivalents of EDC, and 2 equivalents of HOBT in anhydrous DMF was added. The reaction mixture was stirred overnight at room temperature to afford the final product of benzimidazole derivative, 6, containing an azido group. Solvent was then removed by rotatory evaporation at reduced pressure and the product was isolated by column chromatography using a gradient of 0-100% ethyl acetate in DCM (Yield: approx. 5 mg, ~20% overall). (see Scheme 8 below)

Characterization of 22: MS-ESI (+) HRMS: Calculated: ($C_{29}H_{29}N_3O_3$) 468.2287 ($M+H^+$); observed: 468.2283 ($M+H^+$). $^1H$ NMR: ($CDCl_3$, 400 MHz) δ 1.29 (4H, t, J=7 Hz), 2.13 (2H, m), 2.25 (6H, s), 2.59 (2H, t, J=7 Hz), 3.78 (2H, t, J=6 Hz), 4.18 (2H, q, J=7 Hz), 6.61 (1H, t, J=2 Hz), 7.25 (1H, t, J=3 Hz), 7.28 (1H, s), 7.45 (2H, m), 7.57 (1H, d, J=8 Hz), 7.70 (1H, d, J=8 Hz), 7.77 (2H, s), 7.81 (1H, s), 7.87 (1H, s), 8.37 (1H, s). $^{13}C$ NMR: ($CDCl_3$, 100 MHz) δ 14.25, 116.26, 25.26, 30.85, 60.52, 70.86, 102.93, 111.25, 119.35, 122.20, 123.10, 124.84, 125.00, 127.33, 128.43, 131.81, 133.88, 135.61, 138.01, 152.01, 157.63, 173.36.

Characterization of 6: MS-ESI (+) HRMS: Calculated: ($C_{30}H_{31}N_7O_2$) 522.2618 ($M+H^+$); observed: 522.2618 ($M+H^+$). $^1H$ NMR: ($CD_3OD$, 400 MHz) δ 1.80 (2H, m), 2.18 (2H, m), 2.16 (6H, s), 2.52 (2H, t, J=7 Hz), 3.31 (2H, m), 3.39 (2H, t, J=7 Hz), 3.96 (2H, t, J=6 Hz), 6.56 (1H, dd, J=3, 1 Hz), 7.32 (1H, t, J=2 Hz), 7.45-7.55 (2H, m), 7.80-8.00 (6H, m). $^{13}C$ NMR: ($CD_3OD$, 100 MHz) δ 18.25, 29.08, 31.31, 34.94, 39.32, 41.97, 51.40, 51.66, 74.21, 75.15, 104.36, 114.15, 114.33, 116.91, 121.51, 123.71, 124.89, 127.25, 128.09, 129.39, 130.50, 131.30, 131.68, 134.69, 134.85, 135.40, 177.11.

Synthesis of 7

7

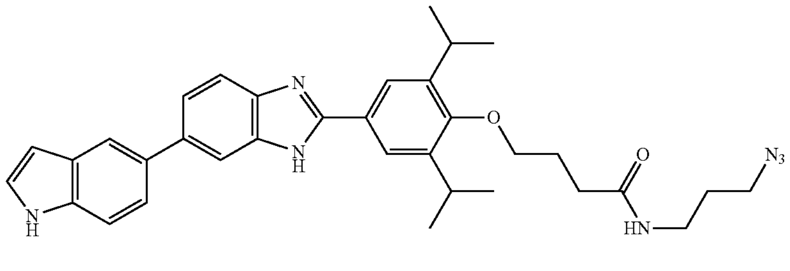

Approximately 40 μmole of 10 was dissolved in 3 mL of ethanol and was supplemented with 10% (w/w) Pd/C. Hydrogenation was performed using a shaker hydrogenation apparatus (Parr Instrument Company, IL) with constant supply of hydrogen gas at 20 psi. The reaction was shaken at room temperature overnight to afford the diamine compound (4'-(4-methylpiperazin-1-yl)-[1,1'-biphenyl]-3,4-diamine (20). The reaction was then immediately supplemented with a solution of 50% ethanol in water containing 1.2 equivalents of sodium metabisulfite and 1.2 equivalents of 4-(4-formyl-2,6-diisopropylphenoxy)butanoate (16). The reaction was heated to reflux overnight to afford the benzimidazole ester derivative (23). Solvent was then removed by rotatory evaporation at reduced pressure and the product was isolated by column chromatography using a gradient of 0-100% ethyl acetate in n-hexanes.

Approximately 20 μmoles of 23 was dissolved in 2.4 mL solution of 3:1 THF:water. The solution was then supplemented with 1.2 equivalents of KOH. The reaction mixture was refluxed overnight to afford the carboxylic acid. After complete conversion to the carboxylic acid product was confirmed by TLC and mass spectrometry, the reaction mixture was quenched by adding an aliquot of 5% HCl solution until the pH was between 5 and 6. Aqueous and organic solvent was removed by rotary evaporation at reduced pressure. To the dried carboxylic acid product, a 3 mL solution of 2 equivalents of 3-azido-propylamine, 2 equivalents of EDC, and 2 equivalents of HOBT in anhydrous DMF was added. The reaction mixture was stirred overnight at room temperature to afford the final product of benzimidazole derivative, 7, containing an azido group. Solvent was then removed by rotatory evaporation at reduced pressure and the product was isolated by column chromatography using a gradient of 0-100% ethyl acetate in DCM (Yield: approx. 5 mg, ~20% overall). (see Scheme 9 below)

Characterization of 23: MS-ESI (+) HRMS: Calculated: ($C_{33}H_{37}N_3O_3$) 524.2913 ($M+H^+$); observed: 524.2905 ($M+H^+$). $^1H$ NMR: ($CDCl_3$, 400 MHz) δ1.23 (12H, d, J=7 Hz), 1.29 (3H, t, J=7 Hz), 2.11 (2H, m), 2.56 (2H, t, J=7H), 3.19 (2H, m), 3.66 (2H, t, J=6 Hz), 4.17 (2H, q, J=7 Hz), 6.27 (1H, s), 6.93 (1H, d, J=8 Hz), 6.98 (1H, s), 7.03 (1H, d, J=8 Hz), 7.19 (1H, d, J=8 Hz), 7.46 (2H, m), 7.83 (1H, s), 8.06 (1H, s), 8.60 (1H, s). $^{13}C$ NMR: ($CDCl_3$, 100 MHz) δ 14.23, 23.49, 25.56, 26.85, 30.71, 50.74, 60.63, 73.46, 102.57, 111.24, 111.64, 113.40, 115.51, 118.41, 118.81, 119.10, 121.28, 124.50, 125.07, 125.60, 128.13, 130.32, 131.55, 132.40, 135.33, 140.86, 144.04, 149.21, 157.69, 173.34.

Characterization of 7: MS-ESI (+) HRMS: Calculated: ($C_{34}H_{39}N_7O_2$) 578.3243 ($M+H^+$); observed: 578.3243 ($M+H^+$). $^1H$ NMR: ($CD_3OD$, 400 MHz) δ 1.38 (12H, d, J=7 Hz), 1.81 (2H, m), 2.21 (2H, m), 2.53 (2H, t, J=7 Hz), 3.37-3.50 (4H, m), 3.92 (2H, t, J=6 Hz), 6.56 (1H, dd, J=3, 1 Hz), 7.31 (1H, t, J=2 Hz), 7.42-7.56 (2H, m), 7.82-8.00 (4H, m), 8.02 (1H, s). $^{13}C$ NMR: ($CD_3OD$, 100 MHz) δ 24.15, 27.43, 28.19, 29.81, 33.18, 37.83, 75.52, 102.92, 112.83, 114.69. 120.23, 122.04, 125.42, 127.65, 131.67, 132.32, 133.85, 137.60, 143.70, 145.86, 151.00, 159.63, 175.38.

Synthesis of 8

8

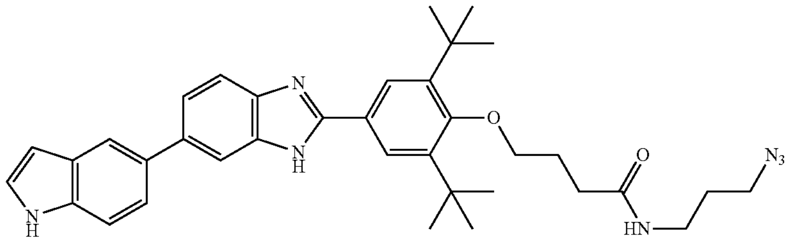

Approximately 40 μmole of 10 was dissolved in 3 mL of ethanol and was supplemented with 10% (w/w) Pd/C. Hydrogenation was performed using a shaker hydrogenation apparatus (Parr Instrument Company, IL) with constant supply of hydrogen gas at 20 psi. The reaction was shaken at room temperature overnight to afford the diamine compound (4'-(4-methylpiperazin-1-yl)-[1,1'-biphenyl]-3,4-diamine (20). The reaction was then immediately supplemented with a solution of 50% ethanol in water containing 1.2 equivalents of sodium metabisulfite and 1.2 equivalents of 4-(4-formyl-2,6-di-tert-butylphenoxy)butanoate (18). The reaction was heated to reflux overnight to afford the benzimidazole ester derivative (24). Solvent was then removed by rotatory evaporation at reduced pressure and the product was isolated by column chromatography using a gradient of 0-100% ethyl acetate in n-hexanes.

Approximately 20 μmoles of 24 was dissolved in 2.4 mL solution of 3:1 THF:water. The solution was then supplemented with 1.2 equivalents of KOH. The reaction mixture was refluxed overnight to afford the carboxylic acid. After complete conversion to the carboxylic acid product as confirmed by TLC and mass spectrometry, the reaction mixture was quenched by adding an aliquot of 5% HCl solution until the pH was between 5 and 6. Aqueous and organic solvent was removed by rotary evaporation at reduced pressure. To the dried carboxylic acid product, a 3 mL solution of 2 equivalents of 3-azido-propylamine, 2 equivalents of EDC, and 2 equivalents of HOBT in anhydrous DMF was added. The reaction mixture was stirred overnight at room temperature to afford the final product of benzimidazole derivative, 8, containing an azido group. Solvent was then removed by rotatory evaporation at reduced pressure and the product was isolated by column chromatography using a gradient of 0-100% ethyl acetate in DCM (Yield: approx. 5 mg, ~20% overall). (see Scheme 10 below)

Characterization of 24: MS-ESI (+) HRMS: Calculated: ($C_{35}H_{41}N_3O_3$) 552.3236 ($M+H^+$); observed: 552.3235 ($M+H^+$). $^1H$ NMR: ($CDCl_3$, 400 MHz) δ 1.27 (3H, t, J=7 Hz), 1.39 (18H, s), 2.16 (2H, m), 2.43 (2H, t, J=7 Hz), 3.61 (2H, t, J=7 Hz), 4.15 (2H, q, J=7 Hz), 6.26 (1H, s), 7.01 (3H, m), 7.27 (1H, m), 7.54 (2H, m), 7.96 (1H, s), 8.15 (2H, s), 8.59 (1H, s). $^{13}C$ NMR: ($CDCl_3$, 100 MHz) δ14.20, 24.73, 30.59, 31.64, 36.20, 60.70, 75.53, 102.58, 111.27, 117.14, 119.14, 121.29, 125.09, 126.85, 128.16, 130.42, 131.66, 132.56, 135.33, 140.91, 145.90, 149.51, 162.62, 173.06.

Characterization of 8: MS-ESI (+) HRMS: Calculated: ($C_{36}H_{43}N_7O_2$) 606.3556 ($M+H^+$); observed: 606.3552 ($M+H^+$). $^1H$ NMR: ($CD_3OD$, 400 MHz) δ 1.56 (18H, s), 1.77 (2H, m), 2.56 (2H, m), 2.38 (2H, t, J=8 Hz), 3.27 (2H, t, J=7 Hz), 3.37 (2H, t, J=7 Hz), 3.85 (2H, t, J=7 Hz), 7.32 (1H, s), 7.47 (2H, m), 7.80-8.00 (4H, m), 8.13 (1H, s). $^{13}C$ NMR: ($CD_3OD$, 100 MHz) δ 26.70, 29.75, 32.37, 32.96, 37.39, 37.83, 50.12, 77.53, 112.19, 112.81, 114.69, 118.77, 120.15, 122.03, 127.85, 130.10, 131.91, 132.37, 134.04, 137.57, 143.50, 147.57, 151.22, 164.20, 175.06.

Section 2: Synthesis and Characterization of Fluorescein Conjugates of 1, 2, 3 and 4

Synthesis of Fluorescein Conjugates (FL) of Compounds 1, 2, 3 and 4: Fluorescein conjugates (FL) for compound 1, 2, 3, and 4 were synthesized as previously described.[1] A 4 μmol sample of N-(2-propynyl) 5-fluoresceincarboxamide (FL) was added to a solution in methanol containing 1 μmol compound (1, 2, 3, or 4), 0.25 μmol $CuSO_4$, and 0.75 μmol freshly dissolved ascorbic acid. The final volume of the reaction was brought to 0.5 mL with methanol. The reaction mixture was stirred at room temperature for 4 h. The crude reaction mixture was then purified by reverse phase HPLC using a linear gradient of 20% to 100% B in A over 60 min [A is 0.1% (v/v) TFA in water and B is 0.1% (v/v) TFA in methanol]. The purity of the product was evaluated on a Waters Symmetry C18 5 μm 4.6×150 mm column using a Waters 1525 binary HPLC pump equipped with a Waters 2487 dual A absorbance detector system. Separations were completed at room temperature using a 1 mL/min flow rate and a linear gradient of 0% to 100% B in A over 70-100 min. Absorbance was monitored at 220 nm and 254 nm. All fluorescein conjugated compounds were ≥95% pure.

HRMS: calculated mass for 1-FL: ($C_{55}H_{51}N_9O_8$) 966.3939 (M+H), observed mass: 966.3939 (M+H), 483.7052 (M+2H/2); calculated mass for 2-FL: ($C_{57}H_{55}N_9O_8$) 994.4252 (M+H), observed mass: 994.4251 (M+H), 497.7213 (M+2H/2), 332.1525 (M+3H/3); calculated mass for 3-FL: ($C_{61}H_{63}N_9O_8$) 1050.4878 (M+H), observed mass: 1050.4877 (M+H), 525.7475 (M+2H/2), 350.8349 (M+3H/3); calculated mass for 4-FL: ($C_{63}H_{67}N_9O_8$) 1078.5191 (M+H), observed mass: 1078.5184 (M+H) 539.7625 (M+2H/2), 360.1775 (M+3H/3). Yields for 4-FL, 3-FL, 2-FL and 1-FL were 37%, 41%, 38%, and 45%, respectively.

Synthesis of 4-CA-Biotin and Control-CA-Biotin: 4-CA-Biotin and Control-CA-Biotin was synthesized via standard resin-supported oligomerization protocol. Fmoc-protected rink amide resin (200 mg, 138 μmol) with a substitution level of 0.69 mmol/g was allowed to swell for 5 min each in DCM and DMF with shaking. The resin was deprotected with 20% piperidine in DMF (3 mL, 2×20 min) at room temperature.

Coupling step: The resin was then washed with DMF (3×5 min). Bromoacetic acid was coupled to the resin bound amine in the presence of 5 equivalents of bromoacetic acid and 5 equivalents of DIC in 3 mL dDMF. The reaction mixture was heated in a Panasonic microwave at 10% power (70 watts) (2×30 s). The resin was then washed with dDMF (3×5 min).

Displacement step: The resin was then treated with 3 equivalents of biotin ethylene diamine (0.69 mmol) in 3 mL of DMF in a Panasonic microwave at 10% power (70 watts) (1×30 s) and shaken at room temperature for 2 h. Coupling with bromoacetic acid was repeated after the introduction of biotin ethylene diamine. The resin was then treated with 5 equivalents of Boc-ethylene diamine (0.69 mmol) in 3 mL of DMF in a Panasonic microwave at 10% power (70 watts) (1×30 s) and shaken at room temperature for 20 min. The resin was then washed with dDMF (3×5 min).) 4-carboxylate was coupled to the end of the peptoid backbone. The peptoid (50 mg, 34.5 μmol) from the previous step was directly treated with a solution of 4-carboxylate (35 mg, 52 μmol), EDC (8 mg, 52 μmol), HOAT (7 mg, 52 μmol) and DIEA (66 μL, 345 μmol) in 2 mL dDMF in a microwave vial in a Biotage Initiator+ at 75° C. for 2 h. Alternatively the resin was treated either with 100 μL 1:1 mixture of acetic anhydride and DIEA in 3 mL dDMF for 5 min and then washed with DMF for Control CA-Biotin compound. The resin was then washed with DMF (3×5 min) followed by DCM (3×5 min) before cleaving the peptoid off the resin in (1:1) TFA:DCM for 15 min at room temperature. The solvent was removed under vacuum and the crude product was purified via HPLC. The product was purified by preparative HPLC using a reverse phase SunfirePrep C18 5 μM 19×150 mm column. HPLC separations were completed using a Waters 1525 Binary HPLC Pump equipped with a Waters 2487 Dual Absorbance Detector system. A linear gradient from 0% to 100% B in A over 60 min and a flow rate of 5 mL/min were employed. (A: water+0.1% (v/v) trifluoroacetic acid (TFA); B: acetonitrile+0.1% (v/v) TFA). Chlorambucil (CA) was then coupled using HOAT (3 mg, 15 μmol), HATU (5.5 mg, 15 μmol) and DIEA (10 μL, 50 μmol) in 200 μL dDMF at RT for overnight to obtain either 4-CA-Biotin or Control-CA-Biotin. The purity was evaluated on a reverse phase Waters Sunfire C18 3.5 μm 4.6×150 mm column at room temperature. A flow rate of 1 mL/min and a linear gradient of 0-100% B in A. Absorbance was monitored at 254 and 220 nm. 4-CA-Biotin and Control-CA-Biotin were ≥95% pure (see Scheme 11 below).

Section 3: Methods for Construction of Small Molecule Microarrays and 2DCS Selections Construction of Alkyne-Displaying Microarrays: Microarrays were constructed as described previously.[1] Briefly, a 1 mL aliquot of a 1% molten agarose solution was applied to a microscope slide (Fisher Scientific, Superfrost) and the agarose was allowed to dry to a thin film at room temperature overnight. The agarose was then oxidized by submerging the slides in 20 mM sodium periodate ($NaIO_4$) for 30 min followed by washing with water (3×30 min). Residual $NaIO_4$ was removed by incubating the slides in 10% aqueous ethylene glycol for 1.5 h at room temperature and washing with water (3×30 min). Slides were then incubated with 20 mM propargylamine in 0.1 M $NaHCO_3$ for 2 h and reduced with $NaCNBH_3$ in a solution containing 40 mL of 1× phosphate-buffered saline and 10 mL ethanol for 10 min.

Construction of Small Molecule Microarrays: Azido-small molecule derivatives were spotted onto alkyne-functionalized slides in 100 μM tris(benzyltriazolylmethyl)amine (TBTA; dissolved in 4:1 butanol/dimethyl sulfoxide (DMSO)), 1 mM $CuSO_4$, 1 mM ascorbic acid, and 70% DMSO. The slides were placed into a humidity chamber for 2 h and washed with water (3×30 min) and then dried at room temperature.

RNA Screening and Selection. 2DCS selections were completed as previously described.[2] All oligonucleotides, including 5'-end $^{32}$P-labeled 3×3 ILL (100 μmol) prepared as described,[2] competitor chase oligonucleotides (FIG. 1, 10 nmol each) and tRNA (10 nmol), were folded separately in 1× Hybridization Buffer [HB1: 20 mM HEPES, pH 7.5, 150 mM NaCl and 5 mM KCl] by heating at 60° C. for 5 min followed by cooling to room temperature on the bench top. $MgCl_2$ was then added at 1 mM final concentration. The folded RNAs were mixed together and 40 μg/mL bovine serum albumin (BSA) was added in a total volume of 500 μL. Prior to hybridization, microarrays were pre-equilibrium with 500 μL of HB1 supplemented with 1 mM $MgCl_2$ and 40 μg/mL BSA [HB2] for 10 min at room temperature to prevent non-specific binding. After the slides were pre-equilibrated, HB2 was removed and the mixture of folded RNAs was applied to the microarray surface and distributed evenly across the array surface with a custom-cut piece of Parafilm. The slide was hybridized for approximately 30 min at room temperature. After incubation, the Parafilm was removed and the slide was washed by submersion in 30 mL of HB2 for 10 min with gentle agitation three times. Excess buffer was removed completely from the slide, and the slide was dried at room temperature for 30 min. The microarray was exposed to a phosphorimager screen and imaged using a Molecular Devices Typhoon phosphorimager.

The image was used as a template to harvest bound RNAs from the microarray surface. A 0.2 μL aliquot of HB1 was added to each spot. After 30 s, the buffer was absorbed and the agarose gel at that spot was excised using a toothpick.

Section 4: Frequency Rank and $Z_{obs}$ Rank Vs. $K_d$ Plots for Compounds 1 and 2

Figure 11:
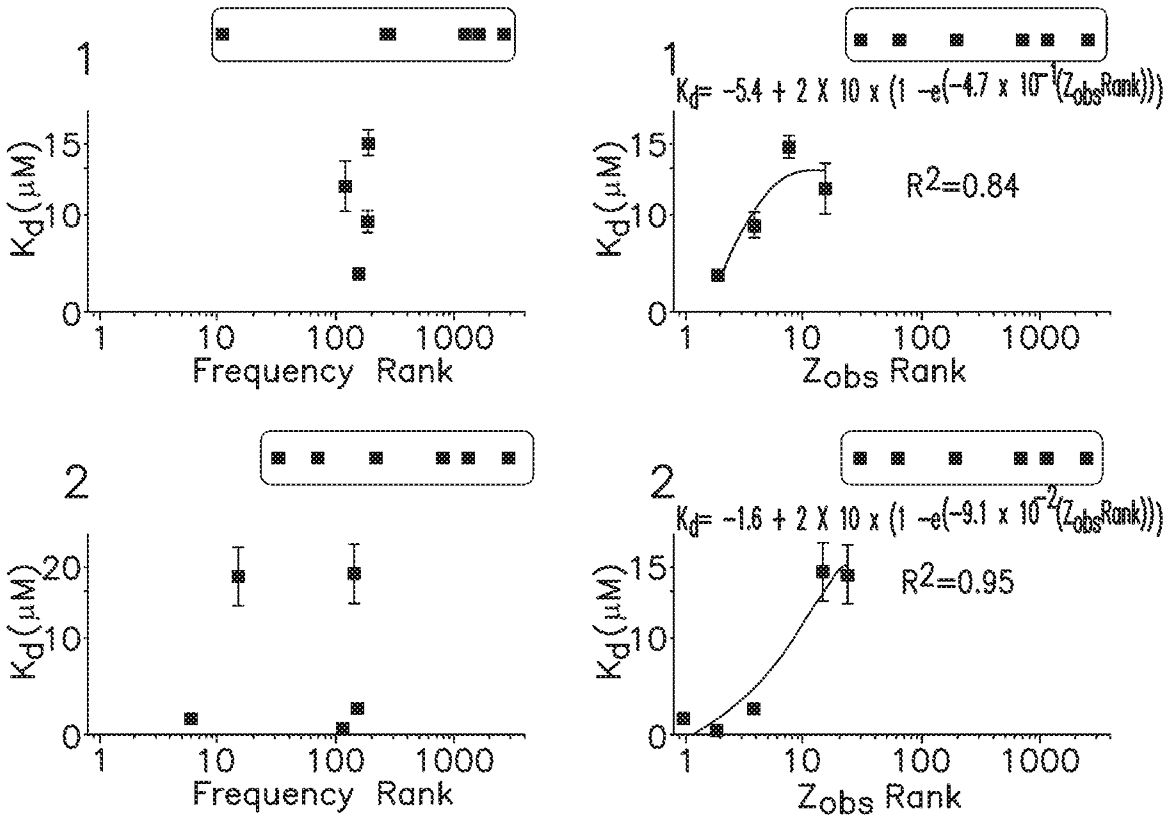
FIG. 11: Correlating sequencing data with ligand affinity using the sequencing data of RNA motifs that bind compounds 1 and 2. Data points in the box are interactions that do not exhibit saturable binding. Top, analysis of the selected RNA motifs that bind compound 1. Top left and top right are plots of affinity as a function of Frequency Rank and $Z_{obs}$ Rank, respectively. Bottom, analysis of the selection of RNA motifs that bind to compound 2. Bottom left and bottom right are plots of affinity as a function of Frequency Rank and $Z_{obs}$ Rank, respectively. Good correlation is only observed between $Z_{obs}$ Rank and affinity of the complexes.

See FIG. 11, below.

Scheme 3

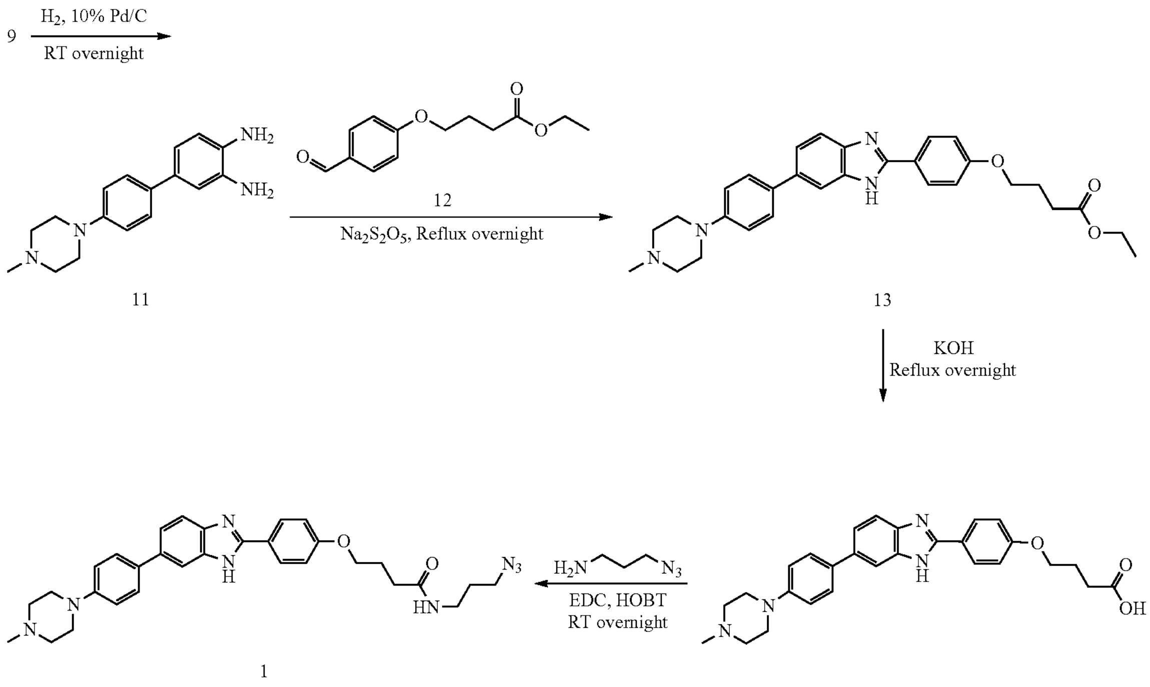

Scheme 4
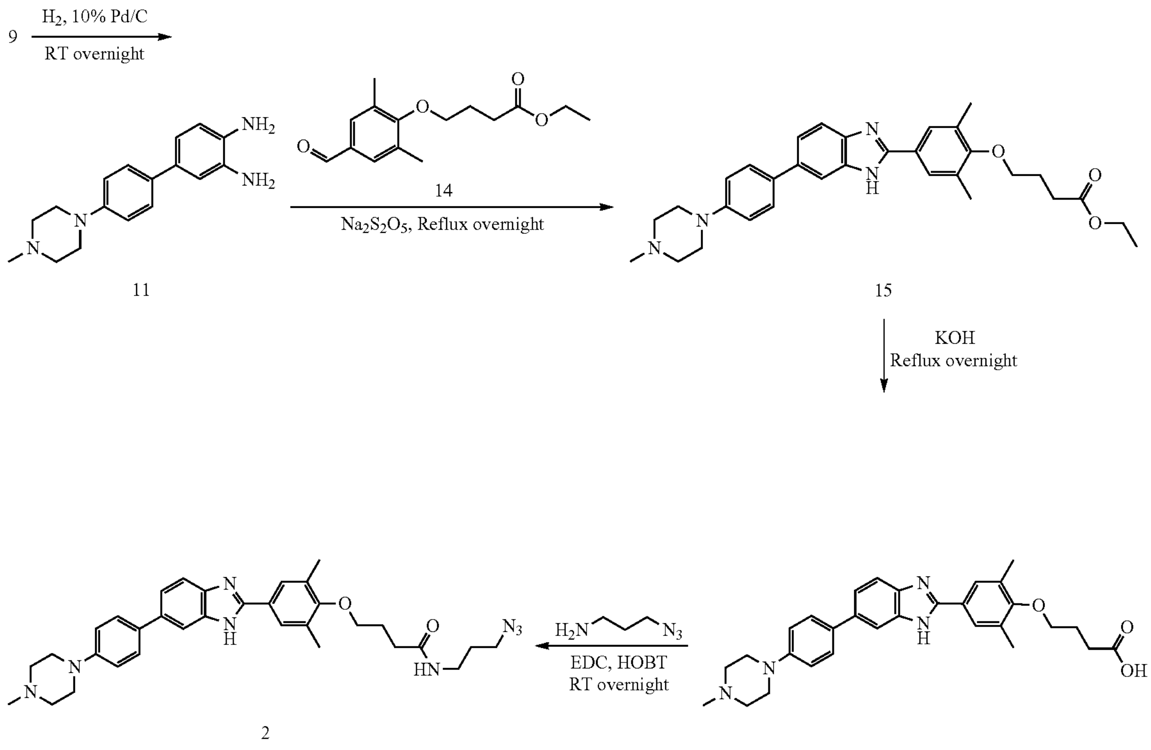
Scheme 5
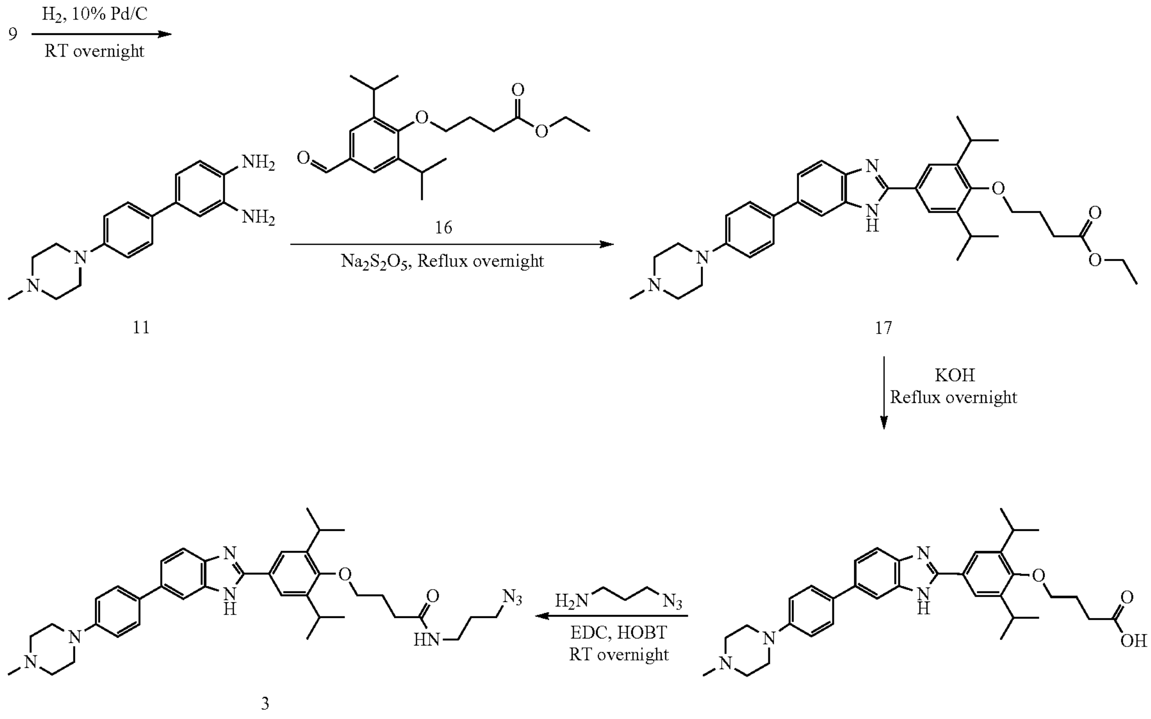

Scheme 6
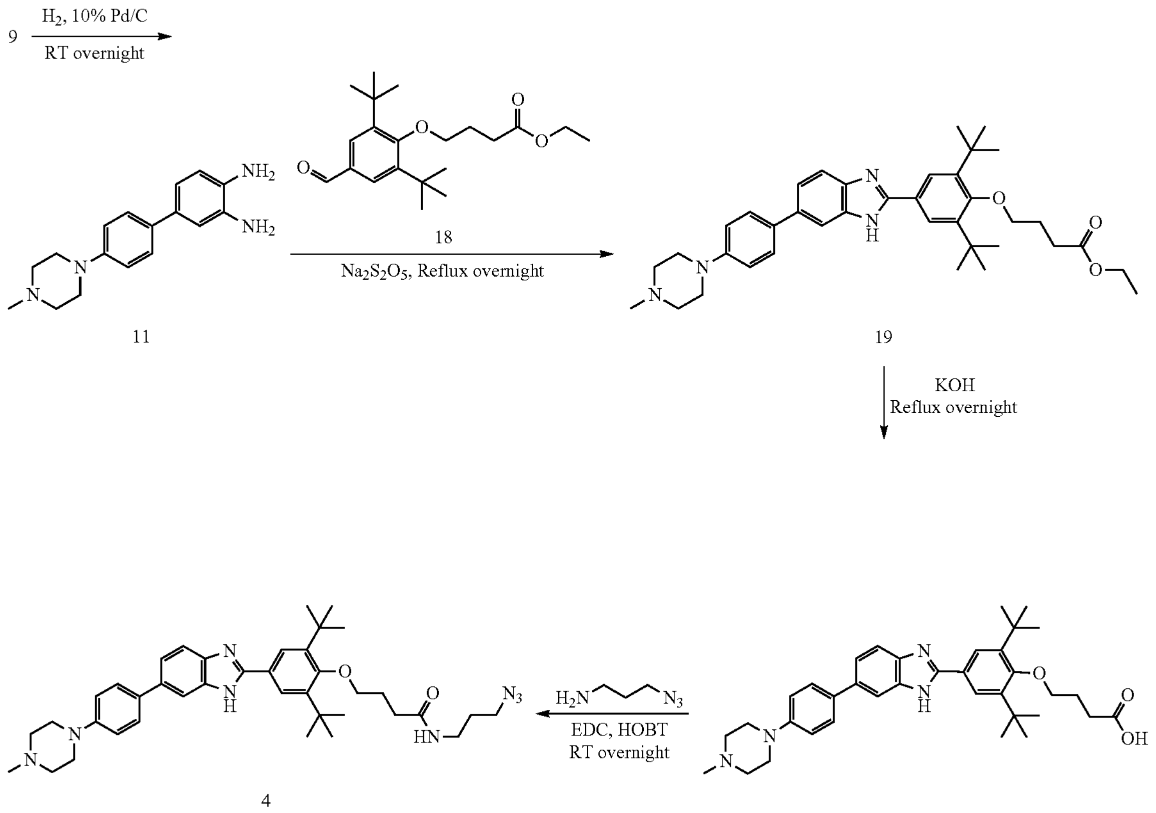
Scheme 7
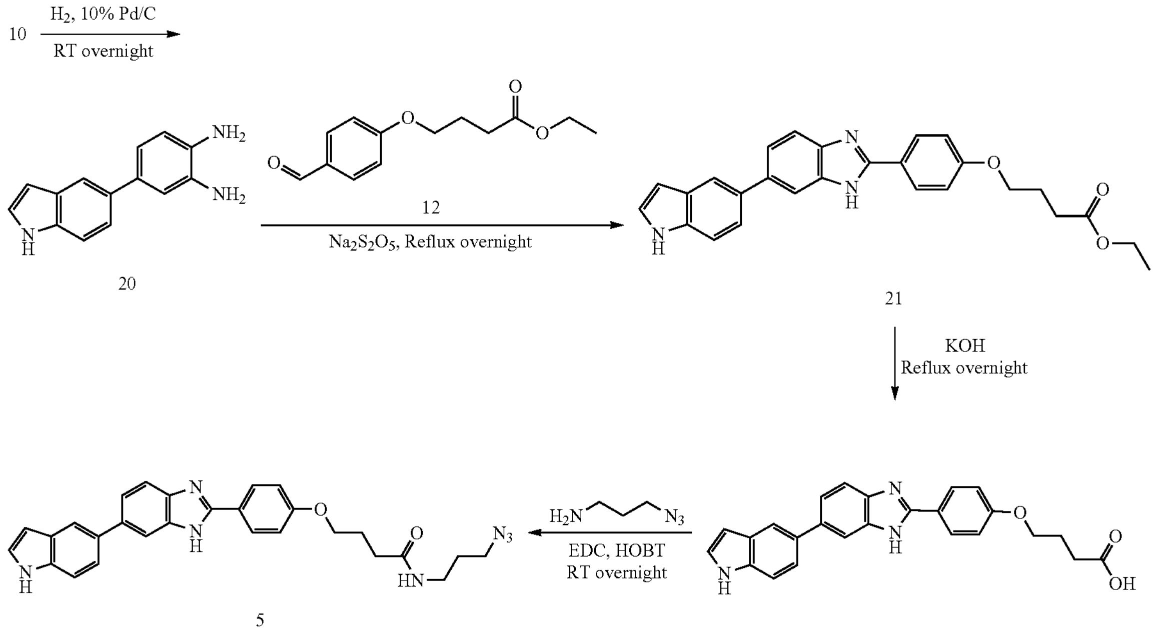

Scheme 8
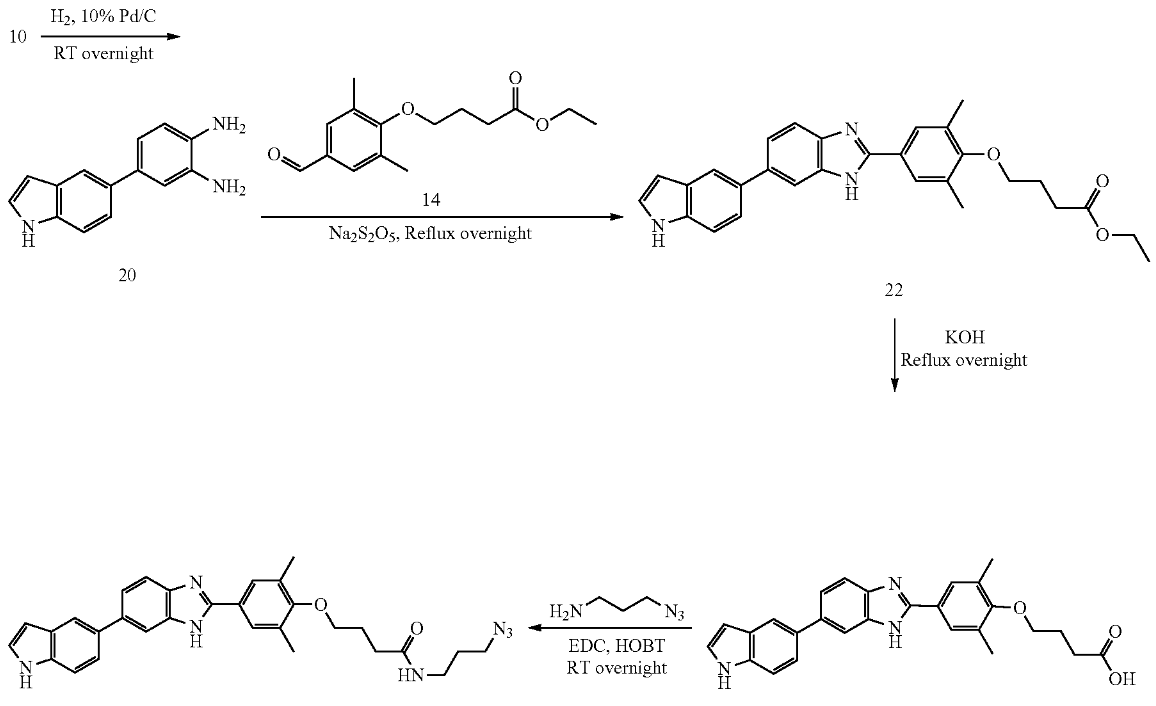
10 20 14 22 6
Scheme 9
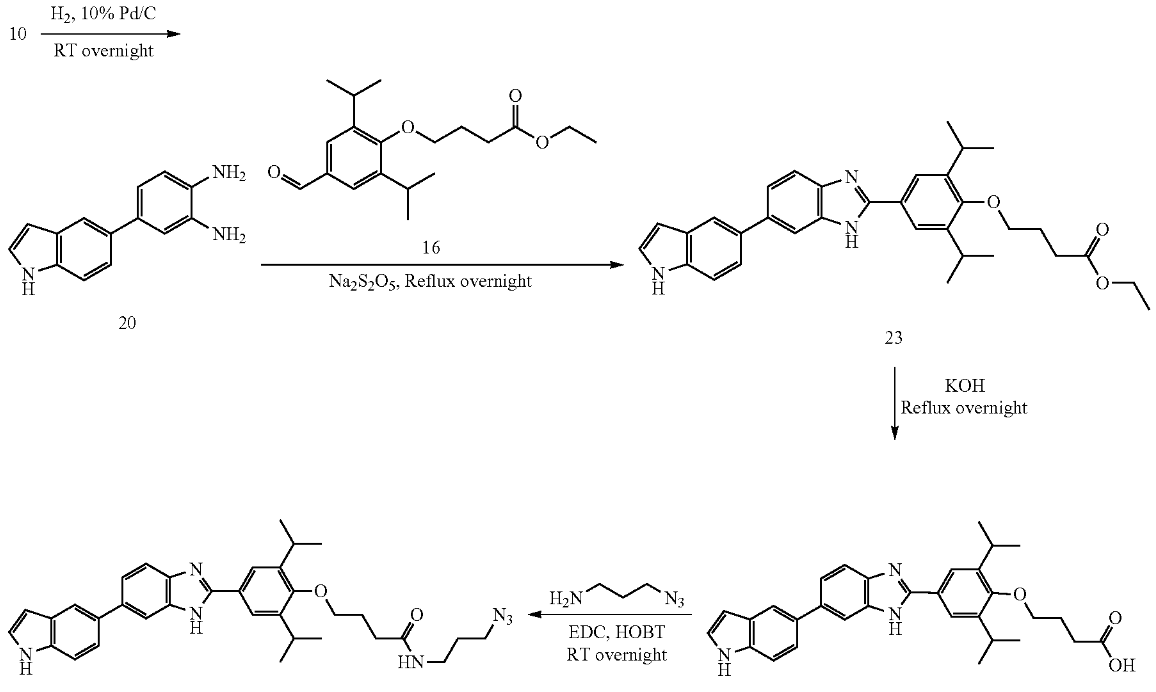
10 20 16 23 7

Scheme 10
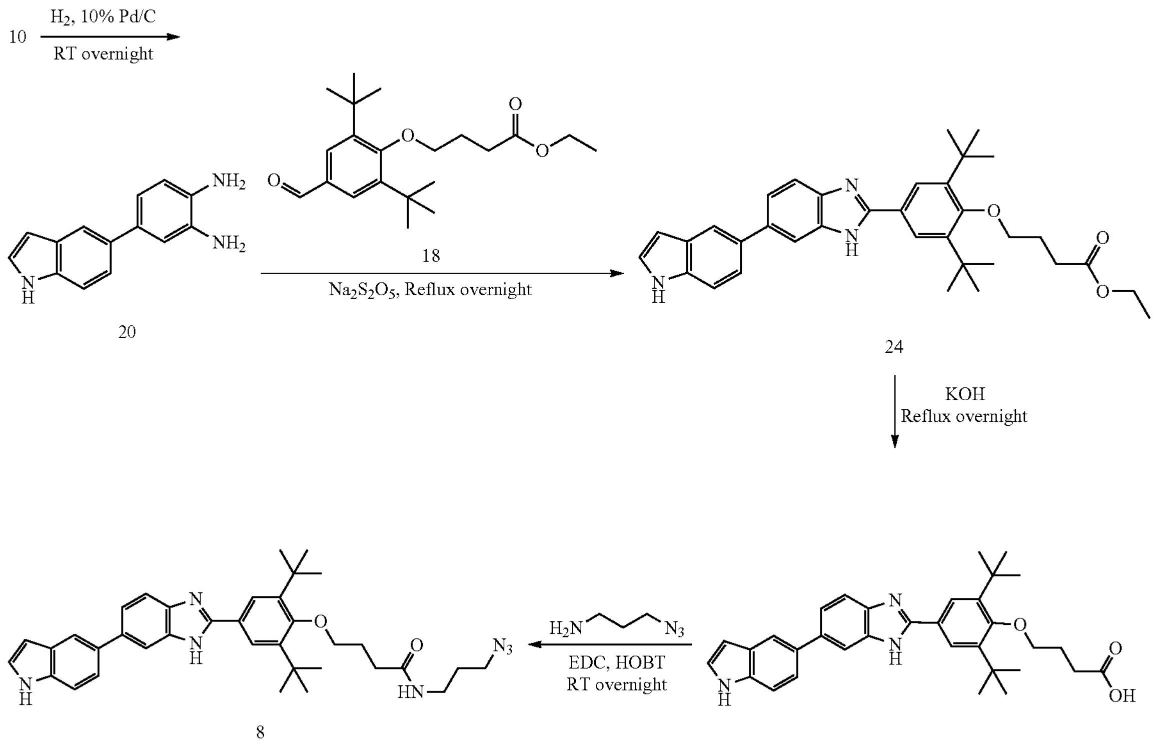
Scheme 11
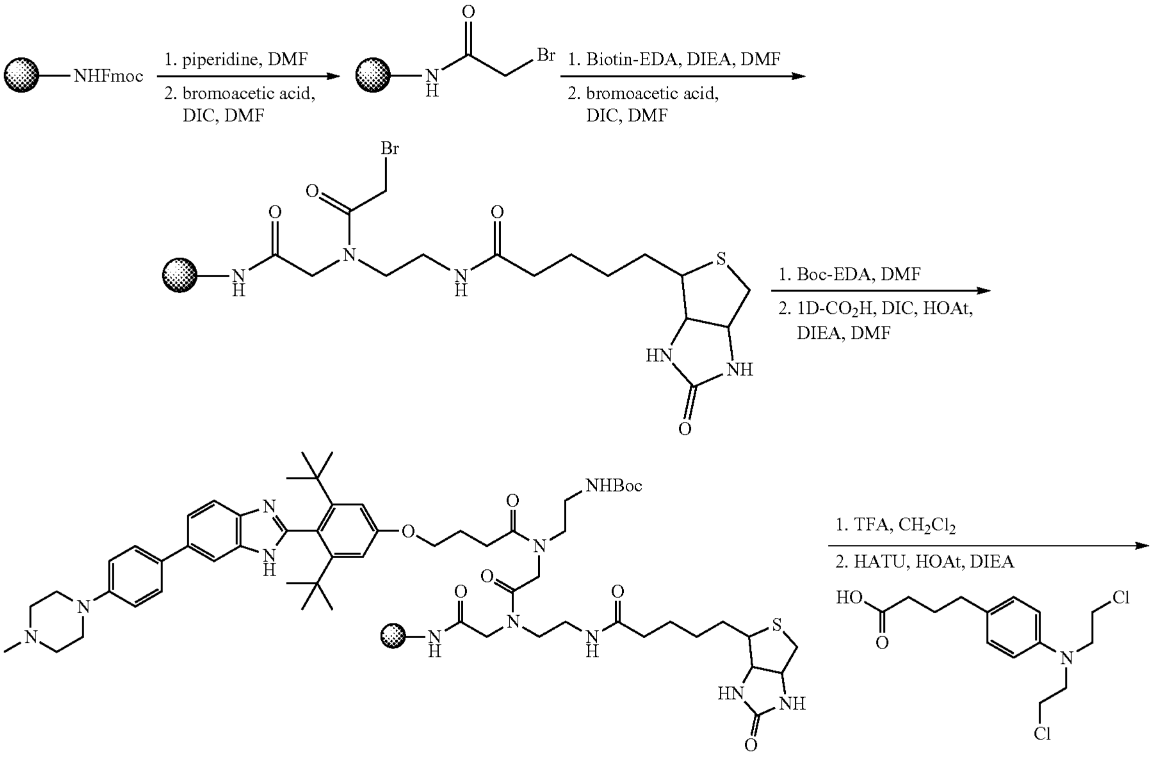

-continued

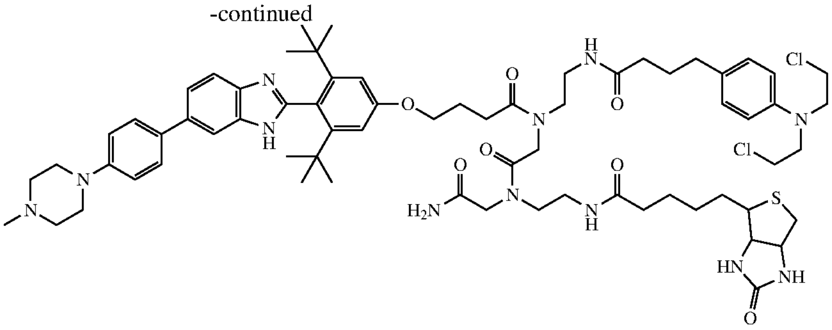

General Nucleic Acids: All DNA oligonucleotides were purchased from Integrated DNA Technologies, Inc. (IDT) and used without further purification. The RNA competitor oligonucleotides were purchased from Dharmacon and deprotected according to the manufacturer's standard procedure. Competitor oligonucleotides were used to ensure that RNA-small molecule interactions were confined to the randomized region (3×3 or 3×2 nucleotide internal loop pattern; FIG. 1). All aqueous solutions were made with NANOpure water. The RNA library was transcribed by in vitro transcription from the corresponding DNA template (see below).

PCR Amplification of DNA Templates Encoding 3×3 ILL and 3×2 ILL (RNA Motif Library) & Selected RNAs: The DNA templates encoding selected RNAs and 3×3 ILL or 3×2 ILL were PCR amplified using a forward primer that encodes for a T7 RNA polymerase promoter. PCR amplification was completed in 300 μL of 1×PCR buffer (10 mM Tris-HCl, pH 9.0, 50 mM KCl and 0.1% Triton X-100), 4.25 mM $MgCl_2$, 0.33 mM dNTPs, 2 μM each primer (forward primer: 5'-d(GGCCGGATCCTAATACGACTCACTATAGGGAGAGGGTTTAAT) (SEQ ID NO: 37) and reverse primer: 5'-d(CCTTGCGGATCCAAT) (SEQ ID NO: 38)) and 1 μL of Taq DNA polymerase. The DNA was amplified by 30 cycles of 95° C. for 30 s, 50° C. for 30 s, and 72° C. for 40 s. All PCR reactions were evaluated on a 2% agarose gel stained with ethidium bromide prior to transcription.

RNA Transcription and Purification: RNAs were transcribed as previously described.[48] Briefly, transcriptions were completed in at total volume of 1 mL containing 1× Transcription Buffer (40 mM Tris-HCl, pH 8.0, 1 mM spermidine, 10 mM DTT, and 0.001% Triton X-100), 2.5 mM each rNTP, 15 mM $MgCl_2$, 300 μL of PCR-amplified DNA template, and 20 μL of 20 mg/mL T7 RNA polymerase by incubating at 37° C. overnight. After transcription, 1 unit of DNase I (Invitrogen) was added, and the sample was incubated at 37° C. for additional 30 min. Transcribed RNAs were then purified on a denaturing 12.5% polyacrylamide gel and extracted as previously described.[48] Concentrations were determined by measuring absorbance at 260 nm and the corresponding extinction coefficients, which were determined by the HyTher server[49] and nearest neighbor parameters.[50]

RNA Screening and Selection. 2DCS selections were completed as previously described.[18] Please see the Supporting Information for experimental details.

Reverse Transcription and PCR Amplification to Install Barcodes for RNA-seq. The agarose containing bound RNAs excised from 2DCS arrays was placed into a thin-walled PCR tube with 18 μL of water, 2 μL of 10×RQ DNase I buffer and 2 units of RNase-free DNase (Promega). The solution was incubated at 37° C. for 2 h and then quenched by addition of 2 μL of 10× DNase stop solution (Promega, Madison, WI). Samples were incubated at 65° C. for 10 min to completely inactivate the DNase and then subjected to RT-PCR amplification to install a unique barcode. Reverse transcription reactions were completed in 1×RT buffer, 1 mM dNTPs, 5 μM RT primer (5'-CCTCTCTATGGGCAGTCGGTGATCCTTGCGGATCCAAT; (SEQ ID NO: 39) the sequence underlined is complementary to 3' end of the RNAs), 200 μg/mL BSA, 4 units of reverse transcriptase, and 20 μL of DNase-treated selected RNAs. Samples were incubated at 60° C. for 1 h. A 20 μL aliquot of the RT reaction was added to 6 μL of 10×PCR Buffer, 4 μL of 100 μM forward primer including barcode (5'-CCATCTCATCCCTGCGTGTCTCCGACTCAGXXXXXXXXXXGATGGGAGAGGGTTTAAT (SEQ ID NO: 40) where X represents unique barcode, GAT is the barcode adapter, and the sequence underlined is complementary to 5' end of the library), 2 μL of 100 μM reverse primer, 0.6 μL of 250 mM $MgCl_2$, and 2 μL of Taq DNA polymerase. Two-step PCR was performed at 95° C. for 1 min and 72° C. for 1 min. Aliquots of the RT-PCR product were checked every three cycles starting at cycle 10 on a denaturing 12.5% polyacrylamide gel stained with ethidium bromide to ensure that background spots (excised from the array where compound was not delivered) were not amplified. RT-PCR products encoding selected RNAs were purified on a denaturing 12.5% polyacrylamide gel. Purity was assessed by a Bioanalyzer. Samples were mixed in equal amount and sequenced using an Ion Proton deep sequencer using PI chips (60-80 million reads).

Assigning Frequency, Frequency Rank, $Z_{obs}$, and $Z_{obs}$ Rank from the Output of Next-Generation Sequencing. A shell script was written to process the fastq sequencing files generated by Scripps' Genomics Core. Shell functions such a grep and awk were used to find matching sequences to the 3×3 ILL or 3×2 ILL and to extract the randomized loop region in the library. Frequency of the randomized loops was calculated using awk.

Calculating Statistical Significance ($Z_{obs}$) for Selected RNAs: To determine if the difference in frequency for given RNA in the starting library and in the selection was statistically significant, a pooled population comparison ($Z_{obs}$) was calculated using equations (1) and (2):

$$\Phi = \frac{(n_1 p_1 + n_2 p_2)}{n1 + n2} \tag{1}$$

$$Z_{obs} = \frac{(p_1 - p_2)}{\sqrt{\Phi(1-\Phi)\left(\frac{1}{n_1} + \frac{1}{n_2}\right)}} \tag{2}$$

Where $n_1$ is the size of population 1 (number of reads for a selected RNA); $n_2$ is the size of population 2 (number of reads for the same RNA from sequencing of the starting library); $p_1$ is the observed proportion of population 1 (number of reads for a selected RNA divided by the total number of reads); $p_2$ is the observed proportion for population 2 (number of reads for the same RNA divided by the total number of reads in the starting library).

Binding Affinity Measurements: An in solution, fluorescence-based assay was used to determine binding affinities by monitoring the change in fluorescence intensity of 1-FL (or 2-FL/3-FL/4-FL) as a function of RNA concentration as described previously.[18] Briefly, the RNA of interest was folded in 1× Folding Buffer (8 mM $Na_2HPO_4$, pH 7.0, 185 mM NaCl and 1 mM EDTA) by heating at 60° C. for 5 min followed by slowly cooling to room temperature on the bench top. Then, the FL-conjugated compound was added into the RNA solution to a final concentration of 100 nM. Serial dilutions were then completed using 1× Folding Buffer supplemented with 100 nM FL-conjugated compound. The solutions were incubated at room temperature for 30 min and then transferred to a well of a black 384-well plate. Fluorescence intensity was measured using a Bio-Tek FL×800 plate reader with an excitation wavelength of 485/20 nm and an emission wavelength of 528/20 nm. The change in fluorescence intensity as a function of the concentration of RNA was fit to equation 3:[9]

$$I=I_0+0.5\,\Delta\varepsilon\{([FL]_0+[\mathrm{RNA}]_0+K_d)-(([FL]_0+[\mathrm{RNA}]_0+K_d)^2-4[FL]_0[\mathrm{RNA}]_0)^{1/2}\} \quad (3)$$

where I is the observed fluorescence intensity; $I_0$ is the fluorescence intensity in the absence of RNA; Δε is the difference between the fluorescence intensity in the absence of RNA and in the presence of infinite RNA concentration; $[FL]_0$ is the concentration of compound; $[RNA]_0$ is the concentration of the selected RNA; and $K_d$ is the dissociation constant.

Competitive binding assays were completed by incubating the RNA of interest with 100 nM 4-FL and increasing concentrations of 4. The resulting curves were fit to equation 4:

$$\theta=\frac{1}{2[4-FL]}[K_t+\frac{K_t}{K_d}[C_t]+[\mathrm{RNA}]+[4-FL]-\sqrt{\left(K_t+\frac{K_t}{K_d}+[C_t]+[\mathrm{RNA}]+[4-FL]\right)^2-4[4-FL][\mathrm{RNA}]}+A$$

where θ is the percentage of 4-FL bound, [4-FL] is the concentration of 4-FL, $K_t$ is the dissociation constant of RNA and 4-FL, [RNA] is the concentration of RNA, $C_t$ is the concentration of 4, $K_d$ is the dissociation constant for 4, and A is a constant.

Dicer Inhibition Assay: The template used for pre-miR-18a (5'-GGGTGTTCTAAGGTGCATCTAGTGCAGATAGTGAAGTAGATTAGCATCTACTGCCCTAAGT GCTCCTTCTGGCA) (SEQ ID NO: 41) was PCR-amplified in 1×PCR Buffer, 2 μM forward primer (5'-GGCCGAATTCTAATACGACTCACTATATCT-AAGGTGCATCTAGTGCAGA) (SEQ ID NO: 42), 2 μM reverse primer (5'-TGCTACAAGTGCCTTCACTGCA) (SEQ ID NO: 43), 4.25 mM $MgCl_2$, 330 μM dNTPs, and 2 μL of Taq DNA polymerase in a 50 μL reaction. Cycling conditions were 95° C. for 30 s, 55° C. for 30 s, and 72° C. for 60 s. Pre-miR-18a was 5'-end labeled with $^{32}P$ as previously described.[9] The RNA was folded in 1× Reaction Buffer (Genlantis) by heating at 60° C. for 5 min and slowly cooling to room temperature. The samples was then supplemented with 1 mM ATP and 2.5 mM $MgCl_2$. Serially diluted concentrations of 4 were added and the samples were incubated at room temperature for 15 min. Next, 0.005 units/μL of recombinant human Dicer (Genlantis) were added followed by incubation at 37° C. overnight. Reactions were stopped by adding the manufacturer's supplied stop solution.

A T1 ladder (cleaves G residues) was generated by heating the RNA in 1×RNA Sequencing Buffer (20 mM sodium citrate, pH 5.0, 1 mM EDTA, and 7 M urea) at 55° C. for 10 min followed by slowly cooling to room temperature. RNase T1 was then added to a final concentration of 3, 0.3, 0.03 units/μL and the solution was incubated at room temperature for 20 min. An RNA hydrolysis ladder was generated by incubating RNA in 1×RNA hydrolysis buffer (50 mM $NaHCO_3$, pH 9.4, and 1 mM EDTA) at 95° C. for 5 min. In all cases, cleavage products were separated on a denaturing 15% polyacrylamide gel and imaged using a Bio-Rad PMI phosphorimager.

Cell Culture: DU145 cells were cultured in growth medium (Roswell Park Memorial Institute medium (RPMI) supplemented with 10% fetal bovine serum (FBS)) at 37° C. and 5% $CO_2$ RNA Isolation and Quantitative Real Time Polymerase Chain Reaction (qRT-PCR) of miRNAs: DU145 cells were transfected in either 6- or 12-well plates with a miR-17-92 cluster overexpression plasmid (Addgene plasmid #21109)[51] with jetPRIME per manufacturer's suggested protocol for 24 h. Total RNA was extracted from cells using a Quick-RNA Miniprep Kit (Zymo Research) per the manufacturer's protocol. Approximately 200 ng of total RNA was used in reverse transcription (RT) reactions, which were completed using a miScript II RT kit (Qiagen) per the manufacturer's protocol. RT-qPCR was performed on a 7900HT Fast Real Time PCR System (Applied Biosystem) using power SYBR Green Master Mix (Applied Biosystems). All primer sets were purchased from Integrated DNA Technologies, Inc. (IDT) or Eurofins (Table S1). The expression levels of mature miRNAs were normalized to U6 small nuclear RNA or 18s rRNA.

Reaction of 4-CA-Biotin: To determine if 4-CA-Biotin reacts with the miR-18a hairpin precursor or tRNA in vitro, 5 μL of $^{32}P$-labeled miR-18a hairpin precursor or tRNA (~50,000 cpm) was diluted in a total volume of 300 μL of 1×PBS (10 mM $Na_2HPO_4$, 1.8 mM $KH_2PO_4$, pH 7.4, 137 mM NaCl and 2.7 mM KCl). The RNA was folded by heating at 60° C. for 5 min and slowly cooling to room temperature. Compound was then added at various concentrations, and the solutions were incubated overnight at room temperature. Next, 10 μL of streptavidin resin (high capacity streptavidin agarose beads; Thermo Scientific) was added to the samples, which were incubated for an additional 30 min at room temperature. After centrifugation, the supernatant was removed, and the resin was washed with 1×PBST (1×PBS+0.1% (v/v) Tween 20). The amount of radioactivity in the supernatant, wash, and associated with the beads was measured using a Beckman Coulter LS6500 liquid scintillation counter.

Chem-CLIP in Cell Lysates: DU145 cells were cultured as described above in 100 mm dishes and lysed with 500 μL of Cell Lysis Buffer (10 mM Tris pH 7.4, 0.25% Igepal CA-630 and 150 mM NaCl) for 5 min at room temperature. The cell lysate was then centrifuged and the supernatant collected. Next, 10 μM of 4 was added to the lysate in 1×PBS and the sample was incubated for 2 h at room temperature. The reaction was then directly used for pull-down by incubating with 50 μL of streptavidin resin in 1×PBS for 30 min at room temperature. After centrifugation, the supernatant was removed, and the resin was washed twice with 1×PBS. RNA was eluted from the streptavidin beads by incubation with 100 μL of 1× Elution Buffer (10 mM EDTA and 95% formamide) at 65° C. for 20 min. The eluted RNA was cleaned up using a Quick-RNA Miniprep Kit (Zymo) per the manufacturer's protocol. RT-qPCR was completed as described above using 50 ng of total RNA in the RT reaction. Expression levels were normalized to 18S rRNA.

Western Blotting: Cells were grown in 6-well plates to ~80% confluency in complete growth medium and then incubated with 10 or 20 μM of 4 for 48 h. Total protein was extracted using M-PER Mammalian Protein Extraction Reagent (Pierce Biotechnology) per the manufacturer's recommended protocol. Extracted total protein was quantified using a Micro BCA Protein Assay Kit (Pierce Biotechnology). Approximately 25 μg of total protein was resolved using an 8% SDS-polyacrylamide gel and then transferred to a PVDF membrane.

The membrane was briefly washed with 1× Tris-buffered saline (TBS; 50 mM Tris-CI, pH 7.5. 150 mM NaCl) and blocked with 5% milk in 1×TBST (1×TBS containing 0.05% Tween-20) for 1 h at room temperature. The membrane was then incubated with 1:1000 STK4 primary antibody in 1×TBST containing 5% milk overnight at 4° C. The membrane was washed with 1×TBST and incubated with 1:2000 anti-rabbit IgG horseradish-peroxidase secondary antibody conjugate in 1×TBST for 1 h at room temperature. After washing with 1×TBST, protein expression was quantified using SuperSignal West Pico Chemiluminescent Substrate (Pierce Biotechnology) per the manufacturer's protocol.

The membrane was then stripped using 1× Stripping Buffer (200 mM glycine, 1% Tween-20 and 0.1% SDS, pH 2.2) followed by washing in 1×TBST. The membrane was blocked and probed for β-actin following the same procedure described above using 1:5000 β-actin primary antibody in 1×TBST containing 5% milk overnight at 4° C. The membrane was washed with 1×TBST and incubated with 1:10,000 anti-rabbit IgG horseradish-peroxidase secondary antibody conjugate in 1×TBST for 1 h at room temperature. ImageJ software from the National Institutes of Health was used to quantify band intensities.

What is claimed is:
1. A compound of the formula:
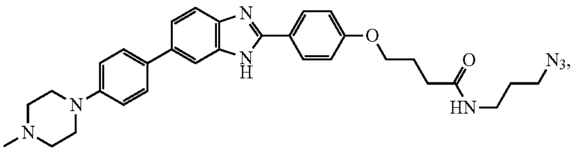
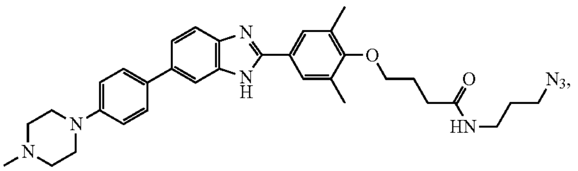
-continued
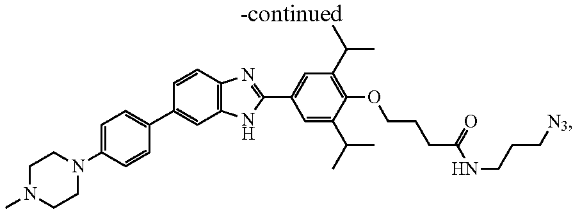
or
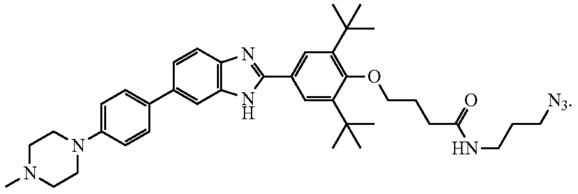
2. The compound of claim 1, wherein the compound is of the formula:
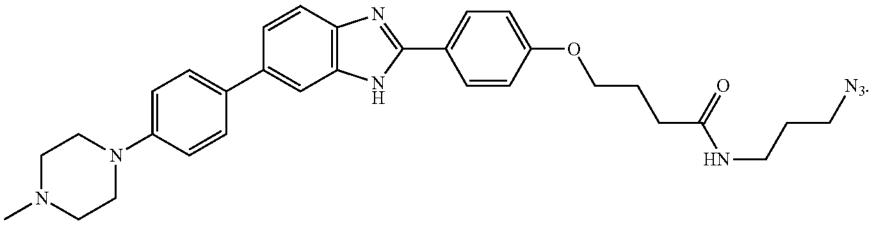 [SMILES: CN1CCN(c2ccc(-c3ccc4nc(-c5ccc(OCCCC(=O)NCCCN=[N+]=[N-])cc5)[nH]c4c3)cc2)CC1]
3. The compound of claim 1, wherein the compound is of the formula:
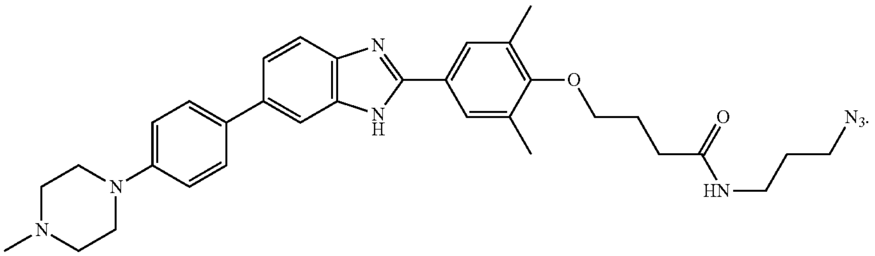 [SMILES: Cc1cc(-c2nc3ccc(-c4ccc(N5CCN(C)CC5)cc4)cc3[nH]2)cc(C)c1OCCCC(=O)NCCCN=[N+]=[N-]]

4. The compound of claim 1, wherein the compound is of the formula:

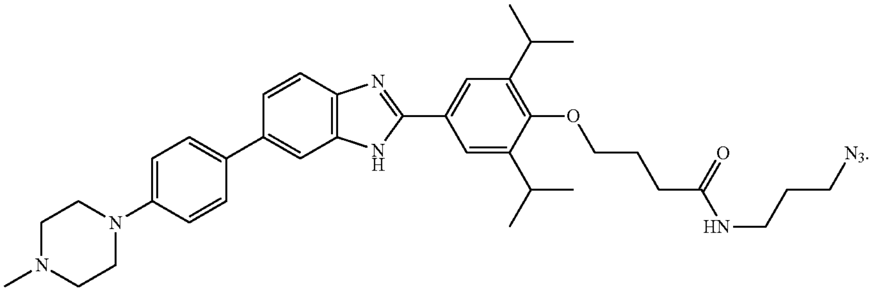 [SMILES: CC(C)c1cc(-c2nc3ccc(-c4ccc(N5CCN(C)CC5)cc4)cc3[nH]2)cc(C(C)C)c1OCCCC(=O)NCCCN=[N+]=[N-]]

5. The compound of claim 1, wherein the compound is of the formula:

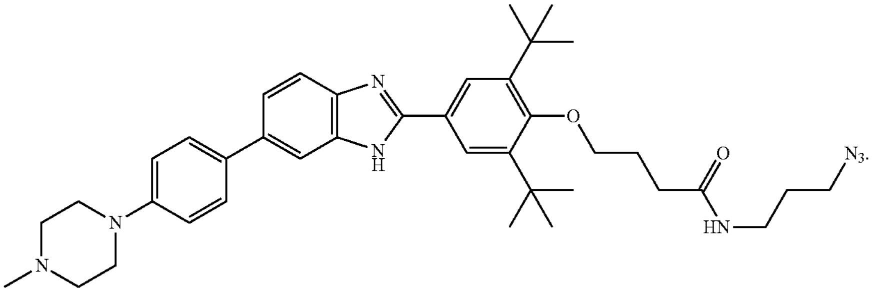

6. A method of inhibiting production of microRNA (miR)-18a, in a prostate cancer cell, from the oncogenic miR-18a hairpin precursor of the miR-17-92 cluster, comprising contacting the prostate cancer cell with an effective amount of a compound of the formula:

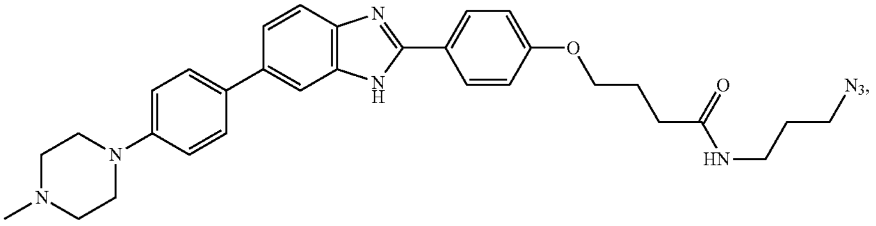

1

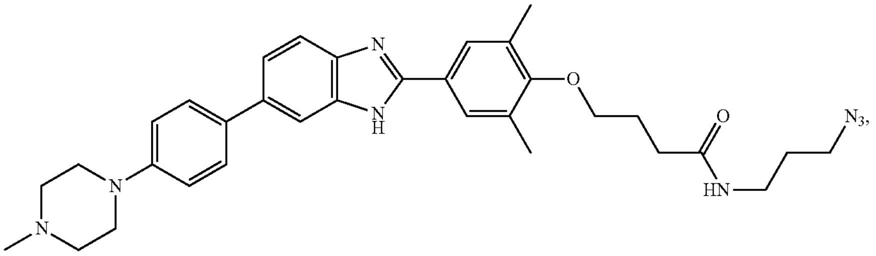

2

-continued
3
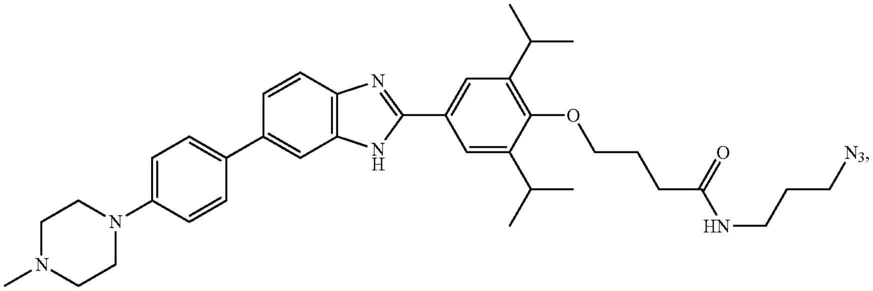
or
4
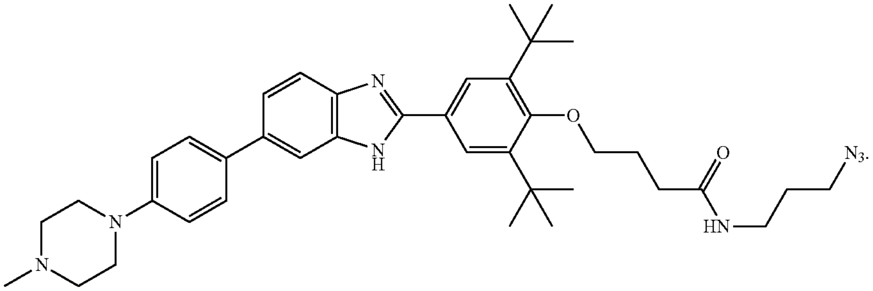 [SMILES: CN1CCN(c2ccc(-c3ccc4nc(-c5cc(C(C)(C)C)c(OCCCC(=O)NCCCN=[N+]=[N-])c(C(C)(C)C)c5)[nH]c4c3)cc2)CC1]
7. The method of claim 6, wherein the compound of the formula:
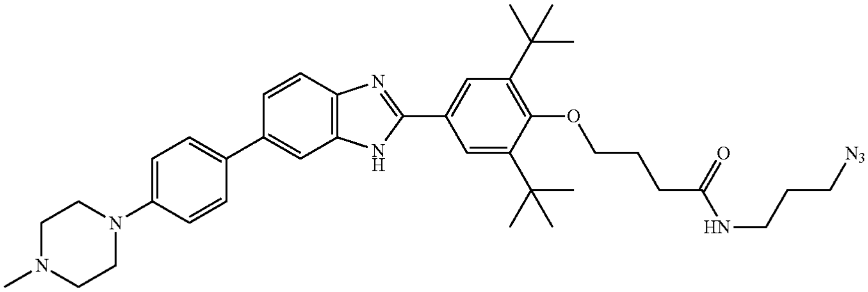
contacting the prostate cancer cell further de-represses serine/threonine protein kinase 4 protein and triggers apoptosis of the prostate cancer cell.
8. The method of claim 6, wherein the compound of the formula:
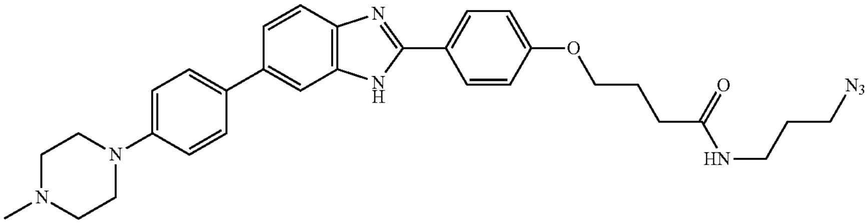

contacting the prostate cancer cell further de-represses serine/threonine protein kinase 4 protein and triggers apoptosis of the prostate cancer cell.

9. The method of claim 6, wherein the compound of the formula:

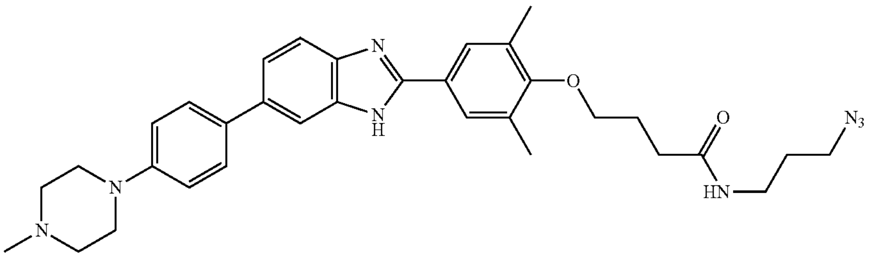

contacting the prostate cancer cell further de-represses serine/threonine protein kinase 4 protein and triggers apoptosis of the prostate cancer cell.

10. The method of claim 6, wherein the compound of the formula:

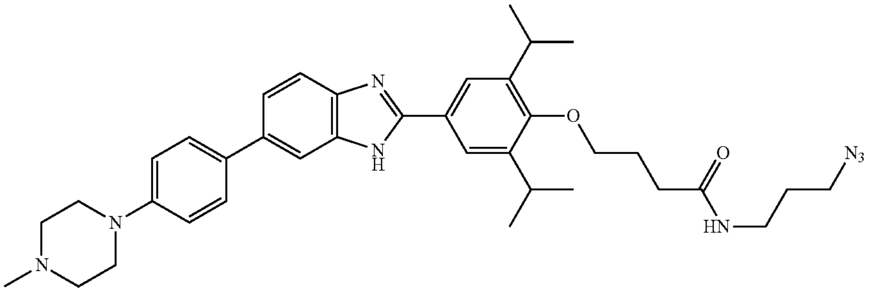

contacting the prostate cancer cell further de-represses serine/threonine protein kinase 4 protein and triggers apoptosis of the prostate cancer cell.

11. The method of claim 6, wherein the compound is of the formula:

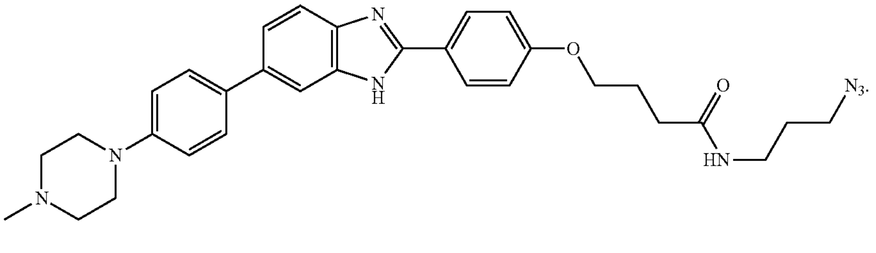 [SMILES: CN1CCN(c2ccc(-c3ccc4nc(-c5ccc(OCCCC(=O)NCCCN=[N+]=[N-])cc5)[nH]c4c3)cc2)CC1]

12. The method of claim 6, wherein the compound is of the formula:
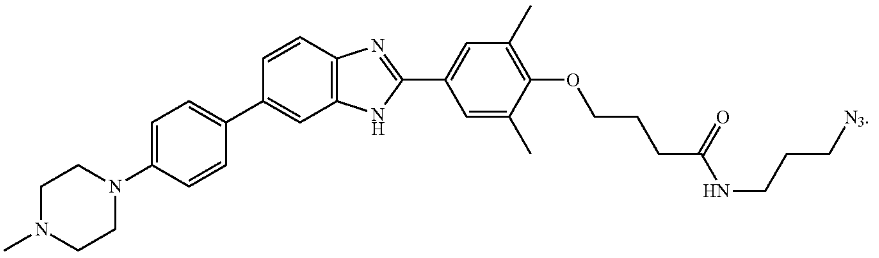 [SMILES: Cc1cc(-c2nc3ccc(-c4ccc(N5CCN(C)CC5)cc4)cc3[nH]2)cc(C)c1OCCCC(=O)NCCCN=[N+]=[N-]]
13. The method of claim 6, wherein the compound is of the formula:
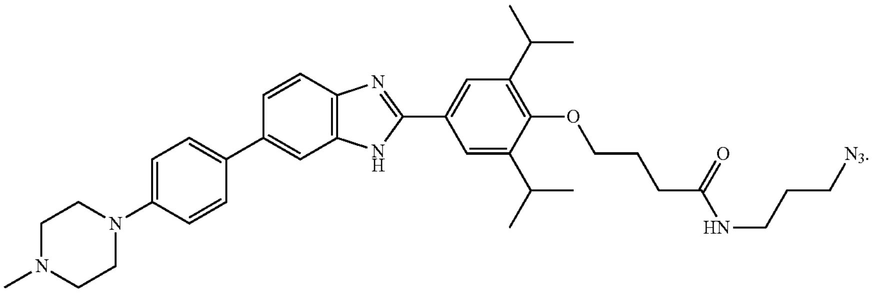 [SMILES: CC(C)c1cc(-c2nc3ccc(-c4ccc(N5CCN(C)CC5)cc4)cc3[nH]2)cc(C(C)C)c1OCCCC(=O)NCCCN=[N+]=[N-]]
14. The method of claim 6, wherein the compound is of the formula:
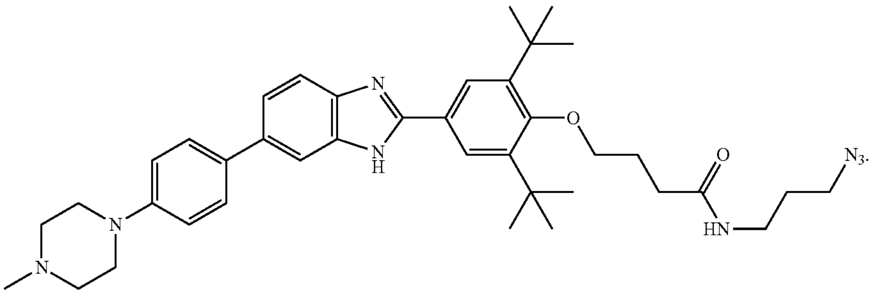
15. A method of treatment of prostate cancer, comprising administering to a mammal afflicted therewith an effective dose of a compound of the formula:
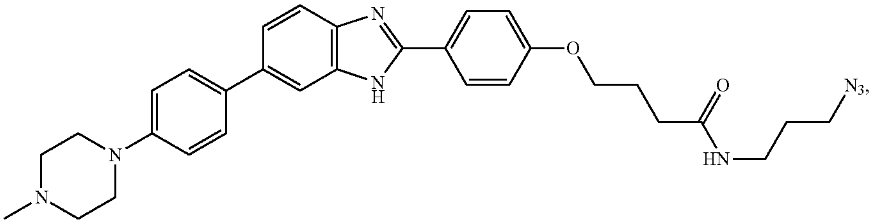

-continued
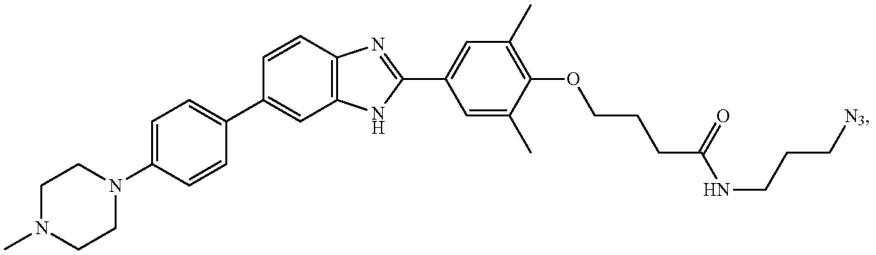
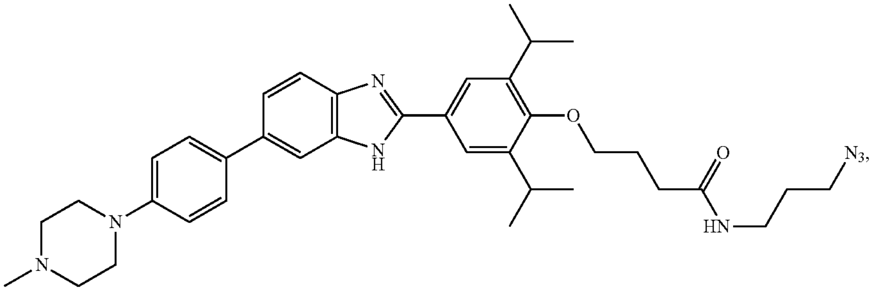
or
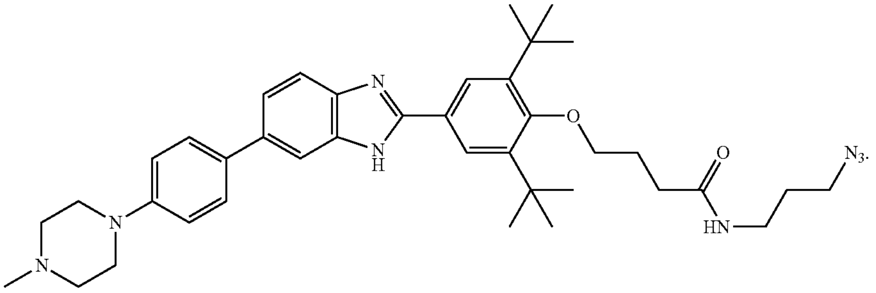
16. The method of claim 15, wherein the compound is of the formula:
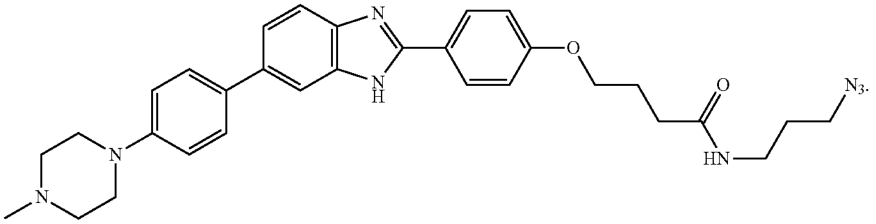
17. The method of claim 15, wherein the compound is of the formula:
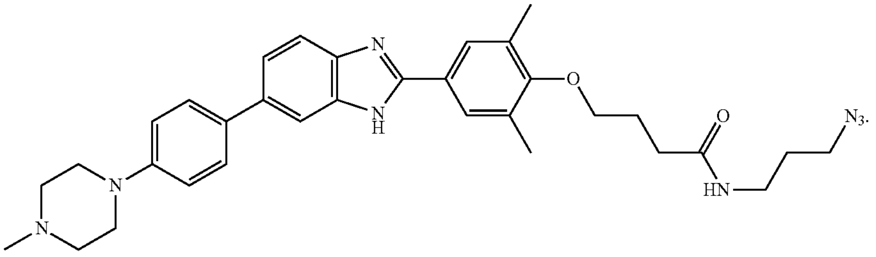

18. The method of claim 15, wherein the compound is of the formula:
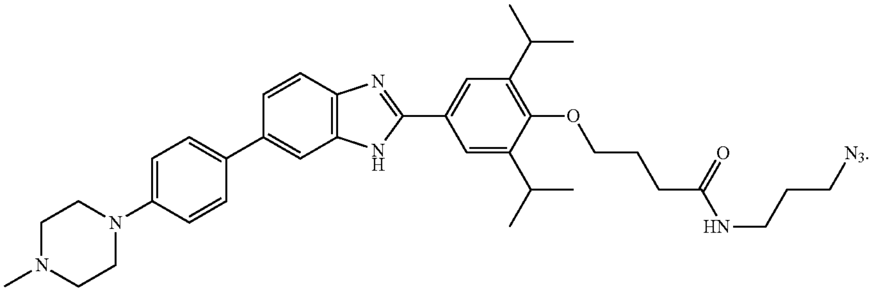
19. The method of claim 15, wherein the compound is of the formula:
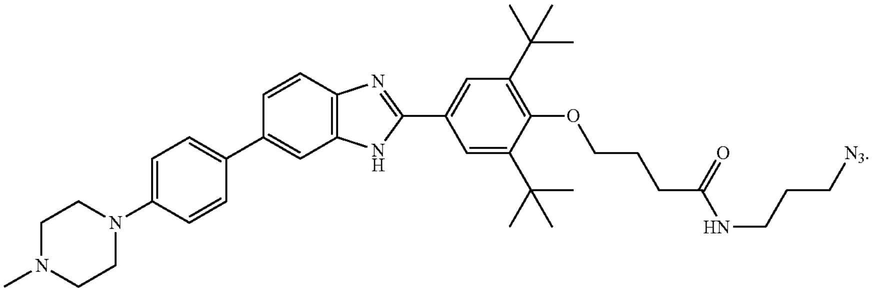 [SMILES: CN1CCN(c2ccc(-c3ccc4nc(-c5cc(C(C)(C)C)c(OCCCC(=O)NCCCN=[N+]=[N-])c(C(C)(C)C)c5)[nH]c4c3)cc2)CC1]
* * * * *